United States Patent
Ye et al.

(10) Patent No.: US 8,853,493 B2
(45) Date of Patent: Oct. 7, 2014

(54) VIRUS INDUCED GENE SILENCING (VIGS) FOR FUNCTIONAL ANALYSIS OF GENES IN COTTON

(75) Inventors: Jian Ye, Singapore (SG); Nam Hai Chua, Singapore (SG); Jing Qu, Singapore (SG); Yun Feng Geng, Singapore (SG); Yun Ping Bu, Singapore (SG)

(73) Assignee: Temasek Life Sciences Laboratory Limited, Singapore (SG)

( * ) Notice: Subject to any disclaimer, the term of this patent is extended or adjusted under 35 U.S.C. 154(b) by 247 days.

(21) Appl. No.: 13/376,902

(22) PCT Filed: Jun. 10, 2010

(86) PCT No.: PCT/SG2010/000220
§ 371 (c)(1),
(2), (4) Date: Dec. 8, 2011

(87) PCT Pub. No.: WO2010/144058
PCT Pub. Date: Dec. 16, 2010

(65) Prior Publication Data
US 2012/0096595 A1    Apr. 19, 2012

Related U.S. Application Data

(60) Provisional application No. 61/185,631, filed on Jun. 10, 2009.

(51) Int. Cl.
*A01H 1/00* (2006.01)
*C12N 15/82* (2006.01)

(52) U.S. Cl.
CPC .............. *C12N 15/8218* (2013.01); *C12N 15/8261* (2013.01)
USPC ............ 800/294; 800/285; 800/290; 436/469

(58) Field of Classification Search
None
See application file for complete search history.

(56) References Cited

U.S. PATENT DOCUMENTS

| 6,369,296 B1 * | 4/2002 | Ratcliff et al. ................. 800/278 |
| 7,476,780 B2 * | 1/2009 | Ryu et al. ....................... 800/285 |
| 2003/0182684 A1 | 9/2003 | Dinesh Kumar et al. |

FOREIGN PATENT DOCUMENTS

WO    2005/103267 A2    11/2005
WO    WO 2005103267 A2 *  11/2005

OTHER PUBLICATIONS

Lee et al, 2007, Annals of Botany, 100:1391-1401.*
Ratcliff, F. et al., "Tobacco rattle virus as a vector for analysis of gene function by silencing," The Plant Journal, 2001, vol. 25, No. 2, pp. 237-245.
Hileman, L.C. et al., "Virus-Induced Gene Silencing is an Effective Tool for Assaying Gene Function in the Basal Eudicot Species *Papaver somniferum* (Opium Poppy)," The Plant Journal, (2005), vol. 44, No. 2, pp. 334-341, © 2005 Blackwell Publishing Ltd., XP-002689517.
Caplan, J. et al., "Using Viral Vectors to Silence Endogenous Genes," Unit 161.6, Current Protocols in Microbiology, vol. Suppl. 1, (Jun. 1, 2006), pp. 161.6, 1-161, 6.13, © 2006 by John Wiley & Sons, Inc., XP-002689519.
EP Communication, Extended European Search Report, dated: Jan. 22, 2013, Reference: RSC/P43020EP; Application No. 10786471.2-2403 / 2440666 PCT/SG2010000220, Applicant: Temasek Life Sciences Laboratory Limited, 9 pages.

* cited by examiner

*Primary Examiner* — David H Kruse
*Assistant Examiner* — Jason Deveau Rosen
(74) *Attorney, Agent, or Firm* — Rothwell, Figg, Ernst & Manbeck P.C.

(57) ABSTRACT

The invention relates to the functional analysis of genes in cotton by employing the Virus Induced Gene Silencing (VIGS) method. More specifically this method induces gene silencing in cotton with the help of the Tobacco Rattle Virus (TRV) vectors RNA1 and RNA2 and phenotypic effects on the cotton plant can be analysed Moreover this invention also provides transient expression vector TRV RNA2 in order to transiently express genes in cotton plants and plant tissue under the influence of a strong subgenomic promoter.

13 Claims, 27 Drawing Sheets

```
                    1                                                50
AtAS1       (1)    MKERORWSGEEDALLXAYVXQXGPRXWHLVSXRMNKXLNRDAKSCXERWX
GhAS1       (1)    MKERORWRXEEDALLCAYVKQXGPREWXLVSHRMNXXLNRDAKSCXERWN
NtAS1       (1)    MXERORWRXEEDALLXAYVKQXGPXEWHLVSQRMNXALNRDXKSCXERWX
SkARP       (1)    MKXXQRWQPEEDALLCAYVXQXGPNXWXLVSXRMAXLDRDPKSCHERWX
Consensus   (1)    MKERQRWRAEEDALLRAYVKQYGPREWNLVSERMNTPLNRDAKSCLERWK
                    51                                               100
AtAS1       (51)   NYLKPGXKXGSLXXEEQRLVIXLQXKXGNKWKXIAAEVPGRTAKRLGKWW
GhAS1       (51)   NYLKPGXKKGSLXXEEQRLVIXLQAKXGNKWKXIAAEVPGRTAKRLGKWW
NtAS1       (51)   NYLKPGXKXGSLXQEEQXLVIHLQAKXGNKWKXIAAEVPGRTAKRLGKWW
SkARP       (51)   NYLKPGXKXGPLXXEEQNLVIXLQXKXGNKWKXIAAEVPGRTAKRLGKWW
Consensus   (51)   NYLKPGIKKGSLTEEEQRLVIRLQEKHGNKWKKIAAEVPGRTAKRLGKWW
                    101                                              150
AtAS1       (101)  EVXKEKQXRXEKEXNKRVXPXDXSXYDRXLEXFAXKXVKERSNVVPXAXA
GhAS1       (101)  EVXKEKQXRXHKEKHXTVXPXXGKYDRXLEXFAXKXVKQGH--------
NtAS1       (101)  EVXKEKQHRXQKENXKXVXXPXDEGKYXHXLEXFAXKXVKERS-------
SkARP       (101)  EVHKE---RRXKEXIQXHQRXQTXVXTSHLSMFYGQTVAPFIPPAQXFXT
Consensus   (101)  EVFKEKQQREQKEANKRVEPIDEGKYDRILETFAEKIVKERS     A A
                    151                                              200
AtAS1       (151)  XXTVXMXNSX--GXXLHXXQQVQPXNPXXPPWXXT------SNNXNNXVX
GhAS1       (143)  XXFPMXASX--GXXLHXDPPXPXPPTXXPPXLSN------SXNXSXVTP
NtAS1       (143)  VPXXXMAXSX--GXXLHADAXXPXPQXXPPWLSN------SXATSTXRX
SkARP       (148)  CXEVXSXXSASEGESQCRNEXRMNLXAAFPPTSXEPVLTLGPXVLDXPX
Consensus   (151)  AAAVVMASSN  GGFLHSD PAPAPPTLLPPWLSN       STNASLV A
                    201                                              250
AtAS1       (193)  RPPXWXXXSPSXVAAAXPQPX-XPWLXQQQPERXENGXGGL--------
GhAS1       (185)  PSPSVXLSXSPSXVAAXXP----XPXLQPXRM--XETSX----------
NtAS1       (185)  PSPSVXLXSXSPSXVPPTXTPTXGXPWLXTXXG--PENXX---------
SkARP       (198)  WKPXPRAXSXSELPXLMAXEAIMKPNLSLSLDSGXESXDTDTGTHFNNNK
Consensus   (201)  PSPSVTLSLSPSTVAAAPP  P IPWLQ DR    AENGP
                    251                                              300
AtAS1       (234)  ----VXGSMXPSXS--G-SSXSXXFLSXLVXGCXXLXEGHRAWXDHKKXAA
GhAS1       (218)  ----VXGNRXPXG--XFXRSENXLXSELXXCCXQLEXGRRAWVXHXKXAA
NtAS1       (222)  ----XLXSFPXHGVXPXCGXNPEXXXLVXGCXDLXEGHRAWAAHKXAA
SkARP       (248)  KVSTXXPKDDEFXNEINSDISPGEXIPLXGLVXELEXNKEXWNVQXKNAA
Consensus   (251)       VIGS MPHC  A P SENLFLSELVECCKELEEGHRAWAAHKKEAA
                    301                                              350
AtAS1       (277)  WRLRRXELQLESEXTCXQREKMXEXEXKXKALREEXKNAXXIEXXYREQ
GhAS1       (262)  WRLRRXEXQLEXEXASXRKKMXEXEXKXEALREEXKXTXDXXXAXYREQ
NtAS1       (268)  WRLRRXEXQLESEKXCXVREKMXEXEXKXKALREEXKXTXDXXEAXYXEQ
SkARP       (298)  STLREXKQQLECEXXEXXXQKMLEXEXKXQALRKEEKLYXDXXELXYAEL
Consensus   (301)  WRLRRLELQLESEKICKKREKMEEIEAKIKALREEQKATLDKIEAEYREQ
                    351                                              400
AtAS1       (327)  XVXLRRDAEXKXQKLAXQWTSXXXRLXKXXEQQ-MGCRXDRX--------
GhAS1       (312)  XEXLRRDAEXKEQKLAEQWAXKHXHLXKXXEQXGCXPRXVEPNGQ-----
NtAS1       (318)  XAGLRRDAEXKEQKLAEQWASKHXRLXKXXEQMGXQSRXAXPNGGR----
SkARP       (348)  XAKLDRDAELKXEKLVXSWXLKXNXLVLMFEQXMQXYSSFHGPIFQAIQM
Consensus   (351)  LAGLRRDAEAKEQKLAEQWASKHLRLTKFLEQTGCR RL EPNG
                    401
AtAS1       (368)  --------
GhAS1       (357)  --------
NtAS1       (364)  --------
SkARP       (398)  RGMNSPA-
Consensus   (401)
```

Figure 6

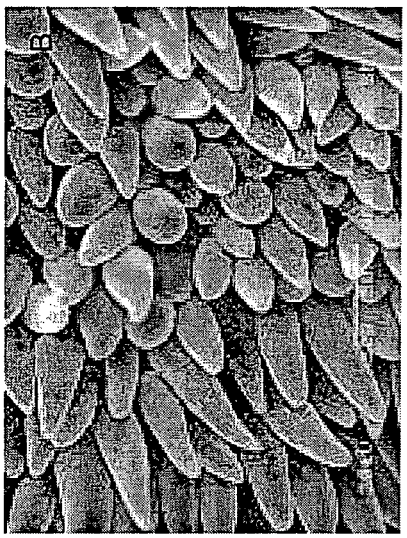
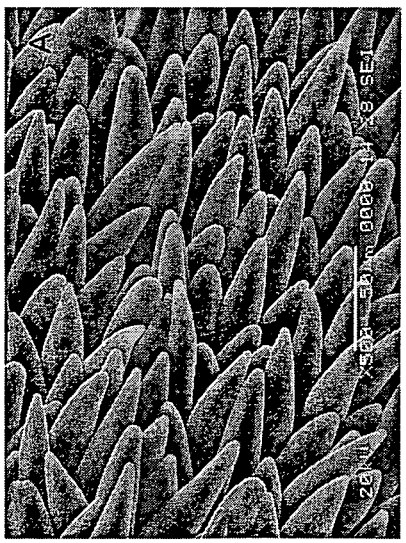
Figs. 24A-24C
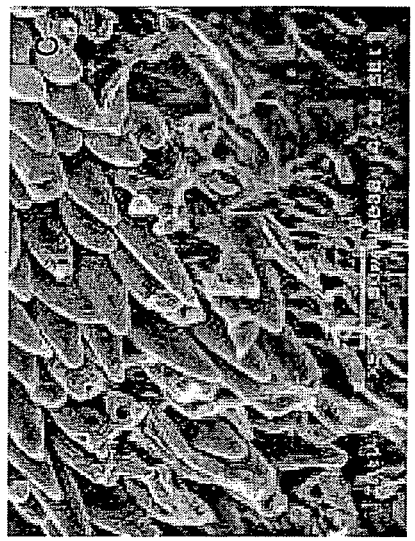
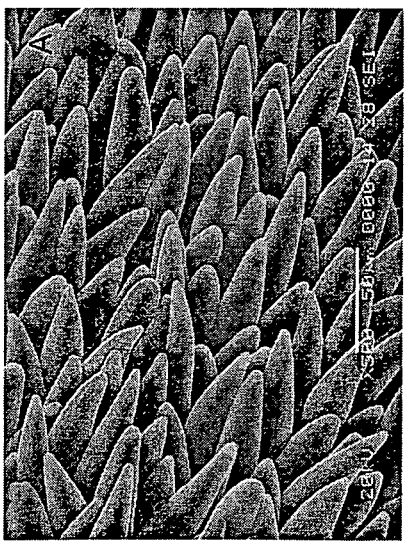
Figs. 25A-25C

VIRUS INDUCED GENE SILENCING (VIGS) FOR FUNCTIONAL ANALYSIS OF GENES IN COTTON

CROSS-REFERENCE TO RELATED APPLICATION

The present application is a national stage filing under 35 U.S.C. §371 of PCT/SG2010/000220, filed on 10 Jun. 2010 which in turn claims priority to U.S. provisional patent application Ser. No. 61/185,631 filed on 10 Jun. 2009, both are incorporated herein by reference.

SEQUENCE LISTING SUBMISSION

The present application is being filed along with a Sequence Listing in electronic format. The Sequence Listing is entitled 2577__195PCT_Sequence_Listing.txt, created on 3 Jun. 2010. The information in the electronic format of the Sequence Listing is incorporated herein by reference in its entirety.

BACKGROUND OF THE INVENTION

The present invention relates to the field of functional analysis of cotton genes on a genomic scale. More specifically, the present invention relates to a method for high-throughput functional analysis of cotton genes on a genomic scale using virus-induced gene silencing (VIGS). The present invention also relates to a transient expression vector for transiently expressing genes in cotton plants and to a method for transient expression of genes in cotton plants.

The publications and other materials used herein to illuminate the background of the invention or provide additional details respecting the practice, are incorporated by reference, and for convenience are respectively grouped in the Bibliography.

Cotton (*Gossypium* spp.) is the world's most important fiber plant and a significant oilseed crop, being grown in more than 80 countries with a record of 122 million 480-pound bales in world production during the 2006/2007 growing season (United States Department of Agriculture-Foreign Agricultural Service). The deficit between consumption and production has happened in 1994/1995 and is forecasted to continue to widen to 2.5 million 480-pound bales in the 2009/2010 growing season (United States Department of Agriculture-Foreign Agricultural Service [USDA-FAS] 2009). Cotton production provides income for approximately 100 million families, and approximately 150 countries are involved in cotton import and export (Lee et al., 2007). Its economic impact is estimated to be approximately $500 billion/year worldwide. Moreover, modifying cotton-seed for food and feed could profoundly enhance the nutrition and livelihoods of millions of people in food-challenged economies. Cotton is also a potential candidate plant of renewable biofuel. Cotton fiber is composed of nearly pure cellulose. Compared to lignin, cellulose is easily convertible to biofuels. Optimized cotton fiber production and processing will ensure that this natural renewable product will be competitive with petroleum-derived synthetic non-renewable fiber to ensure more sustainable development.

To solve the issues stated above, many agronomic properties of cotton, such as fiber length and strength, agricultural productivity, drought tolerance and pest resistance need to be enhanced by the availability of genetic resources and rapid methods to identify gene functions (Udall et al., 2006).

Cotton is an important crop that is widely grown and is used to produce both natural textile fiber and cotton seed oil. Cotton fiber is a model system for the study of cell elongation and cell wall and cellulose biosynthesis. And it is unicellular, therefore cell elongation can be evaluated independently from cell division. One of the most significant benefits for using cotton fiber as a model system for plant development is that a culture method for cotton ovules was perfected by Beasley and Ting (1973).

*Gossypium* includes approximately 45 diploid (2n=2x=26) and five tetraploid (2n=4x=52) species, all exhibiting disomic patterns of inheritance. Most modern cotton varieties are forms of *Gossypium hirsutum* (upland cotton, tetraploid), about 95% of annual cotton crop world wide, although three other species are also utilized to a lesser extent, *Gossypium barbadense* (tetraploid), *Gossypium arboreum* (diploid), and *Gossypium herbaceum* (diploid). These three species are also very important genetic resources and offer gene reservoir for special breeding purpose. For example, *G. herbaceum*, with high resistance to biotic and abiotic stresses, can be used as a good start genetic material for interspecies crossings with *G. hirsutum* to improve its resistance to various stresses. Therefore, a species independent method for gene functional analysis in *Gossypium* genus and relative plants is also greatly needed.

Currently, complete sequencing of cotton genomes is just beginning. Meanwhile, an ever-expanding set of *Gossypium* EST sequences (about 400,000 now) and derived unigene sets from different libraries constructed from a variety of tissues and organs under a range of growth conditions are accessible on the web, as well as by microarray analyses based on these sequences (Udall et al., 2006). The availability of other plant genomic sequences serves as a useful platform for identifying and annotating putative orthologs in cotton EST databases. Even though analogies can be drawn between cotton fiber differentiation and the formation of leaf trichomes and secondary-walled xylem cells, ultimately the function of putative orthologous genes needs to be tested directly in cotton. In addition, cotton fibers are known to express genes with no known homologs in other plants, which may confer some of the unique properties of fibers. Even if the function of several transcriptional factors genes have been tested in *Arabidopsis*, their exact functions need to be further verified in the homologus cotton plant.

An important strategy to identify agronomic and quality traits of *Gossypium* is by stable transformation into cotton. However, the inefficient production of stably transformed cotton plants limits gene identification on a large scale. Moreover, such procedure is laborious and time consuming and not suitable for high throughput analysis on a genomic scale. Furthermore, only few cultivars can be used for host for transformation. Normally, it is difficult to directly identify important genetic elements from good start genetic materials by stable transformation in cotton.

Thus, it is desired to develop a method for the species independent high-throughput functional analysis of *Gossypium* genes on a genomic scale.

SUMMARY OF THE INVENTION

The present invention, in one embodiment, relates to a method of directly manipulating expression of a target gene in cotton (*Gossypium* spp.) plants. More specifically, the present invention relates to a method of modulating or inhibiting expression of one or more target genes in all cotton species and germplasms, in particular, in tetraploid cotton, such as upland cotton (*Gossypium hirsutum*) and *Gossypium bar-*

*badense*, in diploid cotton, such as *Gossypium herbaceum* and *Gossypium arboreum*, and in germplasms derived from intra-species and inter-species crossings. Genes belonging to several functional categories, including transcriptional factor involved in development, small RNA pathway and secondary metabolites biosynthesis, etc have been tested by this method. It is specifically contemplated that the methods and compositions of the present invention are useful in the functional analysis of cotton genes.

The present invention relates to the field of functional analysis of cotton genes on a genomic scale. More specifically, the present invention relates to a method for high-throughput functional analysis of cotton genes on a genomic scale using virus-induced gene silencing (VIGS). The present invention also relates to a transient expression vector for transiently expressing genes in cotton plants and plant tissue and to a method for transient expression of genes in cotton plants and plant tissue.

The present invention relates to the use of VIGS to evaluate gene function in cotton (*Gossypium* spp.) plants and plant tissue reliably and rapidly, and in a high-throughput manner. In one aspect, the present invention provides an efficient and reproducible system and procedure for VIGS in cotton (such as, *Gossypium hirsutum*). In one embodiment, the present invention provides for the further re-synthesis of the whole tobacco rattle virus (TRV) viral genomes. In an additional embodiment, the present invention provides for a rapid silencing procedure for genome wide functional analysis. In a further embodiment, the present invention provides for the use of TRV VIGS system for cloning and functional identifying several functional categories genes. These important genes can be used to improve cotton agronomic traits such as pest resistance.

In one embodiment, the vector comprising TRV RNA2 and the vector comprising TRV RNA1 are synthetic plant vectors. In another embodiment, the TRV RNA2 comprises a first silencing sequence that is capable of silecing a first desired gene. In one embodiment, the first silencing sequence is the sequence of a sense strand of the desired gene. In an additional embodiment, the first silencing sequence is the sequence of an antisense strand of the desired gene. In another embodiment, the first silencing sequence is a sequence encoding a short hairpin RNA (shRNA) that is capable of RNA interference (RNAi) of the first desired gene. In an additional embodiment, the first silencing is a sequence encoding a precursor micro-RNA (miRNA) or miRNA that is capable of RNAi of the first desired gene. In a further embodiment, the nucleic acid further comprises a second silecing sequence capable of silecing a second desired gene. In a further embodiment, the nucleic acid comprises more than two silencing sequences capable of silencing more than two desired genes.

In some embodiments, the desired gene is a candidate transcription factor gene. In another embodiment, the desired gene is a candidate gene in chlorophyll or carotenoids biosynthesis. In a further embodiment, the desired gene is a candidate gene in flavonoid biosynthetic pathway. In another embodiment, the desired gene is a candidate gene in proanthocyanidins and anthocyanidins biosynthetic pathway. In an additional embodiment, the desired gene is a candidate gene in cotton fiber development. In a further embodiment, the desired gene is a candidate gene in cotton fiber initiantion, elongation, secondary wall deposition, maturation or seed development. In one embodiment, the desired gene is a candidate gene in small RNA (smRNA) biosynthesis. In another embodiment, the desired gene is a candidate gene in biosynthesis of secondary metabolic toxic agents and also important for plant resistance to biotic stress. In a further embodiment, the desired gene is a candidate gene correlating to cell elongation, cell wall biosynthesis and cellulose biosynthesis.

Thus in a first aspect, the present invention provides a method of virus-induced gene silencing (VIGS) in cotton. In accordance with this aspect, the method comprises:

(a) inserting a nucleic acid comprising a first silencing sequence that is capable of silencing a first desired gene into a vector comprising a tobacco rattle virus (TRV) RNA2 sequence to produce a modified TRV RNA2 vector;

(b) preparing a mixed culture of *Agrobacterium* comprising *Agrobacterium* containing a vector comprising a TRV RNA1 sequence and *Agrobacterium* containing the modified TRV RNA2 vector;

(c) introducing the mixed culture of *Agrobacterium* into plant tissue of cotton to produce infected plant tissue; and (d) growing the infected plant tissue for a sufficient time to induce gene silencing of the first desired gene.

In one embodiment of this first aspect, the plant tissue is a cotton plant or a cotton seedling. In this embodiment, an infected plant is produced in step (c) and the infected plant is grown in step (d). In another embodiment of this first aspect, the plant tissue is a cotton ovule. In this embodiment, an infected cotton ovule is produced in step (c) and the infected cotton ovule is grown in culture in step (d). In an additional embodiment, the plant tissue is cotton fiber. In this embodiment, infected cotton fiber is produced in step (c) and the infected cotton fiber is grown in culture in step (d). In a further embodiment, a cotton plant or seedling is infected and the virus spreads through the cotton tissue, such that VIGS occurs in all tissue of the infected cotton plant or seedling.

In another aspect, the present invention provides a method of analyzing gene function in cotton. In accordance with this aspect, the method comprises:

(a) inserting a nucleic acid comprising a silencing sequence that is capable of silencing a candidate gene into a vector comprising a tobacco rattle virus (TRV) RNA2 sequence to produce a modified TRV RNA2 vector;

(b) preparing a mixed culture of *Agrobacterium* comprising *Agrobacterium* containing a vector comprising a TRV RNA1 sequence and *Agrobacterium* containing the modified TRV RNA2 vector;

(c) introducing the mixed culture of *Agrobacterium* into plant tissue of cotton to produce infected plant tissue;

(d) growing the infected plant tissue for a sufficient time to induce gene silencing of the candidate gene; and (e) analyzing the phenotypic effect of the silenced candidate gene on the infected plant tissue.

In one embodiment of this second aspect, the plant tissue is a cotton plant or a cotton seedling. In this embodiment, an infected plant is produced in step (c) and the infected plant is grown in step (d). In another embodiment of this first aspect, the plant tissue is a cotton ovule. In this embodiment, an infected cotton ovule is produced in step (c) and the infected cotton ovule is grown in culture in step (d). In an additional embodiment, the plant tissue is cotton fiber. In this embodiment, infected cotton fiber is produced in step (c) and the infected cotton fiber is grown in culture in step (d). In a further embodiment, a cotton plant or seedling is infected and the virus spreads through the cotton tissue, such that VIGS occurs in all tissue of the infected cotton plant or seedling.

In a further aspect, the present invention provides a transient expression vector and method for transiently expressing genes in cotton plants or cotton tissue. In accordance with this aspect, the transient expression vector comprises a TRV RNA2 sequence and at least one copy of a strong subgenomic promoter and optionally a nucleic acid comprising a first sequence of interest. In one embodiment, the subgenomic promoter is one that is recognized by the replicase of TRV. In another embodiment, the subgenomic promoter is a strong coat protein subgenomic promoter. In a further embodiment, the subgenomic promoter is derived from a Tobravirus other than TRV. In one embodiment, the subgenomic promoter is a synthetic pea early browning virus (PEBV) subgenomic promoter. In another embodiment, the subgenomic promoter is a Pepper ringspot virus (PepRSV) coat protein subgenomic promoter. The nucleic acid of interest for transient expression in cotton is inserted downstream of the subgenomic promoter and is operably linked to this promoter.

In accordance with this aspect, the method for transiently expressing a nucleic acid of interest in cotton tissue comprises:

(a) inserting a nucleic acid comprising a first sequence of interest to be expressed in a cotton plant into a transient expression vector comprising a tobacco rattle virus (TRV) RNA2 sequence and at least one copy of a strong subgenomic promoter to produce a TRV RNA2 expression vector, wherein the nucleic acid is operably linked to the subgenomic promoter;

(b) preparing a mixed culture of *Agrobacterium* comprising *Agrobacterium* containing a vector comprising a TRV RNA1 sequence and *Agrobacterium* containing the TRV RNA2 expression vector;

(c) introducing the mixed culture of *Agrobacterium* into plant tissue of cotton; and (d) growing the infected plants for a sufficient time to transiently express the desired gene.

In one embodiment of this further aspect, the plant tissue is cotton seedlings. In another embodiment of this further aspect, the plant tissue is cotton ovules. In an additional embodiment of this further aspect, the plant tissue is cotton plants. In a further embodiment, the plant tissue is cotton fiber. In a still further embodiment, a cotton plant or seedling is infected and the virus spreads through the cotton tissue, such that VIGS occurs in all tissue of the infected cotton plant or seedling.

In another aspect, the present invention provides a modified TRV RNA1 vector. In accordance with this aspect, the modified TRV RNA1 vector comprises the TRV RNA1 sequence into which at least one intron has been inserted. In a further aspect, TRV RNA genome is modified to remove putative intron-like features and potential problematic regions, such as long thymine-rich sequence. This modified TRV RNA1 vector can be used in place of the vector containing TRV RNA1 in any of the above methods.

BRIEF DESCRIPTION OF THE FIGURES

FIG. 3A: Phenotypes of cotton plants infected with control and psTRV2:CAD. FIG. 3B: Quantitative real-time PCR using total RNA extracted from upper leaves of treated plants. The real-time PCR analysis showed that CAD transcript levels were greatly reduced in systemic leaves. FIG. 3C: HPLC chromatograms of gossypol and related sesquiterpenoids from cad silenced cotton leaves. CK: vector control infected; CAD, leaves from plants silenced in cadinene synthase expression. tert-butylanthraquinone was used as an internal standard.

FIG. 4A shows cotton leaves taken at 14 days post inoculation (DPI), while FIG. 4B show cotton buds and taken at 45 DPI. The CH42 enzyme is responsible for adding Mg into the porphyrin ring during chlorophyll biosynthesis. Silencing of the CH42 gene blocked chlorophyll synthesis in newly emerging leaves which lost their green color but appeared yellow owing to the presence of carotenoids. FIG. 4C: Quantitative RT-PCR analysis to determine the RNA level of silenced *G. hirsutum* CH42 RNA levels in the CH42 treated and *G. hirsutum* PDS RNA levels on PDS treated cotton new emerged leaves. The numbers represent average values from 3 independent experiments with standard deviations. The real-time PCR analysis showed that CH42 and PDS transcript levels were greatly reduced in systemic leaves.

FIG. 6 shows the amino acid sequence comparison of the predicted putative cotton AS1 (GhAS1) protein (SEQ ID NO:18) with the *Arabidopsis thaliana* AS1, AtAS1 (GenBank accession number: NM_129319; SEQ ID NO:19), *Nicotiana tabacum* AS1, NtAS1 (GenBank accession number: AY559043; SEQ ID NO:20), and *Selaginella kraussiana* ARP, SkARP (GenBank accession number: AY667452; SEQ ID NO:21). CLUSTALW produced alignment file was formatted and consensus sequence (SEQ ID NO:22) was listed below. The conserved R2R3 MYB domain is underlined.

FIGS. 7A-7D: Phenotypes of cotton plants infected with psTRV2:AS1. FIGS. 7F and 7G: Scanning electron microscopy of cotton plants infected with psTRV2:AS1.

FIG. 9A: Phenotypes of cotton plants infected with psTRV2:ANS or with sTRV2:ANR showing effects on leaves, petioles and buds. FIG. 9B: Quantitative real-time PCR using total RNA extracted from upper leaves of treated plants. The real-time PCR analysis showed that ANR and ANS transcript levels were greatly reduced in systemic leaves. CK: vector control infected; ANR, leaves from plants silenced in ANR expression; ANS, leaves from plants silenced in ANS expression.

FIG. 20A: Phenotype of plants infected with empty vector. FIGS. 20B-20D: Phenotypes of plants infected with psTRV2: GFP. FIG. 20E: Western blot of plants infected with psTRV2: GFP. Top panel: GFP protein band detected with anti-GFP antibody. Bottom panel: rbcL band stained with coomassie brilliant blue, which serves as a loading control. Lane 1: empty vector, lanes 2-4, 3 independent plants infiltrated with psTRV2:GFP.

FIG. 21A: 2-week culture in BT medium. FIG. 21B: Length of fibers on in vitro ovule culture.

FIG. 22A: Ovules treated with psTRV1+psTRV2. All of ovules can grow fiber well. FIG. 22B: Ovules treated with psTRV1+psTRV2:Actin 1. Although the ovules can grow fiber, fibers were shorter than control fibers.

FIGS. 23A-23D: Ovules infected by psTRV1+psTRV2 at 0 (FIG. 23A), 1 (FIG. 23B), and 2 (FIG. 23C, FIG. 23D) DPA and scanned on 1 (FIG. 23A, FIG. 23B, FIG. 23C), and 2 (FIG. 23D) days after infected. Note the length of fibers increases with time. FIGS. 23E-23H: Ovules infected by psTRV1+psTRV2:Actin 1 at 0 (FIG. 23E), 1 (FIG. 23F), and 2 (FIG. 23G, FIG. 23H) DPA and scanned on 1 (FIG. 23E, FIG. 23F, FIG. 23G), and 2 (FIG. 23H) days after infected. Note the length of fibers is much shorter than that in psTRV1+psTRV2 at the same stages and the surface of trichome is rough and wrinkled. FIGS. 23I-23L: Ovules infected by psTRV1+psTRV2:GhADF 1 at 0 (FIG. 23I), 1 (FIG. 23J), and 2 (FIG. 23K, FIG. 23L) DPA and scanned on 1 (FIG. 23I, FIG. 23J, FIG. 23K), and 2 (FIG. 23L) days after infected. Note the length of fibers is same as psTRV1+psTRV2 at the same stages.

FIGS. 24A-24C show scanning electron micrographs of the ovule surface of VIGS-GhCTR 1, VIGS-GhDELLA 1 and psTRV1+psTRV2. FIG. 24A: Ovules infected by psTRV1+psTRV2 at 1 DPA and scanned on 1 day after infected. FIG. 24B: Ovules infected by psTRV1+psTRV2:GhCTR 1 at 1 DPA and scanned on 1 day after infected. Note the length of fibers is shorter than sTRV1+sTRV2 at the same stages. FIG. 24C: Ovules infected by psTRV1+psTRV2:GhDELLA 1 at 1 DPA and scanned on 1 day after infected. Note the length of fibers is same as psTRV1+psTRV2 at the same stages.

FIGS. 25A-25C show scanning electron micrographs of the ovule surface of VIGS-GhAlpha-tubulin 1, VIGS-GhBeta-tubulin 1 and psTRV1+psTRV2. FIG. 25A: Ovules infected by psTRV1+psTRV2 at 1 DPA and scanned on 1 day after infected. FIG. 25B: Ovules infected by psTRV1+psTRV2:GhAlpha-tubulin1 DPA and scanned on 1 day after infected. Note the surface of trichome is rough and wrinkled. FIG. 25C: Ovules infected by psTRV1+psTRV2:ADFGhBeta-tubulin 1 at 1 DPA and scanned on 1 day after infected. Note the surface of trichome is rough and wrinkled.

FIG. 26A: Ovules infected by psTRV1+psTRV2 at 1 DPA and scanned on 3 days after infected. FIG. 26B: Ovules infected by psTRV1+psTRV2:GhMADS 9 at 1 DPA and scanned on 3 days after infected. Note the length of fibers is longer than sTRV1+sTRV2 at the same stages. FIG. 26C: Ovules infected by psTRV1+psTRV2:ADFGhMYB 5 at 1 DPA and scanned on 3 dayS after infected. Note the length of fibers is same as psTRV1+psTRV2 at the same stages. FIG. 26D: Ovules infected by psTRV1+psTRV2:ADFGhMYB 6 at 1 DPA and scanned on 3 days after infected. Note the length of fibers is same as sTRV1+sTRV2 at the same stages.

FIG. 27A: Control using tubulin gene as the RNA standard. FIG. 27B: GhActin 1 gene expression in cotton fibers. The result of RT-PCR showed that VIGS of Actin 1 caused significant reduction in its mRNA expression.

DETAILED DESCRIPTION OF THE INVENTION

Figure 1:
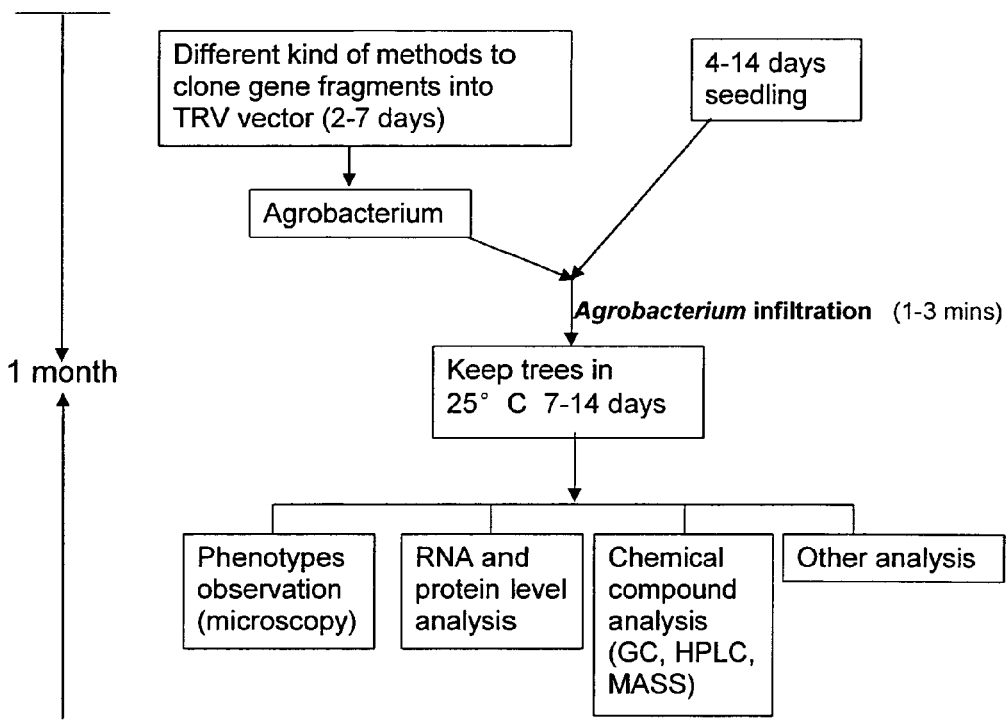
FIG. 1 illustrates a method for cotton transient expression in accordance with the present invention. The transient expression can be used for virus-induced gene silencing (VIGS) or for gene expression.

The present invention relates to the field of functional analysis of cotton genes on a genomic scale. More specifically, the present invention relates to a method for high-throughput functional analysis of cotton genes on a genomic scale using virus-induced gene silencing (VIGS). The present invention also relates to a transient expression vector for transiently expressing genes in cotton plants and to a method for transient expression of genes in cotton plants.

Virus-induced gene silencing (VIGS) (Ruiz et al., 1998; Burch-Smith et al., 2004) system offers the possibility to determine the biological function of gene products without the need to genetically transform the plant. Both RNA and DNA viruses induce RNA silencing resulting in the production of virus-related siRNAs (Baulcombe, 2004). Recombinant viruses can be constructed carrying an inserted partial sequence of a candidate plant gene. Such recombinant viruses can move systemically in whole plants producing siRNA which can mediate degradation of the endogenous candidate gene transcripts (Brigneti et al., 2004; Burch-Smith et al., 2004) resulting in silencing of the candidate gene expression in inoculated plants.

VIGS approach offers several opportunities:

(1) an efficient reverse genetics tool to gene/gene family knock-down;

(2) a rapid and high-throughout (Nasir et al., 2005)—whole genome ORF knock-out in less than one month;

(3) transient, reversible and so called "inducible" knock-out phenotype (Burch-Smith et al., 2004); and (4) different organs suitable for silencing, offer a chance to knock-out genes in roots (Valentine et al., 2004), flowers (Liu et al., 2004), leaves (Liu et al., 2002), or fruit (Fu et al., 2005), by different infection methods.

The tobacco rattle virus (TRV) is a bipartite positive sense RNA virus. TRV RNA1 encodes 134 kDa and 194 kDa replicase proteins from the genomic RNA, a 29-kDa movement protein and 16-kDa cysteine-rich protein from subgenomic RNAs. TRV RNA2 encodes the coat protein from the genomic RNA and two non-structural proteins from the subgenomic RNAs. TRV RNA1 can replicate and move systemically without RNA2. In the TRV RNA2 cDNA construct, the non-structural genes were replaced with a multiple cloning site (MCS) useful for cloning the target gene sequences for VIGS (MacFarlane and Popovich, 2000).

The TRV VIGS system has been successfully applied in some plants such as *Arabidopsis* (Burch-Smith et al., 2006), *Capsicum annuum* (Chung et al., 2004), *Lycopersicon esculentum* (Liu et al., 2002), *Petunia hybrida* (Chen et al., 2005) and *Solanum tuberosum* (Brigneti et al., 2004). Most of these plants have been experimentally proven to be susceptible hosts of some strain of TRV (Plant Virus Online, http colon backslash backslash image dot fs dot uidaho dot edu backslash vide backslash descr808 dot htm). More importantly, this TRV VIGS system cannot reasonably be expected to inevitably work in all plants. For example, Dinesh Kumar et al. (2007) contains a list of plants for which it is stated that the TRV VIGS system may work. However, this TRV VIGS system cannot work in *Arachis hypogaea* and *Glycine max*, because they are not hosts to TRV despite their inclusion in the list in Dinesh Kumar et al. (2007). In fact, as demonstrated herein, the TRV VIGS system does not work in all plants listed as being susceptible to Tobacco Rattle Virus (TRV) in Dinesh Kumar et al. (2007) or in the online virus databases. Furthermore, systemic infection is required for the TRV VIGS system to be useful for functional gene analysis. Some plants may be susceptible to TRV locally but not systemically, and thus the TRV VIGS system will not work in those plants. Prior to the present invention, plants in Malvales including cotton plants (*Gossypium* spp.) were not known to be host to TRV or known to be susceptible in any degree to TRV either locally or systemically. The finding that cotton is susceptible to TRV and that the TRV VIGS system can be used in cotton was discovered after screening many viral vectors and thus was unexpected. The unexpected nature of the present invention is further evidenced by the inability of the TRV VIGS system to work in all plants which are susceptible to TRV or are listed as host plants for TRV.

In one aspect, the present invention provides an efficient and reproducible system and procedure for VIGS in cotton. In one embodiment, the present invention provides for the further re-synthesis of the whole TRV viral genomes. In another embodiment, the present invention demonstrates that these vectors have similar efficiency as the original vectors. In a further embodiment, the present invention provides for the use of TRV VIGS system for cloning and functionally identifying cotton genes. In accordance with this aspect, the transient expression vector comprises a TRV RNA2 sequence and at least one copy of a strong subgenomic promoter and optionally a nucleic acid comprising a first sequence of interest. In one embodiment, the subgenomic promoter is one that is recognized by the replicase of TRV. In another embodiment, the subgenomic promoter is a strong coat protein subgenomic promoter. In a further embodiment, the subgenomic promoter is derived from a Tobravirus other than TRV. In one embodiment, the subgenomic promoter is a synthetic pea early browning virus (PEBV) subgenomic promoter. In another embodiment, the subgenomic promoter is a Pepper ringspot virus (PepRSV) coat protein subgenomic promoter. The nucleic acid of interest for transient expression in cotton is inserted downstream of the subgenomic promoter and is operably linked to this promoter. This vector can be used for the transient expression of a nucleic acid of interest in cotton plants. In an additional embodiment, the present invention provides a modified TRV RNA1 vector in which an intron has been inserted into the TRV RNA1 sequence.

Thus in a first aspect, the present invention provides a method of virus-induced gene silencing (VIGS) in cotton. In accordance with the present invention, the method comprises:

(a) inserting a nucleic acid comprising a first silencing sequence that is capable of silencing a first desired gene into a vector comprising a tobacco rattle virus (TRV) RNA2 sequence to produce a modified TRV RNA2 vector;

(b) preparing a mixed culture of *Agrobacterium* comprising *Agrobacterium* containing a vector comprising a TRV RNA1 sequence and *Agrobacterium* containing the modified TRV RNA2 vector;

(c) introducing the mixed culture of *Agrobacterium* into plant tissue of cotton to produce infected plant tissue; and (d) growing the infected plant tissue for a sufficient time to induce gene silencing of the first desired gene.

In one embodiment of this first aspect, the plant tissue is a cotton plant or a cotton seedling. In this embodiment, an infected plant is produced in step (c) and the infected plant is grown in step (d). In another embodiment of this first aspect, the plant tissue is a cotton ovule. In this embodiment, an infected cotton ovule is produced in step (c) and the infected cotton ovule is grown in culture in step (d). In an additional embodiment, the plant tissue is cotton fiber. In this embodiment, infected cotton fiber is produced in step (c) and the infected cotton fiber is grown in culture in step (d). In a further embodiment, a cotton plant or seedling is infected and the virus spreads through the cotton tissue, such that VIGS occurs in all tissue of the infected cotton plant or seedling.

In one embodiment, the vector comprising TRV RNA2 and the vector comprising TRV RNA1 are synthetic plant vectors. The results and the phenotypic data shown herein indicate that the synthetic TRV-VIGS systems can be used as effectively as TRV-VIGS systems to induce silencing of desirable endogenous cotton genes. In another embodiment, the TRV RNA2 comprises a first silencing sequence that is capable of silecing a first desired gene. In one embodiment, the first silencing sequence is the sequence of a sense strand of the desired gene. In an additional embodiment, the first silencing sequence is the sequence of an antisense strand of the desired gene. In another embodiment, the first silencing sequence is a sequence encoding a short hairpin RNA (shRNA) that is capable of RNA interference (RNAi) of the first desired gene. In an additional embodiment, the first silencing is a sequence encoding a precursor micro-RNA (miRNA) or miRNA that is capable of RNAi of the first desired gene. In a further embodiment, the nucleic acid further comprises a second silecing sequence capable of silecing a second desired gene. In a further embodiment, the nucleic acid comprises more than two silencing sequences capable of silencing more than two desired genes.

In one embodiment, the desired gene is a candidate transcription factor gene. In another embodiment, the desired gene is a candidate gene in chlorophyll or carotenoids biosynthesis. In a further embodiment, the desired gene is a candidate gene in flavonoid biosynthetic pathway. In another embodiment, the desired gene is a candidate gene in proanthocyanidins and anthocyanidins biosynthetic pathway. In an additional embodiment, the desired gene is a candidate gene in cotton fiber development. In a further embodiment, the desired gene is a candidate gene in cotton fiber initiation, elongation, secondary wall deposition, maturation or seed development. In another embodiment, the desired gene is a candidate gene in smRNA biosynthesis. In an additional embodiment, the desired gene is a candidate gene in photohermone signal pathway. In another embodiment, the desired gene is a candidate gene invoved in abotic and biotic stress resistance. In an additional emobiment, the desired gene is a candidate gene in fatty acid biosynthesis, such as stearoyl-acyl carrier protein desaturase (SAD) gene. In a further embodiment, the desired gene is a candidate gene in cotton fiber development such as a candidate gene correlating to cell elongation, cell wall biosynthesis and cellulose biosynthesis. In another emobiment, the desired gene is a candidate gene in cotton trichome related. In a further emobiment, the desired gene is a candidate gene in secondary metabolites biosynthesis. The results shown herein demonstrate that the VIGS system of the present invention can efficiently suppress targeted host genes and can be used as a rapid means to assay the role of candidate genes, as well as to study the role of regulatory genes, such a transcription factor genes or the role of genes involved in the small RNA biogenesis pathways. The VIGS assay described herein offers a means to test the function of cotton gene sequences in a homologous system. Using a normalized cDNA library it is possible to conduct large scale screens of gene function with the VIGS system of the present invention.

The host plant can be *Gossypium hirsutum* (upland cotton, tetraploid), but as demonstrated herein, the invention is not limited to this species. Thus, the host plant can also be *Gossypium barbadense* (tetraploid), *Gossypium arboreium* (diploid), and *Gossypium herbaceum* (diploid) and other natural *Gossypium* species and all commercial cotton varieties and germplasms including germplasms derived from intra-species and inter-species crossings.

In a second aspect, the present invention provides a method of analyzing gene function in cotton. In accordance with the present invention, the method comprises:

(a) inserting a nucleic acid comprising a silencing sequence of a candidate gene to be silenced into a vector comprising a tobacco rattle virus (TRV) RNA2 sequence to produce a modified TRV RNA2 vector;

(b) preparing a mixed culture of *Agrobacterium* comprising *Agrobacterium* containing a vector comprising a TRV RNA1 sequence and *Agrobacterium* containing the modified TRV RNA2 vector;

(c) introducing the mixed culture of *Agrobacterium* into plant tissue of cotton to produce infected plant tissue;

(d) growing the infected plant tissue for a sufficient time to induce gene silencing of the candidate gene; and analyzing the phenotypic effect of the silenced candidate gene on the infected plant tissue.

In one embodiment of this second aspect, the plant tissue is a cotton plant or a cotton seedling. In this embodiment, an infected plant is produced in step (c) and the infected plant is grown in step (d). In another embodiment of this first aspect, the plant tissue is a cotton ovule. In this embodiment, an infected cotton ovule is produced in step (c) and the infected cotton ovule is grown in culture in step (d). In an additional embodiment, the plant tissue is cotton fiber. In this embodiment, infected cotton fiber is produced in step (c) and the infected cotton fiber is grown in culture in step (d). In a further embodiment, a cotton plant or seedling is infected and the virus spreads through the cotton tissue, such that VIGS occurs in all tissue of the infected cotton plant or seedling.

In one embodiment, the vector comprising TRV RNA2 and the vector comprising TRV RNA1 are synthetic plant vectors. The results and the phenotypic data shown herein indicate that the synthetic TRV-VIGS systems can be used as effectively as TRV-VIGS systems to induce silencing of desirable endogenous cotton genes. In another embodiment, the TRV RNA2 comprises a first silencing sequence that is capable of silecing a first desired gene. In one embodiment, the first silencing sequence is the sequence of a sense strand of the desired gene. In an additional embodiment, the first silencing sequence is the sequence of an antisense strand of the desired gene. In another embodiment, the first silencing sequence is a sequence encoding a short hairpin RNA (shRNA) that is capable of RNA interference (RNAi) of the first desired gene. In an additional embodiment, the first silencing is a sequence encoding a precursor micro-RNA (miRNA) or miRNA that is capable of RNAi of the first desired gene. In a further embodiment, the nucleic acid further comprises a second silecing sequence capable of silecing a second desired gene. In a further embodiment, the nucleic acid comprises more than two silencing sequences capable of silencing more than two desired genes.

In one embodiment, the desired gene is a candidate transcription factor gene. In another embodiment, the desired gene is a candidate gene in smRNA biosynthesis. In another embodiment, the desired gene is a candidate gene in a candidate gene in proanthocyanidins and anthocyanidins biosynthetic pathway. In an additional embodiment, the desired gene is a candidate gene in cotton fiber development. In a further embodiment, the desired gene is a candidate gene in cotton fiber initiantion, elongation, secondary wall deposition, maturation or seed development. In an additional embodiment, the desired gene is as described above. The results shown herein demonstrate that the VIGS system of the present invention can efficiently suppress targeted host genes and can be used as a rapid means to assay the role of candidate genes, as well as to study the role of regulatory genes, such a transcription factor genes or the role of genes involved in the small RNA biogenesis pathways. The VIGS assay described herein offers a means to test the function of cotton gene sequences in a homologous system. Using a normalized cDNA library it is possible to conduct large scale screens of gene function with the VIGS system of the present invention.

The host plant can be *Gossypium hirsutum* (upland cotton, tetraploid), but as demonstrated herein, the invention is not limited to this species. Thus, the host plant can also be *Gossypium barbadense* (tetraploid), *Gossypium arboreium* (diploid), and *Gossypium herbaceum* (diploid) and other natural *Gossypium* species and all commercial cotton varieties and germplasms including germplasms derived from intra-species and inter-species crossings.

Once the function of a cotton gene or cotton genes has been characterized, transgenic plants can be prepared using conventional techniques to alter expression patterns of the gene or genes. Alternatively, plants transiently expressing a gene or genes can be prepared as described herein.

The DNA that is inserted (the DNA of interest) into plants of the genera *Gossypium* is not critical to the transformation process. Generally the DNA that is introduced into a plant is part of a construct. The DNA may be a gene of interest, e.g., a coding sequence for a protein, or it may be a sequence that is capable of regulating expression of a gene, such as an antisense sequence, a sense suppression sequence, a shRNA, a precursor miRNA or a miRNA sequence. The construct typically includes regulatory regions operatively linked to the 5' side of the DNA of interest and/or to the 3' side of the DNA of interest. A cassette containing all of these elements is also referred to herein as an expression cassette. The expression cassettes may additionally contain 5' leader sequences in the expression cassette construct. The regulatory regions (i.e., promoters, transcriptional regulatory regions, and translational termination regions) and/or the polynucleotide encoding a signal anchor may be native/analogous to the host cell or to each other. Alternatively, the regulatory regions and/or the polynucleotide encoding a signal anchor may be heterologous to the host cell or to each other. See, U.S. Pat. No. 7,205,453 and U.S. Patent Application Publication Nos. 2006/0218670 and 2006/0248616. The expression cassette may additionally contain selectable marker genes. See, U.S. Pat. No. 7,205,453 and U.S. Patent Application Publication Nos. 2006/0218670 and 2006/0248616.

Generally, the expression cassette will comprise a selectable marker gene for the selection of transformed cells. Selectable marker genes are utilized for the selection of transformed cells or tissues. Usually, the plant selectable marker gene will encode antibiotic resistance, with suitable genes including at least one set of genes coding for resistance to the antibiotic spectinomycin, the streptomycin phosphotransferase (spt) gene coding for streptomycin resistance, the neomycin phosphotransferase (nptII) gene encoding kanamycin or geneticin resistance, the hygromycin phosphotransferase (hpt or aphiv) gene encoding resistance to hygromycin, acetolactate synthase (als) genes. Alternatively, the plant selectable marker gene will encode herbicide resistance such as resistance to the sulfonylurea-type herbicides, glufosinate, glyphosate, ammonium, bromoxynil, imidazolinones, and 2,4-dichlorophenoxyacetate (2,4-D), including genes coding for resistance to herbicides which act to inhibit the action of glutamine synthase such as phosphinothricin or basta (e.g., the bar gene). See generally, WO 02/36782, U.S. Pat. No. 7,205,453 and U.S. Patent Application Publication Nos. 2006/0248616 and 2007/0143880, and those references cited therein. This list of selectable marker genes is not meant to be limiting. Any selectable marker gene can be used.

A number of promoters can be used in the practice of the invention. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 (WO 99/48338 and U.S. Pat. No. 6,072,050); the core CaMV$^{35S}$ promoter (Odell et al., 1985); rice actin (McElroy et al., 1990); ubiquitin (Christensen and Quail, 1989 and Christensen et al., 1992); pEMU (Last et al., 1991); MAS (Velten et al., 1984); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; and 5,608,142.

Other promoters include inducible promoters, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. Other promoters include those that are expressed locally at or near the site of pathogen infection. In further embodiments, the promoter may be a wound-inducible promoter. In other embodiments, chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. In addition, tissue-preferred promoters can be utilized to target enhanced expression of a polynucleotide of interest within a particular plant tissue. Each of these promoters are described in U.S. Pat. Nos. 6,506, 962, 6,575,814, 6,972,349 and 7,301,069 and in U.S. Patent Application Publication Nos. 2007/0061917 and 2007/0143880.

Where appropriate, the DNA of interest may be optimized for increased expression in the transformed plant. That is, the coding sequences can be synthesized using plant-preferred codons for improved expression. Methods are available in the art for synthesizing plant-preferred genes. See, for example, U.S. Pat. Nos. 5,380,831, 5,436,391, and 7,205,453 and U.S. Patent Application Publication Nos. 2006/0218670 and 2006/0248616.

The use of dsRNA for gene silencing as well as the design of siRNA or shRNA molecules for use in gene silencing in plants is well known in the art. See, for example, U.S. Patent Application Publication Nos. 2004/0192626, 2004/0203145, 2005/0026278, 2005/0186586, 2005/0244858, 2006/0212950, 2007/0259827, 2007/0265220, 2007/0269815, 20080269474 and 2008/0318896. The use of miRNA for gene silencing as well as the design of precursor miRNA or miRNA molecules for use in gene silencing in plants is well known in the art. See, for example, U.S. Patent Application Publication Nos. 2006/0130176, 2006/0218673, 2007/0083947, 2007/0130653, 2007/0154896 and 2008/0313773.

In certain embodiments, the invention also provides plant products obtained from transgenic plants of the invention. The term "plant product" is intended to include anything that may be obtained from a particular plant, including, for example, fruits, seeds, pollen, ovules, plant embryos, oils, juices, waxes, proteins, lipids, fatty acids, vitamins, plant tissues in whole or in part, (e.g. roots, leaves, stems, flowers, boll, fruit, bark), cells, cell suspensions, tubers and stolons.

In a further aspect, the present invention provides a transient expression vector and method for transiently expressing genes in cotton plants. In accordance with this aspect, the transient expression vector comprises a TRV RNA2 sequence and at least one copy of a strong subgenomic promoter and optionally a nucleic acid comprising a first sequence of interest. In one embodiment, the subgenomic promoter is one that is recognized by the replicase of TRV. In another embodiment, the subgenomic promoter is a strong coat protein subgenomic promoter. In a further embodiment, the subgenomic promoter is derived from a Tobravirus other than TRV. In one embodiment, the subgenomic promoter is a synthetic pea early browning virus (PEBV) subgenomic promoter. In another embodiment, the subgenomic promoter is a Pepper ringspot virus (PepRSV) coat protein subgenomic promoter. The nucleic acid of interest for transient expression in cotton is inserted downstream of the subgenomic promoter and is operably linked to this promoter. In another embodiment, the nucleic acid comprises two or more sequences of interest each to be expressed in a cotton plant. In a further embodiment, the vector comprises two or more nucleic acids each comprising a sequence of interest to be expressed in a cotton plant and each operably linked to a separate copy of the subgenomic promoter.

The sequence of interest to be transiently expressed in plants of the genera Gossypium is not critical to the transient expression method of the present invention. The sequence of interest may be a gene of interest, e.g., a coding sequence for a protein, or it may be a sequence that is capable of regulating expression of a gene, such as an antisense sequence, a sense suppression sequence or a micro-RNA (miRNA) sequence. The sequence of interest typically includes regulatory regions operatively linked to the 5' side of the sequence of interest and/or to the 3' side of the sequence of interest in addition to the subgenomic promoter. The sequence of interest may additionally contain operably linked 5' leader sequences in the transient expression vector. The regulatory regions (i.e., transcriptional regulatory regions, and translational termination regions) and/or the polynucleotide encoding a signal anchor may be native/analogous to the host cell or to each other. Alternatively, the regulatory regions and/or the polynucleotide encoding a signal anchor may be heterologous to the host cell or to each other. See, U.S. Pat. No. 7,205,453 and U.S. Patent Application Publication Nos. 2006/0218670 and 2006/0248616.

Where appropriate, the sequence of interest may be optimized for increased transient expression in the plant. That is, the coding sequences can be synthesized using plant-preferred codons for improved expression. Methods are available in the art for synthesizing plant-preferred genes. See, for example, U.S. Pat. Nos. 5,380,831, 5,436,391, and 7,205,453 and U.S. Patent Application Publication Nos. 2006/0218670 and 2006/0248616.

In one embodiment, the sequence of interest is (a) a coding sequence of a gene to be expressed in cotton, such as a *Bacillus thuringiensis* insecticidal toxin protein (BT) and a *Flower locus* T (FT) gene to shorten flowing time or (b) a sequence of a gene to down regulate, such as a candidate transcription factor gene, a candidate gene in smRNA biosynthesis, a candidate gene in photohermone signal pathway, a candidate gene invoved in abotic and biotic stress resistance, a candidate gene in fatty acid biosynthesis a candidate gene in cotton fiber development a candidate gene in cotton trichome related and a candidate gene in secondary metabolite biosynthesis.

In accordance with this aspect, the method for transiently expressing a nucleic acid of interest in cotton tissue comprises:

(a) inserting a nucleic acid comprising a first sequence of interest to be expressed in a cotton plant into a transient expression vector comprising a tobacco rattle virus (TRV) RNA2 sequence and at least one copy of a subgenomic promoter to produce a TRV RNA2 expression vector, wherein the nucleic acid is operably linked to the subgenomic promoter;

(b) preparing a mixed culture of *Agrobacterium* comprising *Agrobacterium* containing a vector comprising a TRV RNA1 sequence and *Agrobacterium* containing the TRV RNA2 expression vector;

(c) introducing the mixed culture of *Agrobacterium* into plant tissue of cotton; and (d) growing the infected plant tissue for a sufficient time to transiently express the desired gene.

In one embodiment of this aspect, the plant tissue is cotton seedlings. In another embodiment of this aspect, the plant tissue is cotton ovules. In an additional embodiment of this aspect, the plant tissue is cotton plants. In a further embodiment of this aspect, the plant tissue is cotton fiber. In a still further embodiment, a cotton plant or seedling is infected and the virus spreads through the cotton tissue, such that VIGS occurs in all tissue of the infected cotton plant or seedling.

In one embodiment, the vector comprising TRV RNA2 and the vector comprising TRV RNA1 are synthetic plant vectors. In another embodiment, the first sequence of interest is the sequence of a sense strand of a gene. In an additional embodiment, the first sequence of interest is the sequence of an antisense strand of a gene. In a further embodiment, the first sequence encodes a precursor miRNA or a miRNA. As shown herein, the transient expression vector of the present invention can be used to rapidly transiently express nucleic acids of interest in cotton plants. In another embodiment, the nucleic acid further comprises a second sequence of interest to be expressed in cotton plants. In an additional embodiment, the nucleic acid comprises more than two sequences of interest to be expressed in cotton plants. In another embodiment, two or more nucleic acids are inserted into the transient expression vector. In this embodiment each nucleic acid comprises a sequence of interest and each is operably linked to a separate copy of the subgenomic promoter. The sequences of interest in the two or more nucleic acids may be the same or different. The sequences of interest include those described above.

The host plant can be *Gossypium hirsutum* (upland cotton, tetraploid), but as demonstrated herein, the invention is not limited to this species. Thus, the host plant can also be *Gossypium barbadense* (tetraploid), *Gossypium arboreium* (diploid), and *Gossypium herbaceum* (diploid) and other natural *Gossypium* species and all commercial cotton varieties and germplasms including germplasms derived from intra-species and inter-species crossings.

In certain embodiments, the invention also provides plant products obtained from transiently expressing plants of the invention. The term "plant product" is intended to include anything that may be obtained from a particular plant, including, for example, fruits, seeds, pollen, ovules, plant embryos, oils, juices, waxes, proteins, lipids, fatty acids, vitamins, plant tissues in whole or in part, (e.g. roots, leaves, stems, flowers, boll, fruit, bark), cells, cell suspensions, tubers and stolons.

In another aspect, the present invention provides a modified TRV RNA1 vector with improved initiation of transcription. There are many reasons that cause RNA viral vectors to have difficulties in initiation of transcription. First is the non-optimized genome sequence that might be improperly recognized by the RNA processing machinery such as cryptic splice sites and thymine-rich, putative intron sequences embedded in RNA genomes. Second, TRV RNA1 viral vector encode very large transcripts about 7.0 kilonucleotides, a size is about 3-4 fold of average plant genes size (1-2 Kb). In nature, plant genes often contain huge numbers of introns that facilitate processing and export of the pre-mRNA from the nucleus. In the agroinfiltration-based VIGS and transient expression systems, pre-mRNA transcripts made in plant nucleus from viral constructs may not be efficiently recognized or proper processing without intron sequences.

In accordance with this aspect, the modified TRV RNA1 vector comprises a TRV RNA1 sequence into which at least one intron has been inserted. Additional introns can be inserted to make the viral transcript easier to be recognized by the host nuclear pre-mRNA processing and export machinery, therefore to increase the percentage of plant cells in which viral replication could occur, but also the efficiency by which an infection could be initiated. Theoretically, any plant intron can be used. In one embodiment the intron ranges is in size from about 100 nucleotides to about 400 nucleotides. In another embodiment the intron is derived from *Arabidopsis thaliana*. Intron insertion site can be the consensus AG/GT sequences in the TRV1 genome or a sequence that has been mutated with silent nucleotide substitutions to match the consensus sequence. This modified TRV RNA1 vector can be used in place of the vector containing TRV RNA1 in any of the above methods.

The host plant can be *Gossypium hirsutum* (upland cotton, tetraploid), but as demonstrated herein, the invention is not limited to this species. Thus, the host plant can also be *Gossypium barbadense* (tetraploid), *Gossypium arboreium* (diploid), and *Gossypium herbaceum* (diploid) and other natural *Gossypium* species and all commercial cotton varieties and germplasms including germplasms derived from intra-species and inter-species crossings.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, N.Y.); Sambrook et al., 1989, *Molecular Cloning*, 2nd Ed. (Cold Spring Harbor Laboratory Press, Cold Spring Harbor, N.Y.); Sambrook and Russell, 2001, *Molecular Cloning*, 3rd Ed. (Cold Spring Harbor Laboratory Press, Cold Spring Harbor, N.Y.); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring. Harbor Laboratory Press, Cold Spring Harbor, N.Y.); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference* (RNAi): *The Nuts & Bolts of siRNA Technology*, DNA Press, 2003; Gott, *RNA Interference, Editing, and Modification: Methods and Protocols* (*Methods in Molecular Biology*), Human Press, Totowa, N.J., 2004; Sohail, *Gene Silencing by RNA Interference: Technology and Application*, CRC, 2004.

EXAMPLES

The present invention is described by reference to the following Examples, which is offered by way of illustration and is not intended to limit the invention in any manner. Standard techniques well known in the art or the techniques specifically described below were utilized.

Example 1

Experimental Procedures for Examples 2-6

Cotton seedlings: Cotton seeds were propagated and germinated in a greenhouse. Four to 14 day old seedlings carrying 2-3 true leaves were used for VIGS assays. Younger seedlings with only cotyledons can also be used for VIGS assays.

Synthetic TRV RNA1 expression vector: Synthetic TRV1 vector full length (7756 bp) sequence including: SphI site, T-DNA right border sequence (152 bp), the duplicated cauliflower mosaic virus (CaMV) 35S enhancer region (752 bp) (Shi et al., 1997) the TRV Ppk20 strain RNA1 (6791 bp), Subterranean Clover Mottle Virus satellite RNA ribozyme sequence (46 bp) and SmaI site sequence. This full length sequence was divided into two parts by an endogenous SalI site. The two parts were separately synthesized and cloned into pGH vector to give two vectors pGH-YeJ-V1-1 and pGH-YeJ-V1-2. The synthetic TRV RNA1 fragments, V1-1, released from pGH-YeJ-V1-1 by treatment with SphI and SalI enzymes, and V1-2, released from pGH-YeJ-V1-2 by treatment with SalI and SmaI enzymes, were linked with the pBI121 (GenBank accession number: AF485783) vector treated with SphI and EcoICRI enzymes. The new synthetic TRV RNA1 vector was named psTRV1001 (also referred to as psTRV1 herein). The sequence of the synthetic psTRV1001 is set forth in SEQ ID NO:1. The synthetic TRV RNA1 sequence is the same as the published TRV RNA1 sequence.

Synthetic TRV RNA2 expression vector: Synthetic TRV2 vector full length (2915 bp) sequence including: HindIII site, the duplicated cauliflower mosaic virus (CaMV) 35S enhancer region (752 bp) (Shi et al., 1997) the TRV strain ppk20 RNA2 5'-sequence (1639 bp), multiple cloning site (61 bp), the TRV strain ppk20 RNA2 3'-sequence (396 bp), HpaI site. The full length sequence was synthesized and cloned into pGH vector give pGH-YeJ-V2. The synthetic TRV RNA2 fragment V2 was linked into the pCAMBIA0390 (GenBank accession number: AF234291) by HindIII and HpaI sites. The new synthetic TRV RNA2 vector was named psTRV2001 (also referred to as psTRV2 herein). The sequence of the synthetic sTRV2 is set forth in SEQ ID NO:2. The synthetic TRV RNA2 sequence is the same as the published TRV RNA2 sequence. The sequence of the synthetic psTRV2001 is set forth in SEQ ID NO:82.

Fluorescent Protein (GFP) expression vector pK20GFPc was PCR amplified with primers GFP-F (5'-TTATAGGTAC-CATGGCTAGCAAAGGAGAAGAAC-3' (SEQ ID NO:25)) and GFP-R (5'-CCTAAGAGCTCTTAATCCATGCCATGT-GTAATCCC-3' (SEQ ID NO:26) and the GFP gene was inserted into the NcoI and BamHI sites in psTRV2100. This vector was named psTRV2:GFP.

Figure 2:
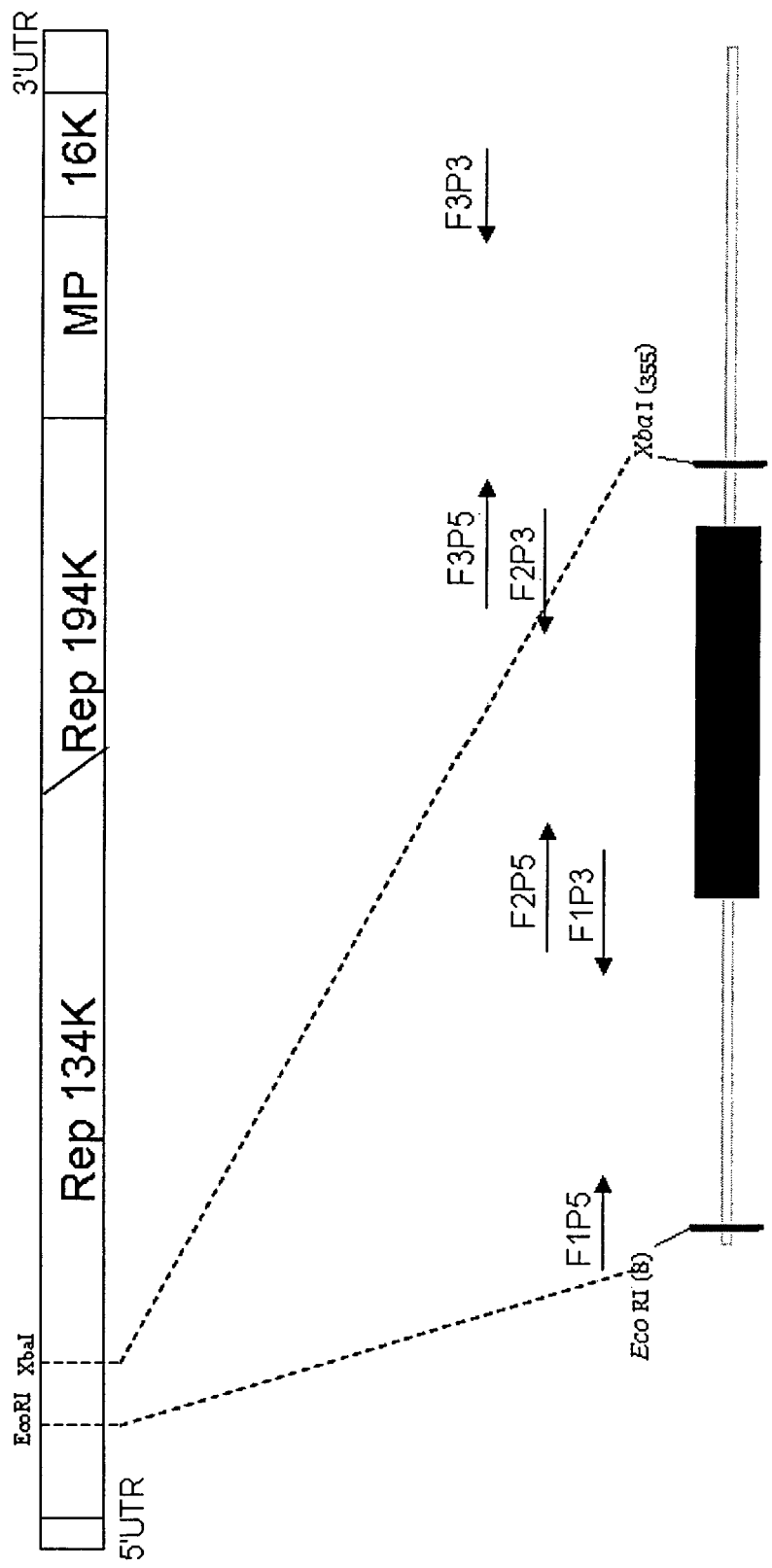
FIG. 2 shows schematic drawing of TRV RNA1 modification with one intron insertion.

Modified sTRV1 vector: A PCR based strategy was used to introduce a plant intron from *A. thaliana* actin1 (intron 2, GenBank Accession NO U27981, position 1957-2111 bp) into TRV RNA1 genome. Three fragments were amplified based on three primer pairs: F1P5 and F1P3 for F1, F2P5 and F2P3 for F2, F3P5 and F3P3 for F3. The sequences of these primer pairs are set forth in Table 1. The locations of the primers with respect to this intron are shown in FIG. 2. Overlapping PCR was used to get a longer DNA fragment with F1P5 and F3P3 in the second round PCR amplification. The PCR product was further digested with EcoRI and XbaI and inserted into the psTRV1001 vector. The intron-containing psTRV1 was named psTRV1001-intron (also referred to as psTRV1-intron herein). The sequence of the inserted intron is gtaag-tacatttccataacgttccatcgtcattgattcttcattagtatgcgtttatgaagctttt-tcaatttaattctctttggtagatctt aagattcctctgtttcttgcaaaataaa-gggttcaattatgctaatattttttatatcaattttgacag (SEQ ID NO:27).

TABLE 1

Gene Primers for Synthesis of Intron

| Primer | Sequence (5'→ 3') | SEQ ID NO: | Location in psTRV1001 |
|---|---|---|---|
| F1P5 | cctgaattcaatatcgtgtttaaagacg | 4 | 10764-10791 |
| F1P3 | ataattctagaggggggactgtttctggtggcatg | 5 | |
| F2P5 | cgttttgggtaactagaggtaagtacatttccataacgttcc | 6 | |
| F2P3 | aatgaatccttttctcacctgtcaaaattgatataaaaaata | 7 | |
| F3P5 | ttatatcaattttgacaggtgagaaaaggattcattcctgttg | 8 | |
| F3P3 | cctacatgtacaaccctgatatgtatt | 9 | 11115-11141 |

Synthetic TRV transient expression vector: For construction of the transient expression vector psTRV2100, a synthetic pea early browning virus (PEBV) subgenomic promoter (237 bp, SEQ ID NO:3) polynucleotide including an EcoRI site at its 5' end and a NcoI site at its 3' end was inserted into the multiple cloning site in the psTRV2001 vector. Green Gene cloning and VIGS vector cloning: Candidate genes were amplified by PCR from cDNA products of *Gossypium hirsutum* leaf samples, and cloned into the XbaI and BamHI sites of the synthetic vector psTRV2001. The primers used in cloning the genes are set forth in Table 2, which also includes reference to the sequence of the cloned gene.

TABLE 2

Gene Primers and Gene Sequences

| Gene | Primers: Sequence (5'→ 3') | SEQ ID NO: | Cloned Gene |
|---|---|---|---|
| CAD | F: ATTATCTAGAAAATTGAAAGAAGAAGTGAGG | 10 | 604 bp, |
|  | R: TATTGGATCCCAGGAAGTTCATCTATGCAT | 11 | GenBank: AY800106 |
| AS1 | F: ATAATTCTAGAGGGGGACTGTTTCTGGTGGCATG | 12 | 418 bp |
|  | R: CCGTAAGGGATCCCTTCTTGATACC | 13 | |

TABLE 2-continued

Gene Primers and Gene Sequences

| Gene | Primers: Sequence (5'→ 3') | SEQ ID NO: | Cloned Gene |
|---|---|---|---|
| AGO1 | F: ATAATTCTAGAGGGGGACTGTTTCTGGTGGCATG<br>R: TACCTGGATCCCCACTTATCATTGATCCACTGTCTG | 14<br>15 | 583 bp |
| CH42 | F: AAATATCTAGAGGTGCTACTGAAGATAGGGTCTGTGG<br>R: GACTCCAAAGGATCCTTGCGAAGACG | 54<br>55 | 653 bp |
| PDS | F: TTATTTCTAGAGCACGAGCTTCCTTTGTATCTGCC<br>R: TCCTAGGATCCAATATTGGTGTATGACCTGCATCCGC | 56<br>57 | 479 bp |
| ANS | F: AATAATCTAGAAGAGAAGTATGCCAACGACCA<br>R: GCTATGGATCCGGAGGGAACAGTGGAGGTTCGG | 58<br>59 | 663 |
| ANR | F: AATAATCTAGACTTGTAACACTACAAGAGTTGGG<br>R: GAGCTGGATCCGGGCTCGGCATACGTCTTCCAC | 60<br>61 | 595 |
| AN | F: AATAATCTAGACACTCATCAACCATATCCAGTACC<br>R: GTCCTGGATCCACAATTCCCAACACTAGTCCTCGG | 62<br>63 | 621 bp |
| KTN | F: ATGGCGGATCCTGTTGGAAATTCGCTAGCTGG<br>R: GTCCTGGATCCATACTCAGGCATCCATAGAGGAAG | 64<br>65 | 675 bp |

*Agrobacterium* infiltration: Synthetic psTRV vectors and their derivatives were introduced into *Agrobacterium* strain AGL1 by electroporation. A 3 ml culture was grown for 24 hr at 28° C. in 50 mg/L kanamycin and 25 mg/L rifampicin. On the following day, the culture was inoculated into LB medium containing 50 mg/L kanamycin, 10 mM 2-(N-morpholino) ethanesulfonic acid (MES) and 20 µM acetosyringone and grown overnight in a 28° C. shaker. Agrobacterial cells were collected by centrifugation and resuspended in MMA solution (10 mM MES, 10 mM $MgCl_2$, 200 µM acetosyringone) to a final $OD_{600}$ of 1.5. The agrobacterial suspension was left at room temperature for 3-4 hr without shaking. Before infiltration, *Agrobacterium* culture containing the pTRV1/psTRV1 or pTRV2/psTRV2 vectors was mixed in a 1:1 ratio. Cotton plants were infiltrated with cultures either by syringe infiltration or by vacuum infiltration. For syringe infiltration, agrobacterial-inocula were delivered into the underside of two or three youngest fully-expanded leaf using a 1 ml needleless syringe. For vacuum infiltration, whole plants were submerged into agrobacterial-inocula and subjected to 80-90 kPa vacuum for 5 min, and then quickly releasing the vacuum, letting the inoculum rapidly enter plant tissues. All data described below were obtained by vacuum infiltration. However, syringe infiltration can also be used, but it is more time costly than vacuum infiltration. The silencing effect obtained with vacuum infiltration is better than that obtained with syringe infiltration. After infiltration, excess agrobacterial cell suspension was used to drench the root system of infiltrated plants. Infiltrated plants were grown in a growth chamber at 25° C. with 16 hr light/8 hr dark photoperiod cycle. The same method was also used in experiments testing VIGS in putative host plants.

Determination of Gossypol and related terpenoids by high-performance liquid chromatography: Levels of gossypol and related terpenoids in cottonseed and other tissues were determined by using HPLC-based methods, as described. 100 mg fresh cotton leaf samples were homogenized in liquid nitrogen with mortar and pestle and 1 ml of Solvent 1 (acetonitrile: water:phosphoric acetic acid=80:20:0.1(V/V/V), pH=2.8-2.9) was added to samples. Plant tissue was further broken with MIXER MILL MM300 (Qiagen, Germany). The suspension was centrifuged at 3000 g for 10 min. A 50 µl fraction of the extract was analyzed on an Agilent 1200 HPLC system equipped with autoinjector. Samples were isocratically eluted from a Synergi 4 µm Fusion-RP 80A (Phenomenx) column maintained at 40° C. The mobile phase was ethanol:methanol:isopropyl alcohol:acetonitrile:water:ethyl acetate:dimethyl-formamide:phosphoric acid=16.7:4.6:12.1:20.2:37.4: 3.8:5.1:0.1 (Stipanovic et al., 1988). Solvent flow rate was 1.0 mL $min^{-1}$ and total run time was 45 min. The signal was monitored at 272 nm. Data collection and analysis were performed on Agilent Chemstation software. tert-butylanthraquinone was used as an internal standard.

GFP imaging and quantitative fluorescence analysis. To visually detect GFP fluorescence on leaf patches and whole plants, a hand-held 100 W, long-wave UV lamp (UV Products, Upland, Calif.) was used, and fluorescence images were taken using a Nikon Coolpix 995 digital camera (Tokyo, Japan) mounted with UV and Kenko yellow lens (Tokyo, Japan).

Antibodies and protein gel blot analysis: Total plant proteins were separated by 12% sodium dodecyl sulfate-polyacrylamide gel electrophoresis. Mouse monoclonal IgG against GFP protein was used for primary antibody. ECL peroxidase conjugated donkey anti-rabbit immunoglobulin G was used as a secondary antibody. Immunoreactive bands were visualized using ECL Western blotting Detection Reagents (GE healthcare). Coomassie blue-stained rbcL band was used as a loading control.

Scanning Electron Microscope (SEM). Fresh leaves were fixed with a tape inside a sample chamber, following freezing in liquid N2. Images were collected using a SEM (JSM-6360LV, JEOL, USA).

RNA extraction and analysis. 100 mg leaf tissues was ground in liquid N2 and extracted with plant RNA purification reagent (Invitrogen). RNA concentration was measured by Nanodrop (Thermo, USA). M-MLV reverse transcriptase (Promega, USA) was used for reverse transcription reactions. Real-time PCR was performed with Power SYBR® Green PCR Master (Applied Biosystems, USA) and run in ABI7900HT using the gene specific primers set forth in Table 3. All samples were run in triplicates and data was analyzed with RQ manager at a pre-set Ct value (Applied Biosystems, USA). The Jatropha rbcL mRNA served as an internal control. Ct values included in the analyses were based on 3 biological replicates, with three technical replicates for each biological sample. Standard deviation was calculated based on 3 biological replicates.

TABLE 3

Primers Used in Gene-Specific Real-Time PCR Analysis

| Genes | Primer (SEQ ID NO:) | | |
|---|---|---|---|
| CH42 | 5'-AAGGCAGAGCAAGAGAAG-3' | (forward) | (66) |
| | 5'-TCTATTAGTGACAATATC-3' | (reverse) | (67) |
| PDS | 5'-TTTGTATCTGCCCAACCC-3' | (forward) | (68) |
| | 5'-TATTGGTGTATGACCTGC-3' | (reverse) | (69) |
| ANS | 5'-GTGGGTGACCGCTAAATG-3' | (forward) | (70) |
| | 5'-GGCTCACAGAAAACTGCC-3' | (reverse) | (71) |
| ANR | 5'-TGCAGTGCTGTCAATACC-3' | (forward) | (72) |
| | 5'-CTCTGAGGAAATGATCAAC-3' | (reverse) | (73) |
| AN | 5'-CGACTCCGCCTTAGCTGCTGAC-3' | (forward) | (74) |
| | 5-GAACTGATCCAAGCCAACCGG-3' | (reverse) | (75) |

Example 2

Development of a VIGS System in Cotton Using a Gene involved in Terpenoid Biosysnthesis as a Marker Gene This example describes the construction of a tobacco rattle virus (TRV) based vector and its use for gene silencing in cotton. Virus induced gene silencing (VIGS) is initiated when a recombinant virus carrying a sequence from a host gene infects the plant. The endogenous gene transcripts with sequence homology to the insert in the VIGS vector are degraded by a post-transcriptional gene silencing mechanism (PTGS) (Baulcombe, 2004).

Gossypol and related terpenoids are present throughout the cotton plant in the glands of foliage, floral organs, and bolls, as well as in the roots. Gossypol and other sesquiterpenoids are derived from (+)-δ-cadinene. The gene silencing efficiency of the TRV VIGS clones to suppress cad gene expression was assessed in cotton. The enzyme encoded by the δ-cadinene synthase gene is responsible for the first committed step involving the cyclization of farnesyl diphosphate to (+)-δ-cadinene. When this gene is silenced, the biosynthesis of gossypol and other sesquiterpenoids will be all disrupted. Sunilkumar et al. (2006) have successfully used cad gene RNAi to disrupt gossypol biosynthesis in cotton seed by stable transformation. In addition, these terpenoids are induced in response to microbial infections. These compounds protect the plant from both insects and pathogens.

In order to study the role of cad in cotton pest resistance and development roles, we first cloned cotton cad (SEQ ID NO:16) by PCR with primers (SEQ ID NOs:10 and 11) based on full length cDNA sequences (GenBank accession number: AY800106) and inserted into the psTRV2 vector to give psTRV2:CAD. A mixture of *Agrobacterium* cultures containing psTRV1 and psTRV2:CAD vector was infiltrated into cotton plants using vacuum infiltration.

Figure 3:
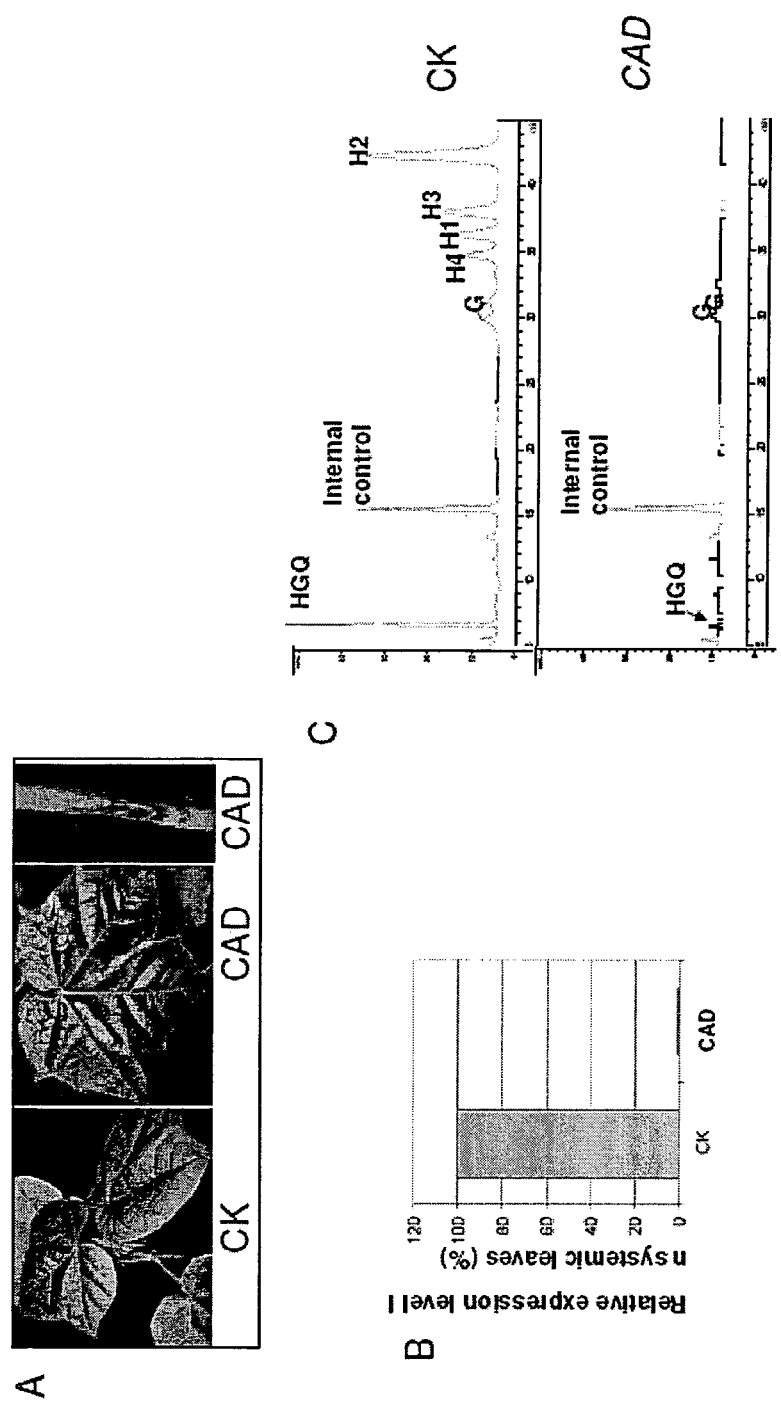
FIGS. 3A-3C show the silencing of the Gossypol biosynthesis gene.

At 14 days post infection (dpi) the stem in infected cotton plants turned to brownish and became brittle and leaves begin to wither. There is no obvious phenotype in upper leaves of psTRV2:CAD treated plants (FIG. 3A). Brownish necrosis and withering were seen in most of the psTRV2:CAD plants bark at 25 dpi whereas no obvious phenotypes can be seen in the vector only control plants (FIG. 3A). Most of the psTRV2:CAD plants were dead after 35 dpi (25/30 plant dead), which indicates that VIGS in cotton works with high efficiency and in a robust and reliable manner.

We performed quantitative realtime PCR, using total RNA extracted from leaves of treated plants to confirm the VIGS of the CAD gene at the molecular and the results are shown in FIG. 3B. CAD RNA accumulation in the upper leaves of psTRV2:CAD infected plant was much lower than that of plants infected with the empty sTRV2 vector and there is only 0.2% of CAD RNA was left in CAD treated plants.

High-performance liquid chromatography (HPLC) was used to examine gossypol and related sesquiterpenoids from control and silenced cotton leaves. As gossypol is very sensitive to air oxidation and readily forms acetals in alcoholic colutions, we modified the extraction and analysis methods were modified (for details see Example 1) in order to achieve accurate and reproducible results. As expected, HPLC data showed that the gossypol and related sesquiterpenoids levels were reduced to almost zero, while control plants maintain high level of these chemical components (FIG. 3C).

These results and the phenotypic data in CAD silenced plants indicated that the synthetic sTRV VIGS systems could be used to induce silencing of desirable endogenous cotton genes with high efficiency and in a robust and reliable style.

Currently, complete sequencing of cotton genomes is just beginning. Meanwhile, an ever-expanding set of *Gossypium* EST sequences (about 400,000 now) and derived unigene sets from different libraries constructed from a variety of tissues and organs under a range of conditions are accessible on the web. These expressed sequence tags (ESTs) provide a wealth of information for functional genomics study of cotton. Therefore, the VIGS assay described here offers a means to test the function of cotton gene sequences in a homologous system. Using a normalized cDNA library it is possible to conduct large scale screens of gene function with the sTRV based VIGS system.

Example 3

Development of a VIGS System in Cotton Using CH42 and PDS as Marker Genes

This example describes the construction of additional tobacco rattle virus (TRV) based vectors and their use for virus induced gene silencing in cotton.

We assessed the gene silencing efficiency of the synthetic TRV (sTRV) clones to suppress CH42 gene expression in *Gossypium hirsutum*. The enzyme encoded by the CH42 gene is responsible for adding magnesium into the porphyrin ring during chlorophyll biosynthesis. When this gene is silenced, chlorophyll synthesis is blocked and consequently leaves lose their green color but appear yellow instead owing to the presence of carotenoids.

To amplify the CH42 homolog from *Gossypium hirsutum*, a putative EST sequence was identified by using *Arabidopsis* CH42 gene (NM 117962) as a seed sequence to BLAST against the whole EST sequences of GenBank. One EST encoded the putative CH42 protein in cotton was identified. PCR primers (SEQ ID NOs: 54 and 55) were designed to amplify a 653-bp CH42 cDNA of *G. hirsutum* by PCR, and the CH42 fragment (SEQ ID NO:76) was inserted into the psTRV2 MCS site to give psTRV2:CH42. The sequence of CH42 was verified by sequencing.

Figure 4:
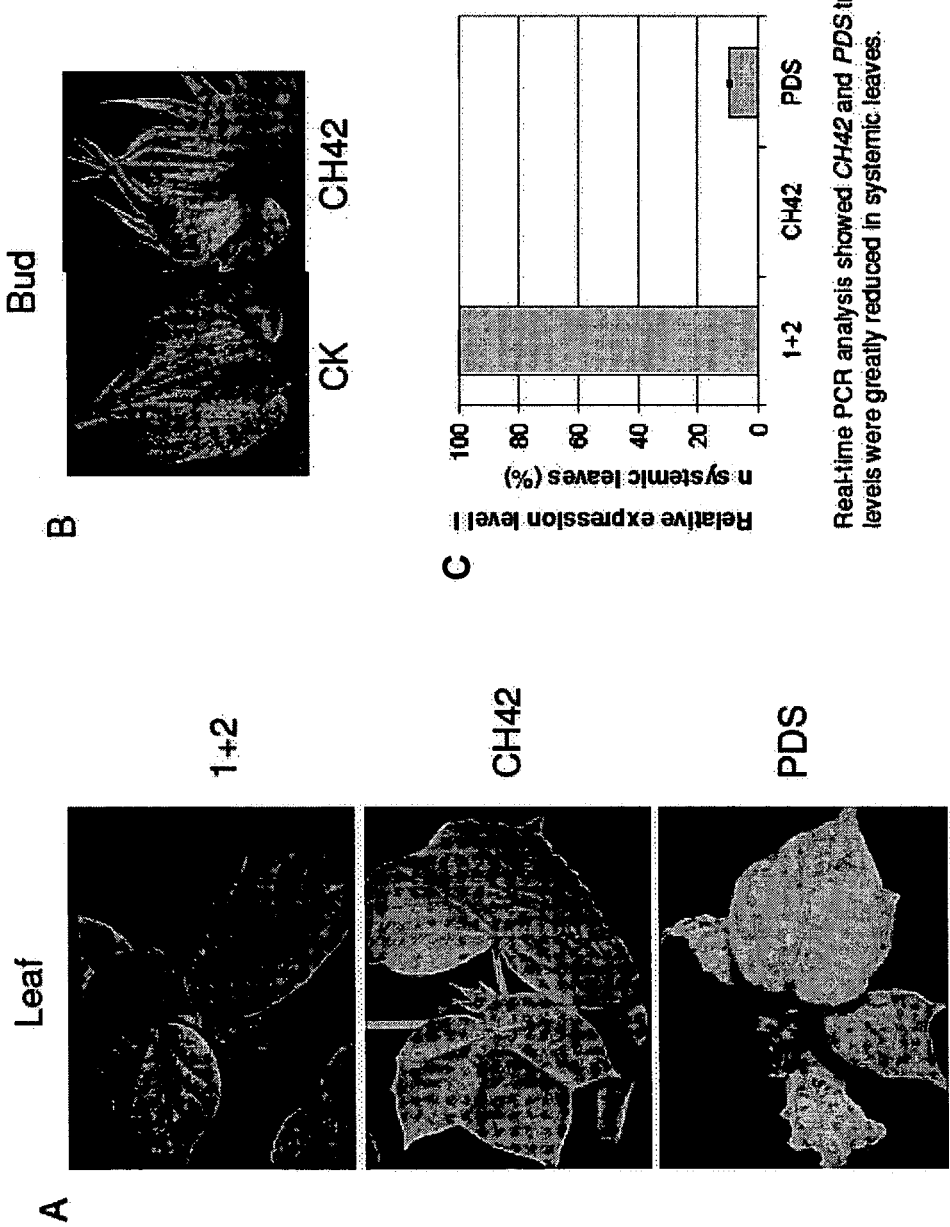
FIGS. 4A-C show the VIGS effect on one chlorophyll biosynthesis gene magensium chelatase CH42 gene and the effect of carotene biosynthesis gene phytoene desaturase (PDS) gene. Cultures of *Agrobacterium tumefaciens* strains carrying psTRV1 or psTRV2 (Vector control 1+2 (FIG. 4A) or check (FIG. 4B), psTRV2:CH42 (FIGS. 2A and 2B), psTRV2:PDS (FIG. 2A)) were mixed in 1:1 ratio. Mixed culture was vacuum infiltrated into *G. hirsutum* plants at 2-3 leaf stage plants.

Cultures of *Agrobacterium* carrying psTRV1 was mixed with cultures of *Agrobacterium* carrying either psTRV2:

CH42 or psTRV2 vector control. The mixed culture was vacuum-infiltrated into *G. hirsutum* plants with 2-3 true leaves (for details see Example 1). Upper leaves or reproductive organ flower bud of the treated plants were examined for silencing effects (FIGS. 4A and 4B). Uniform silencing of target gene in whole plants were observed in almost all of treated plants and is helpful for high-throughout study and rapid analysis using VIGS since it allows easy sampling and collection of reproducible data. We performed quantitative realtime PCR, using total RNA extracted from plants treated with different sTRV vectors to confirm the VIGS of the CH42 gene at the molecular and the results are shown in FIG. 4C. CH42 RNA accumulation in the upper leaves of psTRV2:CH42 infected plant was much lower than that of plants infected with the empty psTRV2 vector and there is only 0.2% of CH42 RNA was left in CH42 treated plants.

We further chose to silence another marker gene phytoene desaturase (PDS) which encodes a key enzyme involved in carotenoid biosynthesis. Silencing of the PDS gene would inhibit carotenoid biosynthesis leading to chlorophyll photo-oxidation and destruction at high light intensity and resulting in photo-bleached leaves.

To amplify the PDS homolog from *G. hirsutum*, a putative EST sequence was identified by using *Arabidopsis* PDS gene (AY 057669) sequence to BLAST against the whole EST sequences of GenBank. O ne EST encoded the putative PDS protein in cotton was identified. PCR primers (SEQ ID NOs: 56 and 57) were designed to amplify a 479-bp PDS cDNA of *G. hirsutum* by PCR, and the PDS fragment (SEQ ID N0:77) was inserted into the sTRV2 MCS site to give psTRV2:PDS. The sequence of PDS was also verified by sequencing. Cultures of *Agrobacterium* carrying psTRV1 was mixed with cultures of. *Agrobacterium* carrying either psTRV2:PDS or vector control. The mixed culture was vacuum-infiltrated into *G. hirsutum* plants with 2-3 true leaves. Upper leaves of the treated plants were examined for silencing effects (FIG. 4A). We performed quantitative realtime PCR, using total RNA extracted from plants treated with different sTRV vectors to confirm the VIGS of the PDS gene at the molecular and the results are shown in FIG. 4C. PDS RNA accumulation in the upper leaves of psTRV:PDS infected plant was much lower than that of plants infected with the empty sTRV vector and there is only 10% of PDS RNA was left in PDS treated plants.

Example 4

Demonstration of VIGS System in Other Cotton Germplasm

*Gossypium* includes approximately 45 diploid (2n=2x=26) and five tetraploid (2n=4x=52) species, all exhibiting disomic patterns of inheritance. Most modern cotton varieties are forms of *Gossypium hirsutum* (upland cotton, tetraploid), about 95% of annual cotton crop world wide, although three other species are also utilized to a lesser extent, *Gossypium barbadense* (tetraploid), *Gossypium arboreum* (diploid), and *Gossypium herbaceum* (diploid). These three species are also very important genetic resources and offer gene reservoir for special breeding purpose. For example, *G. herbaceum*, with high resistance to biotic and abiotic stresses, can be used as a good start genetic material for interspecies crossings with *G. hirsutum* to improve its resistance to various stresses. Therefore, a species independent method for gene functional analysis in *Gossypium* genus and relative plants is also greatly needed.

Figure 5:
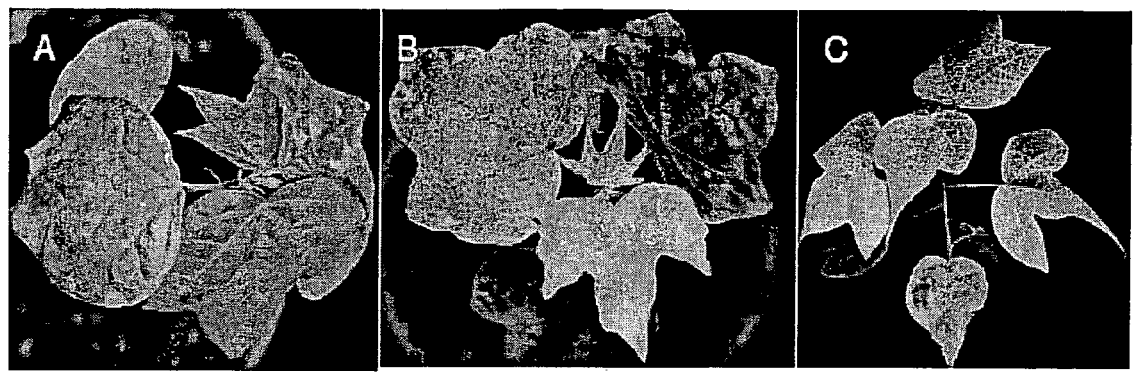
FIGS. 5A-C show show the VIGS system works not only in tetraploid cotton *G. hirsutum*, but also in diploid cotton *Gossypium arboreum* (Fig. A, Fig. B), and *Gossypium herbaceum* (Fig. C).

FIGS. 5A-5C show that the sTRV VIGS system not only works in tetraploid cotton *G. hirsutum*, but also in diploid cotton *Gossypium arboreum* and *Gossypium herbaceum* by demonstrating the silencing effect on one chlorophyll biosynthesis gene magensium chelatase CH42 gene.

Cultures of *Agrobacterium tumefaciens* strains carrying psTRV1 and psTRV2 (FIG. 5A, Vector control 1+2) or psTRV2: CH42 (FIGS. 5B and 5C) were mixed in 1:1 ratio. Mixed culture was vacuum infiltrated into *Gossypium arboreum* and *Gossypium herbaceum* plants at 2-3 leaf stage plants. FIGS. 5A and 5B of cotton leaves were taken at 7 DPI, while FIG. 5C was taken at 14 DPI.

Our data demonstrated that our sTRV VIGS system can work in all tested diploid and tetraploid cotton species, at least in leaves. These data indicated that this sTRV VIGS system can also work for all commercial cotton varieties and germplasms, which are derived from intra-species or inter-species crossing.

Example 5

Using VIGS to Analyze Function of Transcription Factor Genes in Cotton

Transcription factors (TFs)-mediated regulation of mRNA production is a major mode of regulation for plants mounting responses to developmental signals and environmental cues, and transcriptional regulation has been widely studied in model plants, such as *Arabidopsis* and rice. We tested the utility of the TRV-VIGS system for high-throughput analysis TF gene functions.

The *Arabidopsis* ASYMMETRIC LEAVES 1 (AS1) and its orthologs belong to the R2R3 MYB family. They play an evolutionarily conserved role in shoot apical meristem, leaf and fruit development (Sun et al, 2002; Alonso-Cantabrana et al., 2007). AS1 represses class I KNOTTED1-like homeobox (KNOX) gene expression by binding to their promoters (Guo_et al., 2008) and it promotes stem cell function by regulating phytohormone activities (Alonso-Cantabrana et al., 2007). AS1 also negatively regulates inducible resistance against pathogens by selective binding to certain JA-responsive gene promoters (Nurmberg et al., 2007; Yang et al., 2008). By contrast, AS1 is a positive regulator of salicylic acid (SA)-independent extra-cellular defenses against bacterial pathogens (Nurmberg et al., 2007).

In order to study the role of AS1 in cotton development and biotic stress, we first cloned putative cotton AS1 gene homologue. We used the amino acid sequence of *Arabidopsis* AS1 (GenBank accession number: NM129319) to search the GenBank cotton EST database using TBLASTN. Cotton EST clone DT568841, DW499296, ES792898 showed significant homology to *Arabidopsis* AS1. Based on these information, we got a full-length cDNA encoded a putative cotton AS1 protein. The nucleotide sequence of putative cotton AS1 gene is set forth in SEQ ID NO:17. Amino acid sequence analysis of cotton AS1 shows 65.9% identity and 75.8% similarity to *Arabidopsis* AS1 (FIG. 4A). Similar to other AS1 in diverse plant species, this putative cotton AS1 contains a conserved R2R3 MYB domain (shown by dark underline in FIG. 6). The amino acid sequences outside the R2R3 MYB domain are significantly different between this putative cotton AS1 and other AS1 orthologs (FIG. 6). The amino acid of putative cotton AS1 gene is set forth in SEQ ID NO:18.

Figure 7:
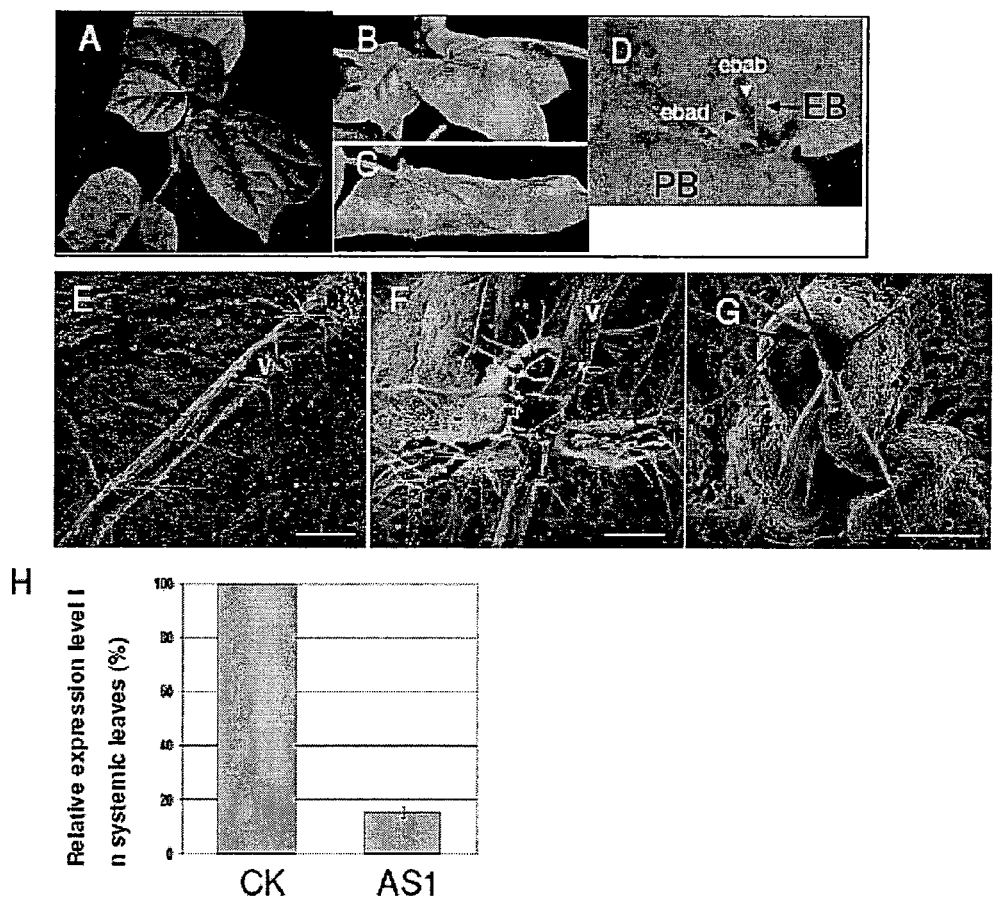
FIGS. 7A-7H show the silencing of the transcription factor AS1.

To amplify the AS1 gene for functional analysis using VIGS in cotton, PCR primers were designed to target a 418 bp fragment which was inserted into psTRV2 to give psTRV2:AS1. A mixture of *Agrobacterium* cultures containing psTRV1 and psTRV2:AS1 vector was vacuum infiltrated into cotton plants. After 18 dpi, obvious phenotypes can be seen in newly emerged leaves. Severe downward curling was the most obvious phenotype from the adaxial side (FIG. 7B and FIG. 7C) of leaves. Leaves silenced in AS1-expression had normal adaxial/abaxial polarity but displayed a specific disruption in the adaxial domain, leading to the formation of ectopic leaf blades on the lateral flanks of vein (FIG. 7D). Ectopic adaxial leaf blades (EB) developed directly from the main vein of primary blade (PB) and showed a fixed polarity (FIG. 7D). These phenotypes of AS1 treated plants were also verified in detail by using scanning electron microscope (FIG. 7F and FIG. 7G). These phenotypes were found in tobacco with AS1 down-regulation (McHale and Koning, 2004). In *Arabidopsis* and tobacco, ectopic expression of KNOX genes leads to production of ectopic adaxial leaf blades (Orr et al., 2000; McHale and Koning, 2004). In Jatropha, a small and woody plant of the Euphorbiaceae family, silencing of AS1-like gene also leads to similar ectopic adacial leaf blade and downward leaf curling (see International patent application No. PCT/SG20009/000481 filed on 16 Dec. 2009 and U.S. provisional patent application No. 61/143,484 filed on 9 Jan. 2009). The phenotypic similarity between this putative cotton AS1 gene silencing plants and other AS1 homologues down-regualtion plants, indicates that this gene is AS1 gene homologue in cotton.

We performed quantitative realtime PCR, using total RNA extracted from leaves of treated plants to confirm the VIGS of the AS1 gene at the molecular and the results are shown in FIG. 7H. AS1 RNA accumulation in the upper leaves of psTRV2:AS1 infected plant was much lower than that of plants infected with the empty sTRV vector and there is only 17% of AS1 RNA was left in AS1 treated plants.

These adaxial leaf blade phenotypes provide evidence that this is cotton AS1 gene and that TRV VIGS could be used in cotton to rapidly screen for function of TF genes. Such genes may be important for cotton boll development and cotton fiber initiation and elongation in different developing stages. More importantly, recent evidence shows that common networks regulate leaf and fruit patterning in *Arabidopsis* (Nurmberg et al., 2007). Thus, one can use the leaf as a model system for rapid assessment of TF gene functions and to make use of such information to further to make use of these genes to modify or enhance the quality and quantity of cotton fiber. In certain embodiments, the invention also provides plant products obtained from transgenic plants of the invention. The term "plant product" is intended to include anything that may be obtained from a particular plant, including, for example, fruits, seeds, pollen, ovules, plant embryos, oils, juices, waxes, proteins, lipids, fatty acids, vitamins, plant tissues in whole or in part, (e.g. roots, leaves, stems, flowers, boll, fruit, bark), cells, cell suspensions, tubers and stolons.

Example 6

Functional Analysis of Small RNA Pathway Genes in Cotton by VIGS

Small RNAs (smRNAs) regulate processes as diverse as plant resistance to viruses, and plant development and differentiation. We tested the ability of the TRV VIGS system for high-throughput analysis of functions of genes involved in smRNA biogenesis pathways.

All RNA-silencing pathways require the genesis of 18- to 26-nt smRNAs from the cleavage of double-stranded RNA (dsRNA) or highly structured regions within single-stranded viral RNAs. MicroRNA is one important kind of smRNAs. Bound to ARGONAUTE1 (AGO1) protein, miRNAs guide RNA-induced silencing complexes (RISCs) to cleave mRNAs with partial or complete sequence complementarity. Accordingly, *Arabidopsis* AGO1 binds miRNAs and displays slicer activity toward miRNA targets, and strong ago1 loss-of-function mutants overaccumulate miRNA target transcripts (Baulcombe, 2004). AGO1 has also proven to bind viral-derived siRNA and ago1 mutant show hypersusceptibility to virus (Beclin et al., 2002; Morel et al., 2002).

In order to study the role of AGO1 in cotton development and biotic stress, we first cloned the cotton homologue of AGO1. We used the amino acid sequence of *Arabidopsis* AGO1 (GenBank Accession Number NM_179453) to search the GenBank cotton EST database using TBLASTN. Several cotton EST clones showed significant homology to different regions of *Arabidopsis* AGO1. Based on this information, we obtained a 2329 bp partial cDNA sequences encoding a part of the putative cotton AGO1 protein. The nucleotide sequence of cotton AGO1 gene is set forth in SEQ ID NO:23. The amino acid sequence of cotton AGO1 is set forth in SEQ ID NO:24. Analysis of this putative cotton AGO1 shows 87.5% identity and 92.7% similarity to *Arabidopsis* AGO1 in this 776 aa region.

Figure 8:
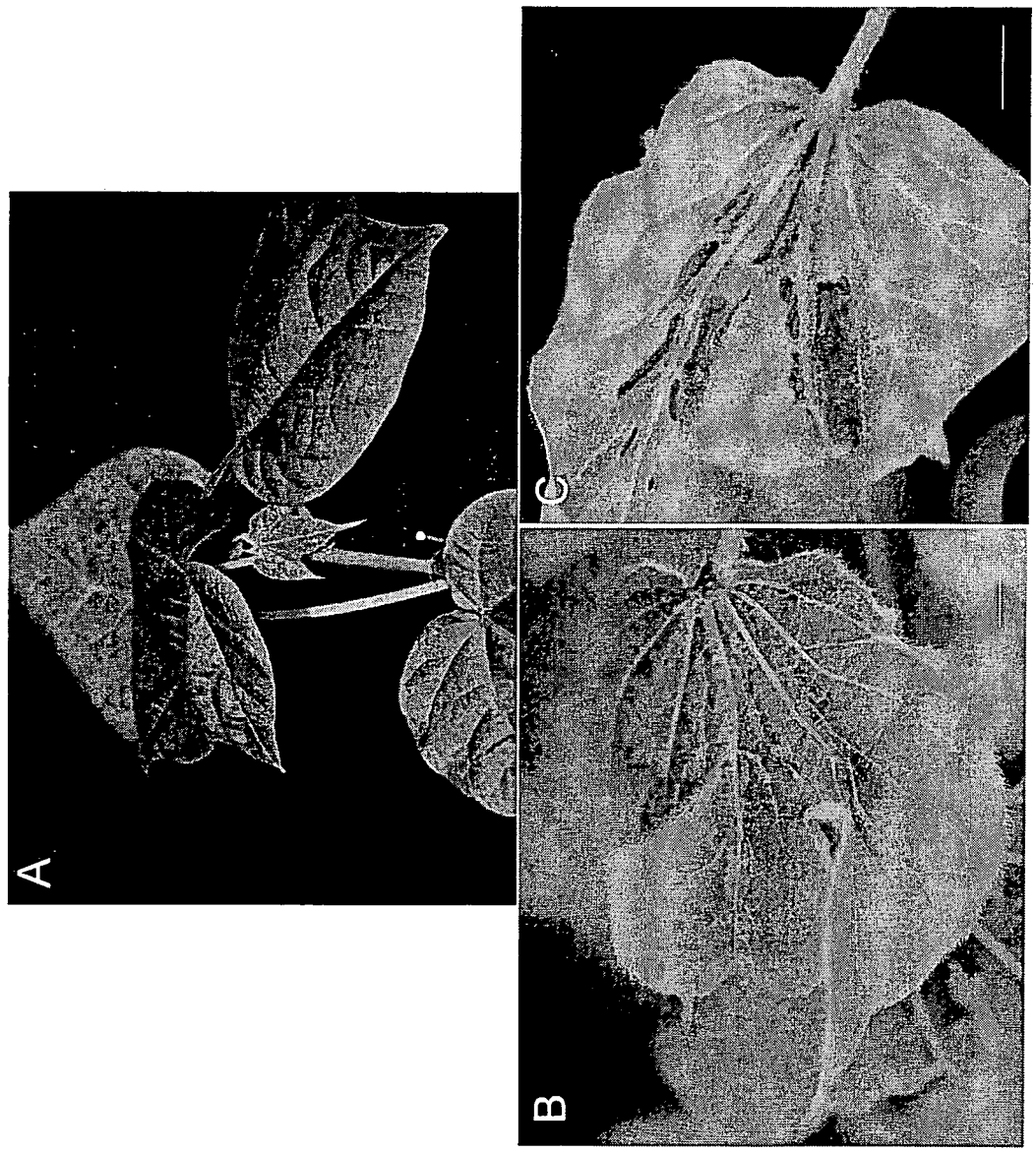
FIGS. 8A-8C show phenotypes of cotton plants infected with psTRV2:AGO1. PB: primary blade; EB, ectopic blade.

To amplify the AGO1-like gene for functional analysis using VIGS in cotton, PCR primers were designed to target a 583 bp fragment which was inserted into psTRV2 to give psTRV2:AGO1. A mixture of *Agrobacterium* cultures containing psTRV1 and psTRV2:AGO1 vector was vacuum infiltrated into cotton plants. A mixture of *Agrobacterium* cultures containing psTRV1 and psTRV2:AGO1 vector was infiltrated into cotton plants. After 27 dpi, diverse and varied phenotypes can be seen in new emerged leaves. Severe upward curling was the most obvious phenotype both from the adaxial side (FIG. 8B) and the abaxial side (FIG. 8C) of leaves. AGO1-silenced leaves showed a specific disruption in the abaxial domain, leading to the formation of abaxial ectopic leaf blades (FIG. 8C). We further observed ectopic abaxial leaf blades structure emerged along with the leaf vein and the ectopic abaxial side faced to the primary blade abaxial (FIG. 8C). In *Arabidopsis*, ectopic PHAV expression leads to the formation of ectopic abaxial leaf blade in AGO1 mutants (Kidner and Martienssen, 2004). In Jatropha, a small and woody plant of the Euphorbiaceae family, silencing of AGO1-like gene also leads to similar ectopic abacial leaf blade and upward leaf curling (see International patent application No. PCT/SG20009/000481 filed on 16 Dec. 2009 and U.S. provisional patent application No. 61/143,484 filed on 9 Jan. 2009). These phenotypic similarities suggest this gene is an AGO1 homologue in cotton.

These abaxial leaf blade phenotypes provide evidence that this is the cotton AGO1 gene and that TRV VIGS could be used in cotton to rapidly screen for function of small RNA regulated pathway and virus resistance pathway. Such genes may be important for cotton boll development and cotton fiber initiation and elongation in different developing stages. More importantly, recent evidence shows that common networks regulate leaf and fruit patterning in *Arabidopsis* (Nurmberg et al., 2007). Thus, one can use the leaf as a model system for rapid assessment of small RNA pathway gene functions and to make use of such information to further to make use of these genes to modify or enhance the quality and quantity of cotton fiber. In certain embodiments, the invention also provides plant products obtained from transgenic plants of the invention. The term "plant product" is intended to include anything that may be obtained from a particular plant, including, for example, fruits, seeds, pollen, ovules, plant embryos, oils, juices, waxes, proteins, lipids, fatty acids, vita-

Example 7

Functional Analysis of Proanthocyanidins in Cotton by VIGS

Proanthocyanidins (PAs) is one major class of flavonoids, one of the largest groups of plant secondary metabolites. PAs are oligomeric and polymeric end products of the flavonoid biosynthetic pathway. PAs act as antibiotics, antisporulants, feeding deterrents, and enzyme denaturants. Many evidences have shown good correlation between cotton wilt disease/insect resistances with PAs level in cotton. Most genetic studies on PAs biosynthesis pathway were done model plant *Arabidopsis* and recently *Medicago truncatula*. By our knowledge, there is no gene functional analysis in PA biosynthesis pathway in cotton. We took advantages of our sTRV VIGS system in cotton to decipher structure genes and regulated network for PA biosynthesis process.

PAs are one class of products from the pathway leading to anthocyanins. Two enzymes anthocyanidin synthase (ANS) and anthocyanidin reducatase (ANR) function at branches between anthocyanin and PA biosynthesis. ANS converts the substrate flavan-3,4-diol (leucoanthocyanidin) to anthocyanidin, which can serve as substrate for ANR to produce another major PA unit, 2,3-cis-flavan-3-ol (epicatechin) in *Arabidopsis* and *Medicago*.

Figure 9:
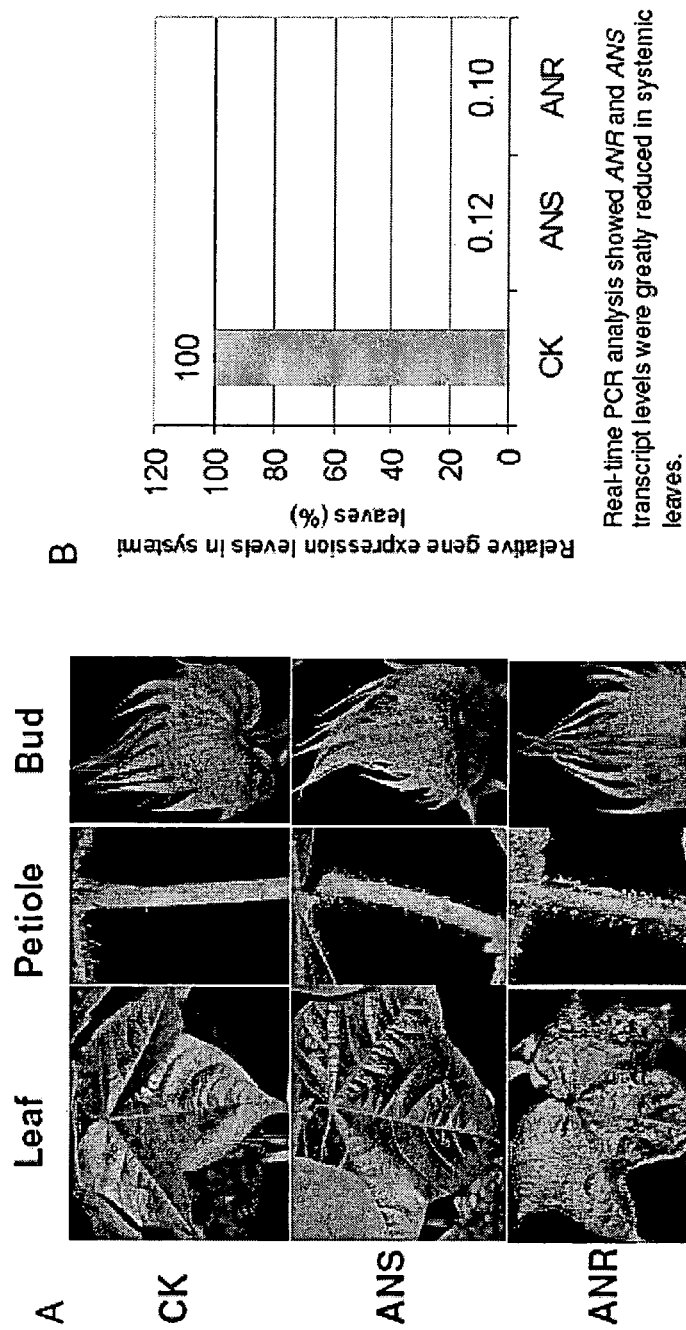
FIG. 9H: Quantitative real-time PCR using total RNA extracted from upper leaves of treated plants. The real-time PCR analysis showed that AS1 a transcript levels were greatly reduced in systemic leaves. PB: primary blade; EB, ectopic blade; ebad: ectopic blade adaxial; ebab: ectopic blade abaxial. CK: vector control infected; AS1, leaves from plants silenced in AS1 expression.
FIGS. 9A and 9B show the silencing of anthocyanidin and proanthocyanidin biosynthesis gene ANS and ANR in cotton leaves.
Figure 10:
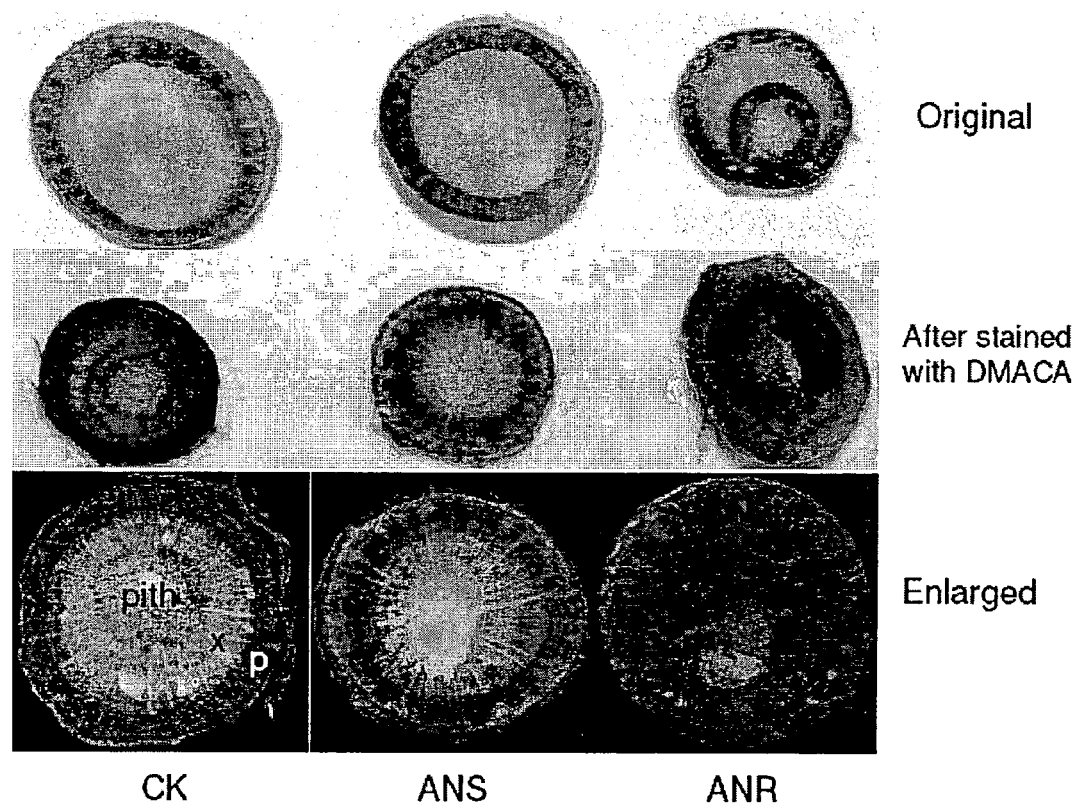
FIG. 10 shows the silencing of anthocyanidin and proanthocyanidin biosynthesis gene ANS and ANR in cotton bark.
Figure 11:
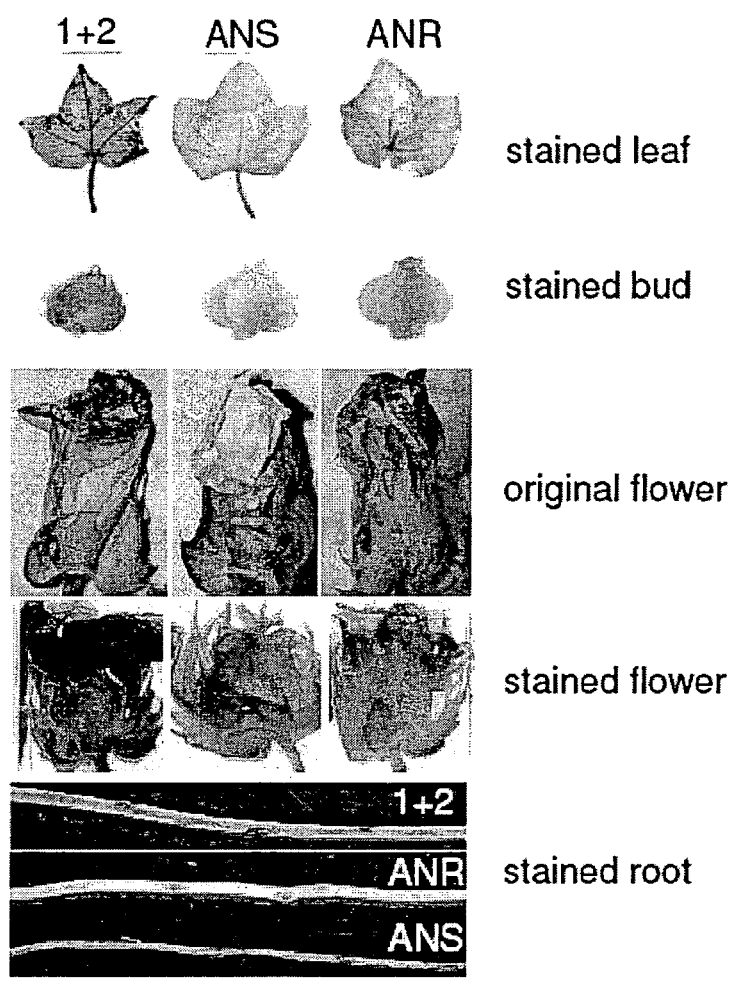
FIG. 11 shows the silencing of anthocyanidin and proanthocyanidin biosynthesis gene ANS and ANR in different cotton organs.
Figure 12:
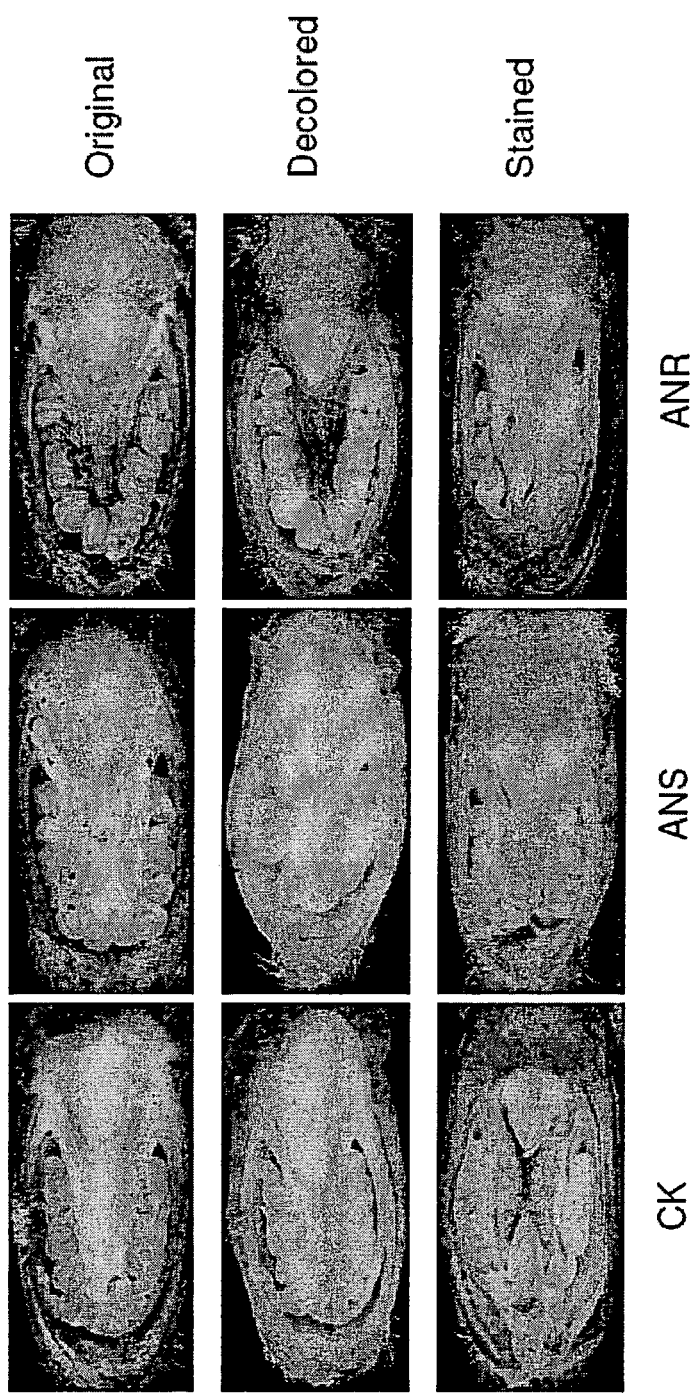
FIG. 12 shows the silencing of anthocyanidin and proanthocyanidin biosynthesis gene ANS and ANR in cotton buds.

Two putative genes coding ANS and ANR were used to insert into sTRV VIGS vector, for functional analysis. To amplify these two genes from *Gossypium hirsutum*, we designed PCR primers (ANS: SEQ ID NOs:58 and 59; ANR: SEQ ID NOs:60 and 61) to amplify partial fragments of putative GhANS and GhANR according to the querying results of GenBank EST database with amino acid sequence of *Arabidopsis* ANS and ANR proteins. The PCR products (ANS: SEQ ID NO:78; ANR: SEQ ID NO:79) were further into cloned psTRV2 to give psTRV2:ANS and psTRV2:ANR. A mixture of *Agrobacterium* cultures containing psTRV1 with psTRV2, psTRV2:ANS or psTRV2:ANR was vacuum infiltrated into 2-3 true leaf cotton plants. After 7-10 days post inoculation, leaf margin around new systemic leaves of psTRV2:ANR cotton plants appeared brownish phenotypes. Two to 7 days later, gene silencing phenotype was obvious in whole leaf blade, esp. the leaf veins in 3-5 new, expanding leaves (FIG. 9A) and the brownish phenotype was also visible in the lateral leaf below the infiltrated leaf. Brownish phenotype can be also found on the petiole (FIG. 9A), bark (FIG. 10), root (FIG. 11) and reproductive organ flower bud (FIG. 12). We deduce this brownish phenotype was due to blocking ANR functions on conversion anthocyanidin into proanthocyanidin unit. This blocking leads to accumulate higher level of colourful substrate anthocyanidin. On contrast, ANS plants show no visible phenotype difference with vector control plants. Transcript analysis by real-time PCR showed 99.9% reduction of ANS and ANR transcript levels in corresponding plants compared to vector (1+2) control (FIG. 9B).

Figure 13:
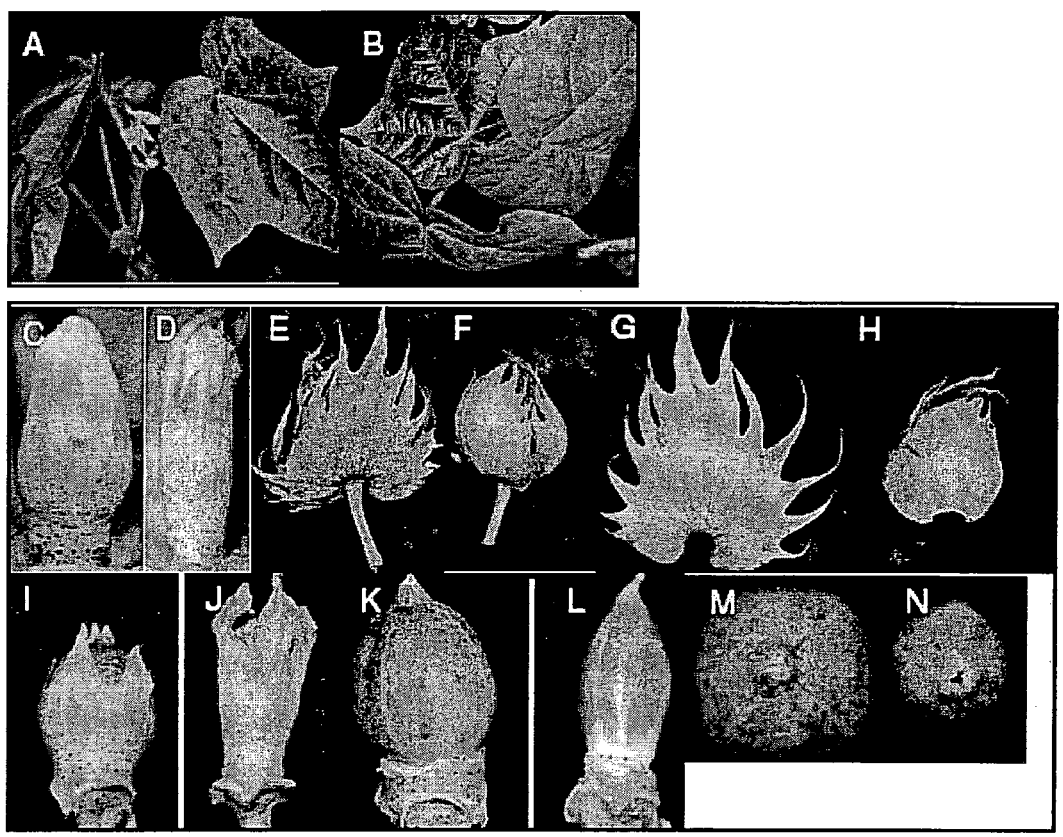
FIGS. 13A-13N show the silencing of the CtBP ortholog gene AN in cotton in leaves (FIGS. 13A and 13B), flower bud and ball in psTRV2:AN treated plants (FIGS. 13D, 13F, 13H, 13J, 13L and 13N) and in flower bud and ball in control plants (FIGS. 13C, 13E, 13G, 13I, 13K and 13M).

Next we used the widely-used PAs staining reagent DMACA to check the PAs accumulation level in gene silencing cotton. The DMACA, an aromatic aldehyde, shows deep blue coloration after reaction with catechins, the major flavan-3-ols associated in cotton PAs. Most of the tissues in vector (1+2) control plants contain high level of PAs level as showed by DMACA staining (bark in FIG. 11, leaf, bud, flower, root in FIG. 12 and dissected bud in FIG. 13). For example in cotton leaf, PAs are highly accumulated in parenchyma cell around phloem. The leaf vein region and petiole show deeper anthocyanidin red color in ANR plants. In contrast to ANR plants, ANS plants show colorless because there is neither anthocyanidin red color nor PAs blue color (FIG. 11, FIG. 12 and FIG. 13). Both ANR and ANS silencing results prove silencing effect can enter into all over the cotton plants and shows very homogenous silencing effect, which is very important merit for a good VIGS system (FIG. 4A-FIG. 7). More importantly, silencing can be achieved in reproductive organs, such as bud, flower and ovule. These results indicate sTRV VIGS can be used to screen genes important for cotton fiber development. ANS and ANR silencing were also found in the cotton roots, where *verticillium dahliae* infects from and causes the wilt disease. That strongly suggested that sTRV VIGS system can also be used to cotton fungal disease resistance.

Example 8

Functional Analysis of a CtBP in Cotton by VIGS

Cotton fibers are seed trichomes and are the most important product of cotton plants. Cotton fiber development undergoes several distinctive but overlapping steps including fiber initiation, elongation, secondary cell wall biosynthesis, and maturation, leading to mature fibers. Single-celled cotton fiber also provides a unique experimental system to study cell elongation. Many evidences demonstrated in previous examples have shown sTRV VIGS system can work effectively both in vegetative but also reproductive organs such as flower and bud. In this example, we showed sTRV VIGS can also work in cotton fiber.

CtBP (C-terminal binding protein) is an evolutionarily conserved NAD(H)-dependent transcriptional corepressor, whose activity has been shown to be regulated by the NAD/NADH ratio. Although recent studies have provided significant new insights into mechanisms by which CtBP regulates transcription and interaction with other protein components, the biological function of CtBP remains incompletely understood. ANGUSTIFOLIA (AN) is the first C-terminal binding protein (CtBP) gene from plants and controls leaf width and pattern of trichome branching in *Arabidopsis*. However the role of CtBP or its ortholog in cotton fiber development is unknown.

Figure 16:
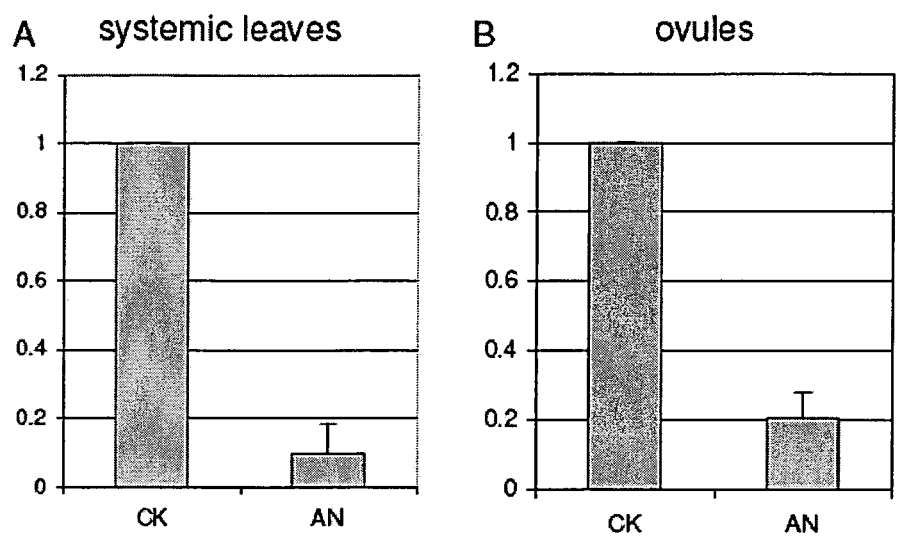
FIGS. 16A and 16B show silencing of the CtBP ortholog gene AN in cotton systemic leaves (FIG. 16A) and ovules (FIG. 16B). The real-time PCR analysis showed that AN transcript levels were greatly reduced in both systemic leaves and ovules. CK: vector control infected; AN, leaves from plants silenced in AN expression.

To amplify the AN ortholog from *G. hirsutum*, a putative EST sequence was identified by using *Arabidopsis* AN gene (NM 100033) sequence to BLAST against the whole cotton EST sequences of GenBank. One EST encoded the putative AN protein in cotton was identified. PCR primers (SEQ ID NOs:62 and 63) were designed to amplify a 621-bp AN cDNA of *G. hirsutum* by PCR, and the AN fragment (SEQ ID NO:80) was inserted into the sTRV2 MCS site to give psTRV2:AN. The sequence of AN was also verified by sequencing. Cultures of *Agrobacterium* carrying pTRV1 was mixed with cultures of *Agrobacterium* carrying either psTRV2:AN or vector control. The mixed culture was vacuum-infiltrated into *G. hirsutum* plants with 2-3 true leaves (for details see Example 1). There are no obvious phenotypes in vegetative organs of AN-silenced cotton plants, such as leaf width (FIGS. 13A and 13B) and pattern of trichome branching. We performed quantitative realtime PCR, using total RNA extracted from upper leaves of treated plants to confirm the VIGS of the AN gene at the molecular and the results are shown in FIG. 16A. AN RNA accumulation in the upper leaves of psTRV2:AN infected plant was much lower than that of plants infected with the empty sTRV vector and there is only 10% of AN RNA was left in AN treated plants. These data suggested the role of AN on leaf expansion in the leaf width direction is not conserved in cotton.

Figure 14:
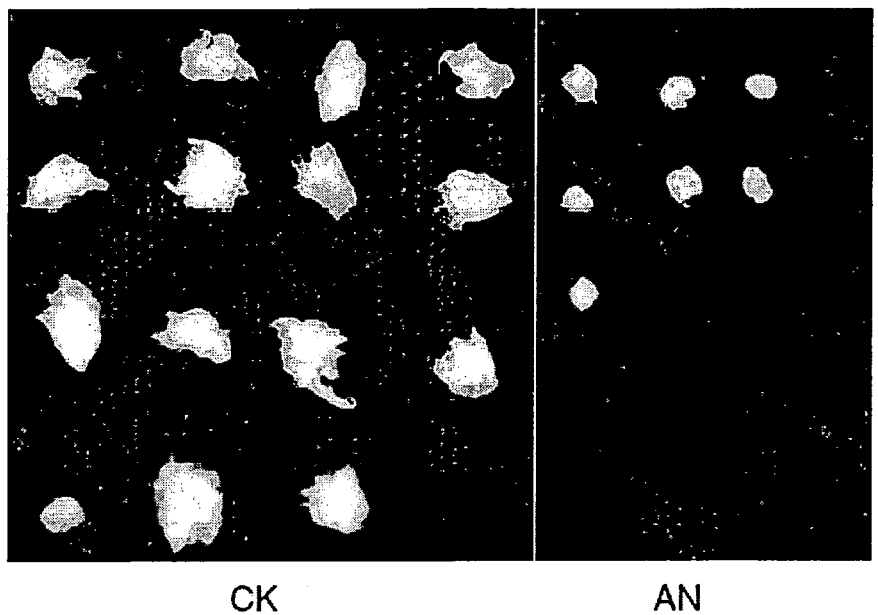
FIG. 14 shows silencing of the CtBP ortholog gene AN in cotton ovule and fiber. CK: vector control infected; ANR, leaves from plants silenced in AN expression.
Figure 15:
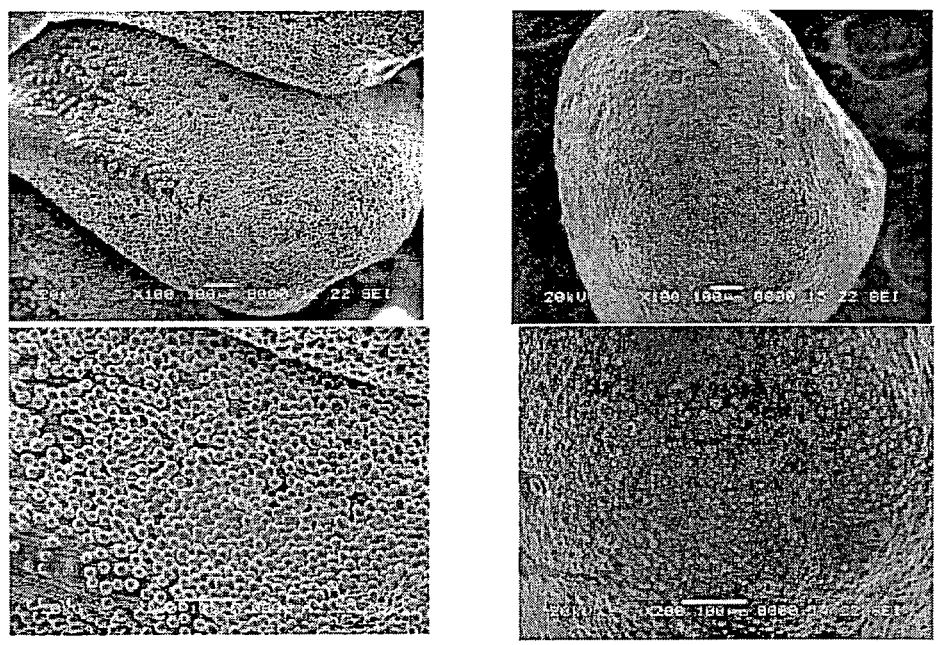
FIG. 15 shows that the cotton CtBP ortholog gene AN plays a key role in cotton fiber initiation. 1+2: vector control infected; AN, leaves from plants silenced in AN expression.

On contrast of no obvious roles on vegetative growth and development, AN plays an very impressively key role in organ size determination, specific in width orientation and fiber development. In AN-silenced cotton, the flower bud and ball was thinner and smaller (FIGS. 13D, 13F, 13H, 13J, 13L, 13N) comparing to control (FIGS. 13C, 13E, 13G, 13I, 13K, 13M) individually. The most severe phenotype in AN-silenced ball showed few initiated fiber in one ovule and totally few ovule number in one ball (FIG. 14 and FIG. 15). Real-time PCR analysis showed AN transcript levels were greatly reduced in ovules (FIG. 16B). This may be caused by abnormal arrangement of cortical MTs. It has been proved that the abnormal arrangement of cortical microtubules account for the abnormal shape of the cells in *Arabidopsis*. AN gene might regulate the polarity of cell growth by controlling the arrangement of cortical MTs (Kim et al., 2002).

Beside AN role in cytoskyloton, there might be other roles such as negative transcriptional regulation on development by interaction with other protein components. AN encodes a novel protein with sequence similarity to C-terminal binding protein/BrefeldinA ribosylated substrates that are known to be involved in transcriptional regulation or in vesicle budding. In the animal kingdom, CtBPs self-associate and act as co-repressor of transcription. In mouse, CtBP invoved in embryogenesis, mutants leads to embryo development stop at some stages. This may help to explain why some of AN-silenced ovule is lethal in cotton ovule development (FIG. 14). Microarray analysis in *Arabidopsis* suggested AN gene might regulate the expression of certain genes, e.g. the genes involved in formation of cell walls (Kim et al., 2002).

This example clearly proved sTRV VIGS works very well in cotton fiber and ovule development step, which is the key stage to determinate cotton fiber length, fiber and ovule number.

Example 9

Functional Analysis of KTN in Cotton by VIGS

Microtubule cytoskeleton plays an important role in cell morphogenesis in plants as demonstrated by pharmacological, biochemical, and genetic studies. The microtubule cytoskeleton may be involved in the transportation of organelles and vesicles carrying membranes and cell wall components to the site of cell growth as in root hairs, trichome cells, and pollen tubes. Therefore, the microtubule cytoskeleton is essential for cell elongation and tip growth.

Katanin (KTN) is a heterodimeric microtubule (MT) severing protein that uses energy from ATP hydrolysis to generate internal breaks along MTs. Katanin p60, one of the two subunits, possesses ATPase and MT-binding/severing activities, and the p80 subunit is responsible for targeting of katanin to certain subcellular locations. In animals, katanin plays an important role in the release of MTs from their nucleation sites in the centrosome. It is also involved in severing MTs into smaller fragments which can serve as templates for further polymerization to increase MT number during meiotic and mitoticspindle assembly. Katanin homologs are present in a wide variety of plant species. The *Arabidopsis* katanin homolog has been shown to possess ATP-dependent MT severing activity in vitro and exhibit a punctate localization pattern at the cellcortex and the perinuclear region. Disruption of katanin functions by genetic mutations causes a delay in the disappearance of the perinuclear MT array and results in an aberrant organization of cortical MTs in elongating cells. Consequently, katanin mutations lead to defects in cell elongation, cellulose microfibril deposition, and hormonal responses. Studies of kataninin plants provide new insights into our understanding of its roles in cellular functions.

Enrichment of siRNAs in ovules and fibers suggests active small RNA metabolism and chromatin modifications during fiber development, whereas general repression of miRNAs in fibers correlates with upregulation of a dozen validated miRNA targets encoding transcription and phytohormone response factors, including the genes found to be highly expressed in cotton fibers. Microtubule dynamics play a role in miRNA-guided translational inhibition but not in miRNA-guided cleavage. However the role of KTN in reproductive organ development or its ortholog in cotton fiber development is unknown To amplify the KTN ortholog from *G. hirsutum*, a putative EST sequence was identified by using *Arabidopsis* KTN gene (NM_106684.4) sequence to BLAST against the whole cotton EST sequences of GenBank. One EST encoded the putative KTN protein in cotton was identified. PCR primers (SEQ ID NOs:64 and 65) were designed to amplify a 675-bp KTN cDNA of *G. hirsutum* by PCR, and the KTN fragment (SEQ ID NO:81) was inserted into the sTRV2 MCS site to give psTRV2:KTN. The sequence of KTN was also verified by sequencing. Cultures of *Agrobacterium* carrying pTRV1 was mixed with cultures of *Agrobacterium* carrying either psTRV2:KTN or vector control. The mixed culture was vacuum-infiltrated into *G. hirsutum* plants with 2-3 true leaves (for details see Example 1).

Figure 17:
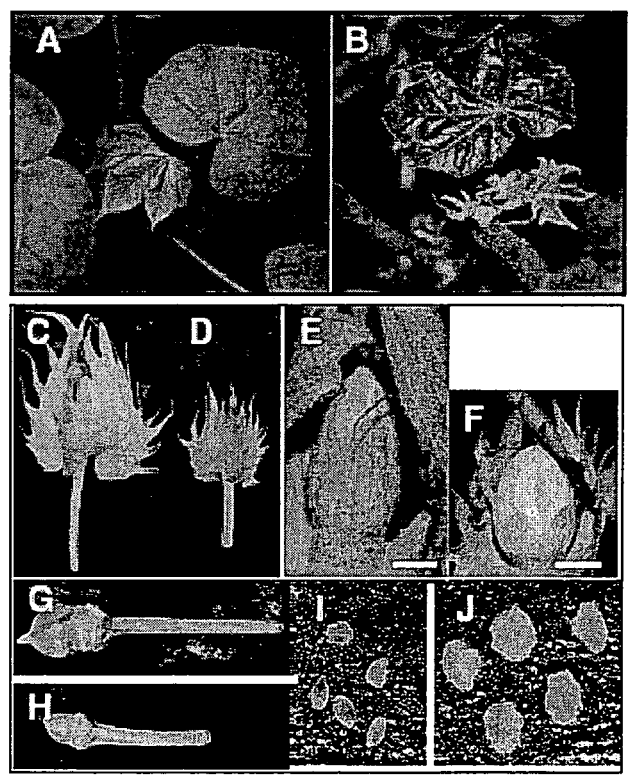
FIGS. 17A-J show silencing of cytoskeleton gene Katanin (KTN) in cotton. Phenotypic effect in vector control treated plant (FIG. 17A), in psTRV2:KTN treated plant (FIG. 17B), in flower bud and ball in psTRV2: KTN treated plants (FIGS. 17D, 17F, 17H and 17J) and in flower bud and ball in control plants FIGS. 17C, 17D, 17G and 17I).
Figure 19:
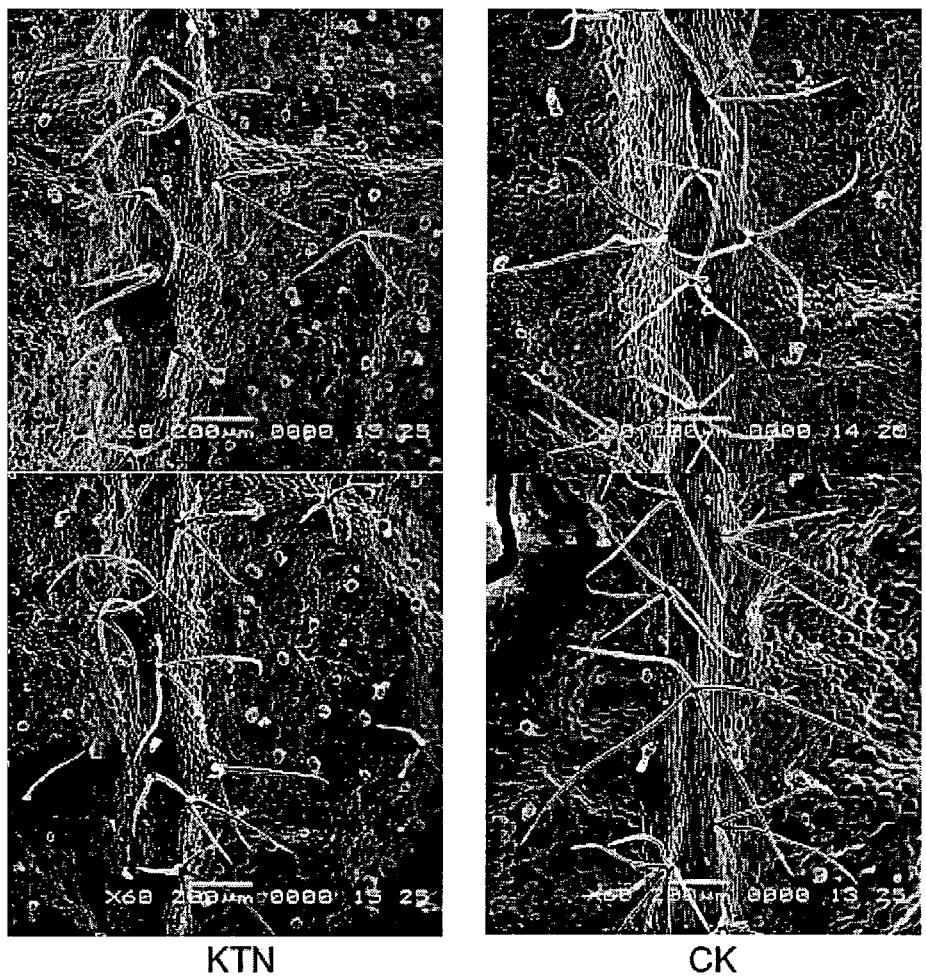
FIG. 19 shows that KTN plays a role in leaf trichome length and patterning.

There are very obvious phenotypes in vegetative organs of KTN-silenced cotton plants, such as dark green and smaller leaf blades, shorter petiole (compare with vector control in FIG. 17A and KTN-silenced in FIG. 17B) and pattern of trichome branching and length of leaf trichomes (FIG. 19). These data suggested KTN play multiple significant roles on plant development.

Figure 18:
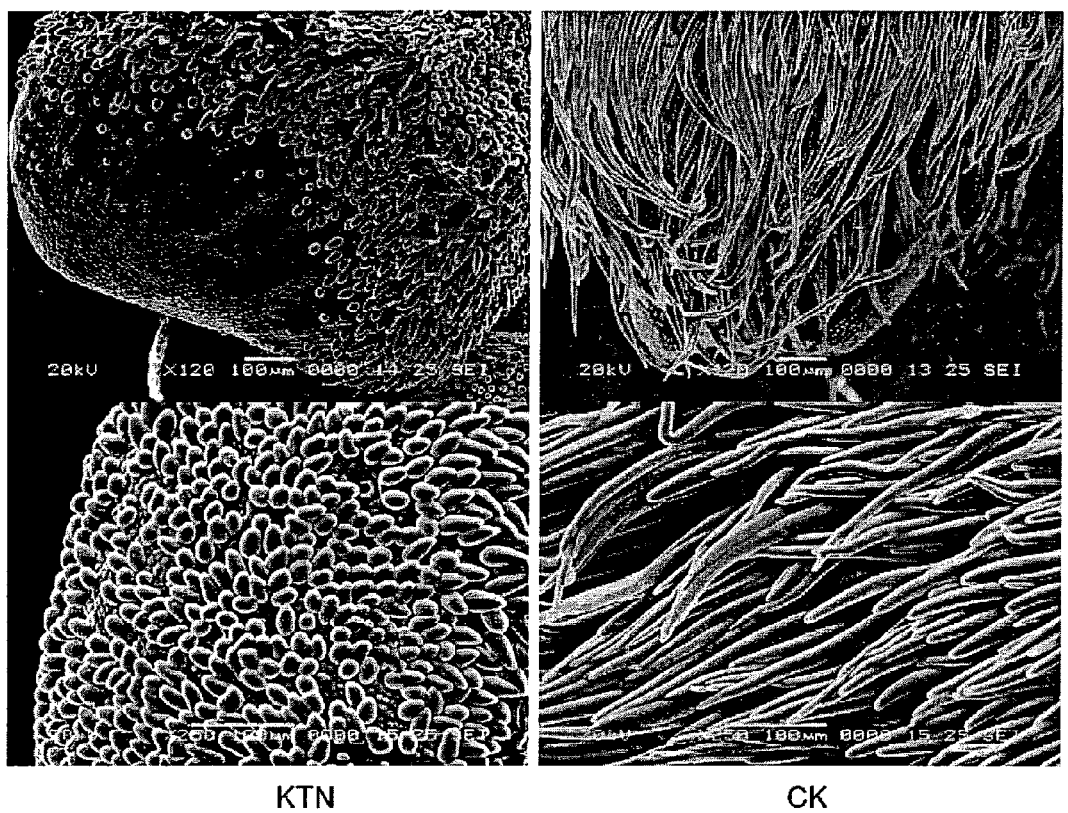
FIG. 18 shows that KTN is an essential gene for cotton fiber elongation.

KTN not only plays key roles on vegetative growth and development, but also plays very impressively key roles in organ size determination, specific in width orientation and fiber development. In KTN-silenced cotton, the flower bud and ball was thinner and smaller (FIGS. 17D, 17F, 17H, 17J) comparing to control (FIGS. 17C, 17E, 17G, 17I) individually. The most severe phenotype in KTN-silenced ball showed much shorter fiber in one ovule (FIG. 18). This may be caused by abnormal arrangement of cortical MTs. It has been proved that the abnormal arrangement of cortical microtubules account for the abnormal shape of the cells in *Arabidopsis*.

Example 10

Expression in Cotton Using Transient Expression Vector

The use of crops that are genetically engineered to produce expressed protein or polypeptide such as *Bacillus thuringiensis* (Bt) toxins has risen rapidly to more than 32 million hectares. Transient systems to quickly express exogenous or endogenous polypeptide is greatly needed in cotton, which is difficult to transform.

Examples of transient expression using the method of the present invention are detailed below. Briefly, the method requires that a heterologous DNA construct comprising a plant promoter, a DNA sequence encoding a protein. Preferably, the DNA construct encodes an additional gene of interest. For example, the DNA construct may include a gene the expression of which results in increased cotton resistance to insect or increase cotton fiber length or other agronomic properties in infiltrated plants.

In the example below, cotton plants transiently expressing green fluorescent protein (GFP) were obtained from tissue was vacuum infiltrated with agrobacterium that included a GFP gene. This GFP gene and other genes such as GUS, luciferase gene, which can serve as easily screenable markers, were used in some of the examples described below, simply because their phenotypes can be readily detected in the vacuum-infiltrated plants. It is reasonable to expect that by using DNA constructs created by standard molecular biological techniques, the present invention may be employed to obtain a cotton plant expressing virtually any other gene. In an alternative embodiment, the method for obtaining transient expressed cotton plants involves the fusion of GFP with other genes and the other of which comprises a gene of interest.

Figure 20:
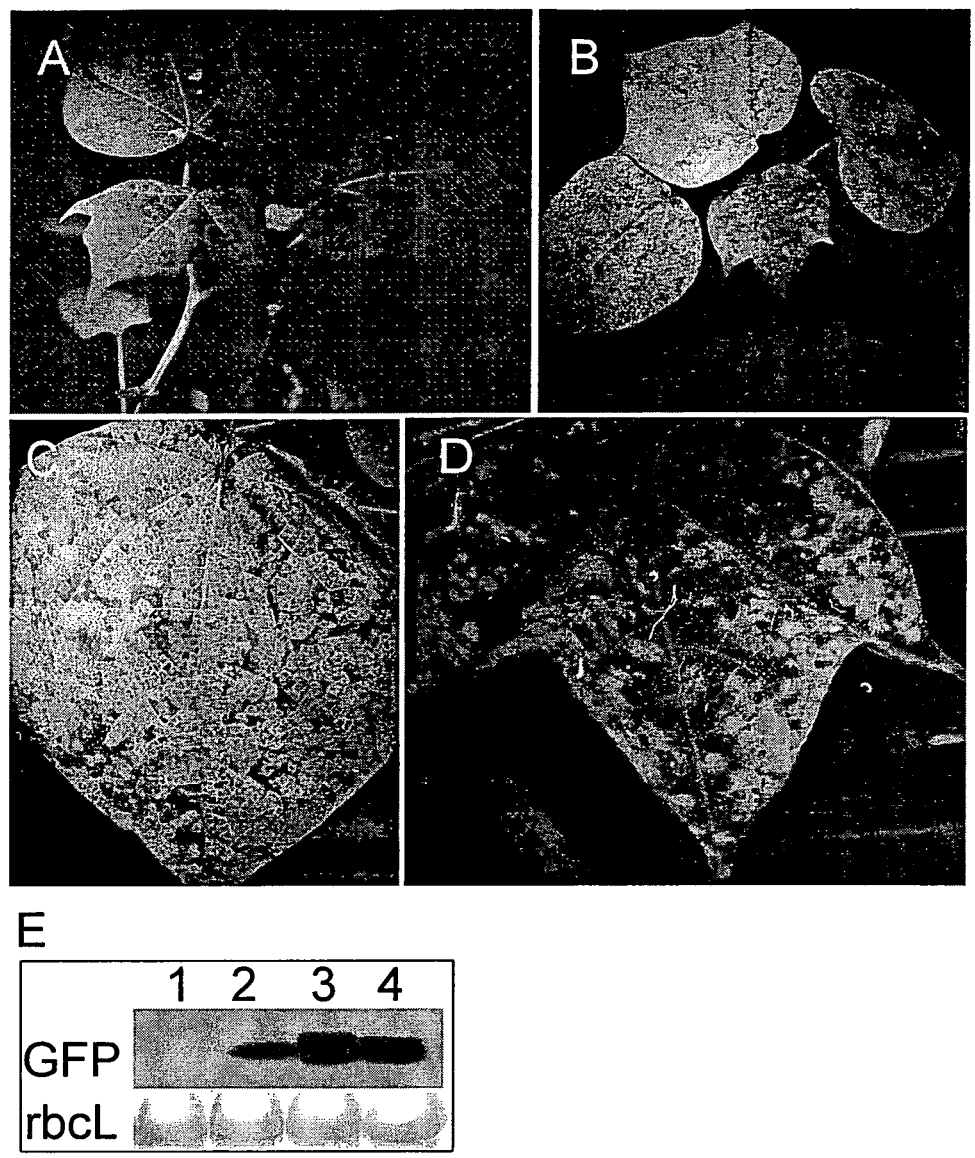
FIGS. 20A-20E show plants infected with psTRV2:GFP.

To amplify the GFP gene for transient expression analysis as a marker in cotton, PCR primers were designed to a fragment which was inserted into the psTRV2001, with a synthetic pea early browning virus (PEBV) subgenomic promoter to give psTRV2:GFP. A mixture of *Agrobacterium* cultures containing psTRV 1 and psTRV2:GFP vector was vacuum infiltrated into cotton plants. At 3 dpi, strong GFP expression was fast screened when infiltrated cotton plants excited with ultraviolet light in whole plants (FIGS. 20B, 20C, 20D). Cotton leaves were collected and GFP antiboby was used to detect the curcin protein. Western blot analysis showed that strong GFP accumulated in cotton leaves. Coomassie Bright Blue staining of the large subunit of ribulose 1,5-bisphosphate carboxylase/oxygenase indicates comparable loading of the samples.

Example 11

Modified VIGS Vector Containing an Intron

There are many reasons that cause RNA viral vectors to have difficulties in initiation of transcription. First, the non-optimized genome sequence might be improperly recognized by the RNA processing machinery such as cryptic splice sites and thymine-rich, putative intron sequences embedded in RNA genomes. Second, TRV RNA1 viral vector encode very large transcripts about 7.0 kilonucleotides, a size is about 3-4 fold of avarage plant genes size (1-2 Kb). In nature, plant genes often contain huge numbers of introns that facilitate processing and export of the pre-mRNA from the nucleus. In the agroinfiltration-based VIGS and transient expression systems of the present invention, pre-mRNA transcripts made in plant nucleus from viral constructs may not be efficiently recognized or proper processing without intron sequences. Addition of an intron can make the viral transcript easier to be recognized by the host huclear pre-mRNA processing and export machinery, therefore to increase the percentage of plant cells in which viral replication could occure, but also the efficiency by which an infection could be initiated.

The consensus sequences AG/GT is used as a target sequence for intron insetion. In a second round screen cycle, we analyzed the sequence of TRV1 using the NetgeneII program (http colon backslash backslash www dot cbs dot dtu dot dk backslash services backslash NetGene2/) with parameters set for *A. thaliana* sequences. We noticed one site (position of 10919-10922 in psTRV1001 sequence) cotaining AG/GT with a high confidence to act as a donor splice site. Therefore we chose this site for insertion of plant intron.

Overlapping PCR was used to generate TRV1 fused with intron sequence derived from *A. thaliana* and inserted into the psTRV1001 vector to make psTRV1001-intron vector. The modified vector is analyzed to show that the intron-containing vector can lead to better VIGS effiencncy and higher overexpression level.

Example 12

Materials and Methods for Example 13

The approach described in Examples 12 and 13 involves cloning a short sequence of a targeted cotton gene correlating to cell elongation, cell wall and cellulose biosynthesis into a viral delivery vector. The vector is used to infect the cotton ovules in vitro, and in a few days or weeks natural defense mechanisms directed at suppressing virus replication also result in specific degradation of mRNAs from the endogenous plant gene that is targeted for silencing. The method is rapid (1-4 days from infection to silencing), does not require development of stable transformants, allows characterization of phenotypes that might be lethal in stable lines, and offers the potential to silence either individual or multiple members of a gene family.

Plant growth conditions: All the cotton plants (*Gossypium hirsutum*) were grown in potting soil in a greenhouse with natural temperature and light. Flower buds to be used for the collection of ovaries were tagged on the day of anthesis and the corresponding bolls were harvested at 1 day after that day.

Figure 21A:
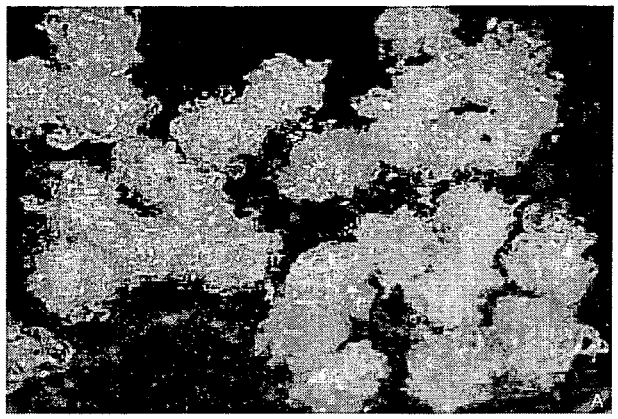
FIGS. 21A and 21B show cotton ovule culture.
Figure 21B:
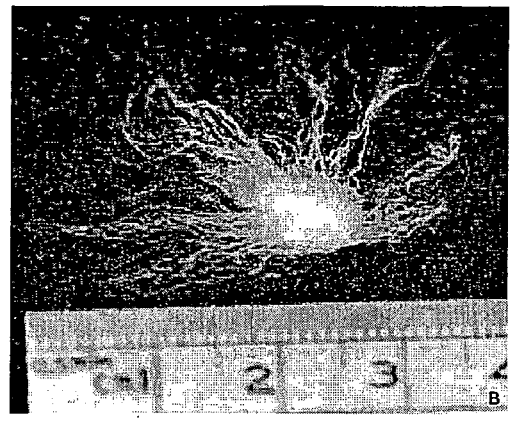

Cotton ovule culture: One day post-anthesis (DPA), flower buds or bolls were collected, and bracts, sepals, and petals were removed. Ovaries were surface sterilized by using 75% ethanol, followed by washing with sterile water 3-5 times. Ovules were carefully dissected from the ovaries under aseptic conditions. These ovules were infected by TRV containing the Actin 1 gene. Followed by washing with sterile water 3-5 times, these ovules were immediately floated on the surface of BT medium supplemented with 1.1 mg/L IAA, 1.7 mg/L GA3 and 0.3 mg/L IBA (Beasley and Ting 1973). Oxygenate (pure oxygen) the BT medium over 30 min before use. The ovules were incubated at 32E C in the dark without agitation except for occasional brief periods for examination. Cotton ovule culture is shown in FIGS. 21A and 21B.

Scanning electron microscopy: In order to examine fiber initiation and elongation, ovules infected by TRV-Actin 1 were placed on double-sided sticky tape on an aluminum specimen holder and frozen immediately in liquid nitrogen. The frozen sample was viewed with a JSM-6360LV scanning electron microscope (JEOL, Tokyo, Japan).

Total RNA extraction: Cotton fibers were frozen in liquid nitrogen and ground with a pestle to a fine powder in a cold mortar. Total RNA was extracted according to Wan and Wilkins (1994) with up to 100 mg of ground fibers. All RNA preparations were DNase treated and purified by Qiagen RNeasy plant mini kit.

Reverse transcription—PCR analysis: A two-step RT-PCR procedure was performed in all experiments. First, First-strand cDNA was synthesized from 2 µg total RNA using the Superscript first-strand synthesis system for RT-PCR (Invitrogen) and was primed with 1 µg of oligo(dT) (dT15). Then, the cDNAs were used as templates in RT-PCR reactions with gene-specific primers. The RT-PCR primers used for amplifying GhActin 1 were Act-up (5'-ATATTCTAGAAGAA-GAACTATGAGTTGCCT-3'; SEQ ID NO:28) and Act-dn (5'-ATGGG ATCCCGTAGAGATCCTTCCTGATAT-3'; SEQ ID NO:29). Tubulin gene was used as the RNA standard. The RT-PCR primers used for amplifying the GhTubulin gene were Tub-up (5'-GATGTTGTGCCCAAGGATGTTAATGC-3'; SEQ ID NO:30) and Tub-dn (5'-ATGAGATCA AACT-TGTGGTCAATGCG-3'; SEQ ID NO:31).

Real-time PCR analysis: The expression of the GhActin 1 gene in cotton fibers was analyzed by real-time quantitative RT-PCR using the fluorescent intercalating dye SYBR-Green in a LightCycler detection system (Applied Biosystems) using the gene specific primers set forth in Table 4. A cotton Tubulin gene (GhTubulin) or Ubiquitin gene (GhUbiquitin) was used as a standard control in the QRT-PCR reactions. The real-time PCR reaction was performed using the Power SYBR Green PCR Master Mix (Applied Biosystems) with an ABI 7900 sequence detection system according to the manufacturer's instructions (Applied Biosystems). The amplification of the target genes was monitored every cycle by SYBR-Green fluorescence. The relative value for expression level was calculated by the equation Y=taget gene (Actin 1)/standard control (Tubulin or Ubiquitin).

Green RT-PCR using gene-specific primers (Table 4). To understand whether the changed length of fiber also including all of the candidate genes, we observed the ovules surface by scanning electron microscopy.

Figure 22A:
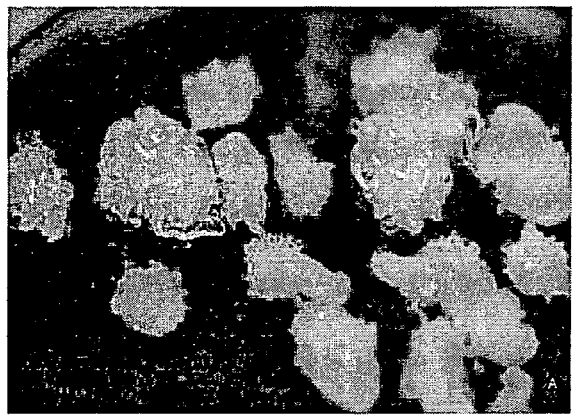
FIGS. 22A and 22B show actin gene expression in cotton.
Figure 22B:
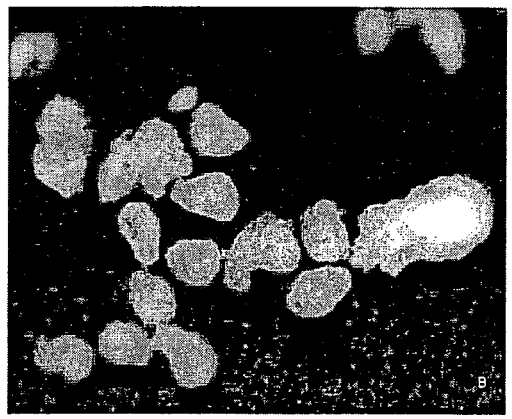
Figure 23D:
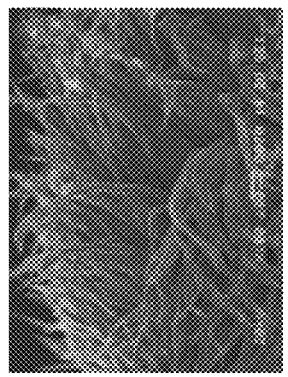
FIGS. 23A-23L show scanning electron micrographs of the ovule surface of VIGS-GhActin1, VIGS-GhADF1 and psTRV1+psTRV2.
Figure 23H:
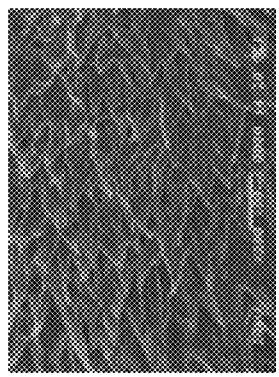
Figure 23L:
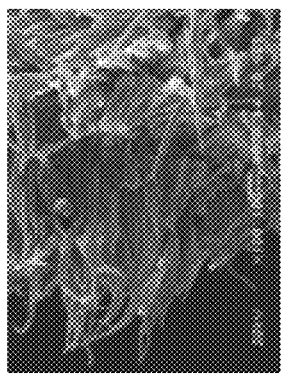
Figure 23C:
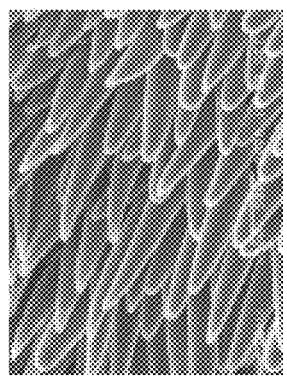
Figure 23G:
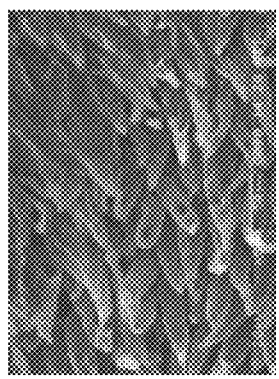
Figure 23K:
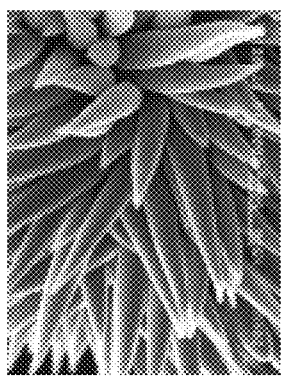
Figure 23B:
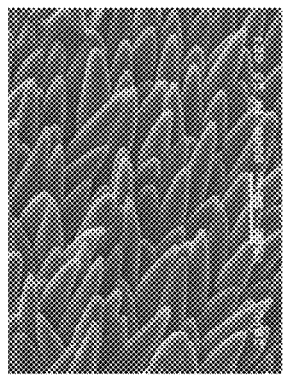
Figure 23F:
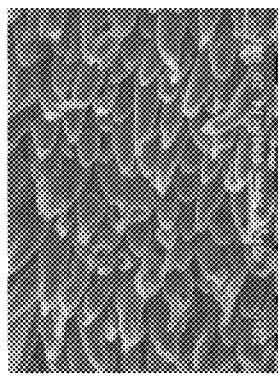
Figure 23J:
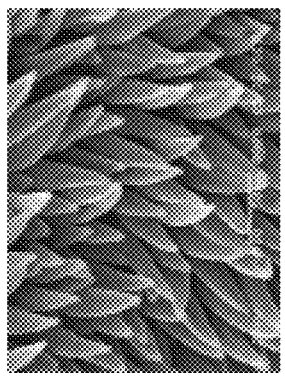
Figure 23A:
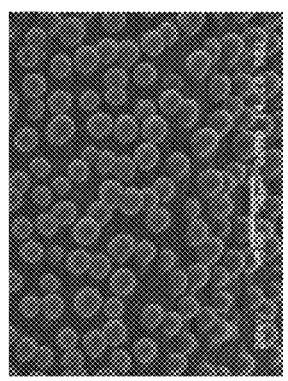
Figure 23E:
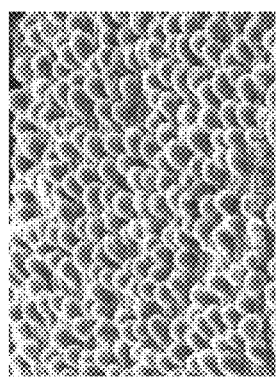
Figure 23I:
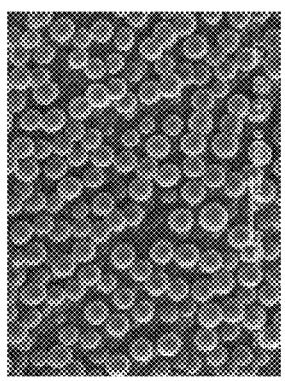
Figures 27A, 27B:
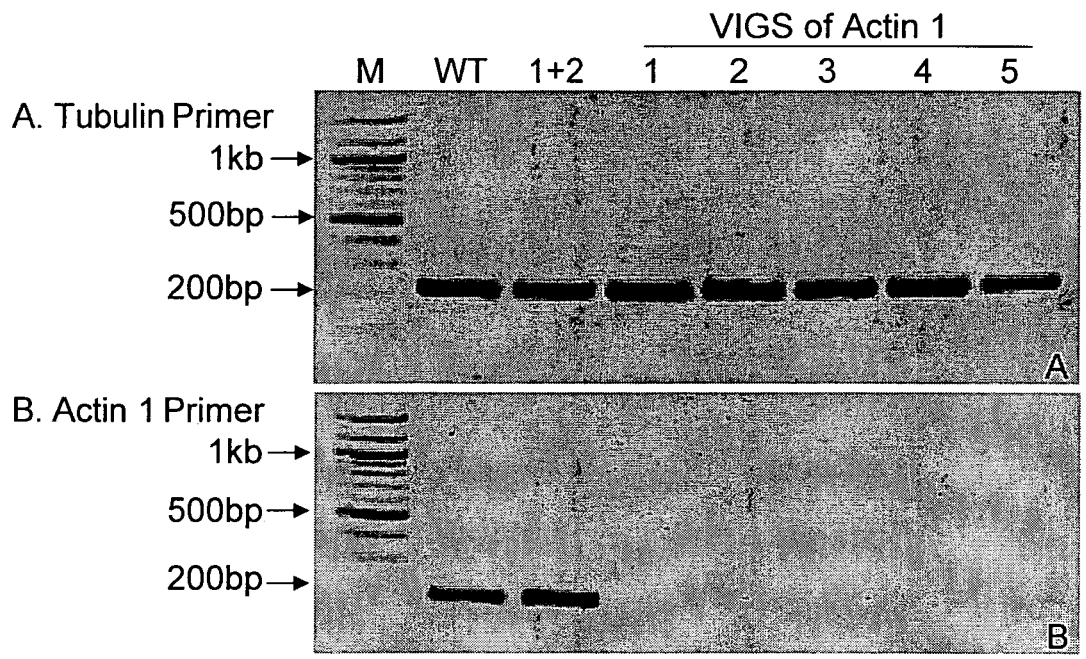
FIGS. 27A and 27B show RT-PCR analysis of GhActin 1 gene expression in cotton fibers.
Figure 28:
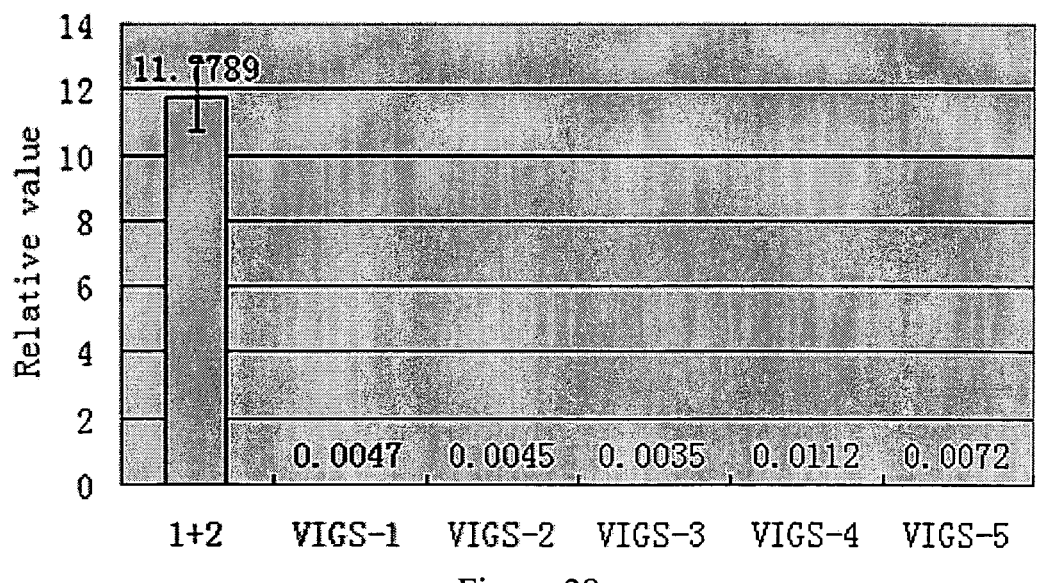
FIG. 28 shows real-time RT-PCR Analysis of VIGS-Actin 1 in cotton fibers. Relative value of GhActin 1 gene expression in 14 days after infected fibers is shown as a percentage of GhTubulin expression activity (see Materials and Methods Example 12). The result of real-time PCR shows that VIGS of Actin 1 caused significant reduction its mRNA.

GhActin1: Actin expression in cotton ovule culture is shown in FIGS. 22A and 22B. A strong band was detected in wild-type control fiber and psTRV1+psTRV2 control fiber, whereas no or weak signals were detected in the VIGS-Actin 1 lines (FIGS. 27A, 27B). The results of real-time PCR revealed that the expression levels of the GhActin 1 RNAi resulted in complete GhActin 1 silence in lines VIGS-1, VIGS-2, VIGS-3, VIGS-4 and VIGS-5 (FIG. 28). The results of SEM suggested that the length of fibers was much shorter than that in psTRV1+psTRV2 at the same stages and the surface of trichome was rough and wrinkled (FIGS. 23A-11D and FIGS. 23E-23H). All VIGS-GhActin 1 showed a short-fiber phenotype and the reduction of Actin 1 transcript levels, indicating that the phonetype was a result of the Actin 1

TABLE 4

Primers Used in Gene-Specific Real-Time PCR Analysis

| Genes | Primer (SEQ ID NO:) |
|---|---|
| GhActin 1 | 5'-ATATTCTAGAAGAAGAACTATGAGTTGCCT-3' (forward) (32)<br>5'-ATGGGATCCCGTAGAGATCCTTCCTGATAT-3' (reverse) (33) |
| GhADF 1 | 5'-TATCTGTGGATTCTTATGGGGTATGTGTGT-3' (forward) (34)<br>5'-AGACCTTCTAACTTGATAACCAAATCTTTG-3' (reverse) (35) |
| GhCTR 1 | 5'-TGAATCCTCAAGTGGCTGCCATTATTGAGG-3' (forward) (36)<br>5'-GCATGTACCCTTGGGAAGCATATAATGTTA-3' (reverse) (37) |
| GhDELLA 1 | 5'-GCAGTTGGAGGAGGTTATGTGTAATGTTCA-3' (forward) (38)<br>5'-TCCGATTGATGTTGTCGAAATCCAACGTCG-3' (reverse) (39) |
| GhAlpha-tubulin 1 | 5'-TCATTTCAGCTGAGAAGGCTTACCATGAGC-3' (forward) (40)<br>5'-TGGTAGTTGATACCGCACTTGAATCCAGTA-3' (reverse) (41) |
| GhBeta-tubulin 1 | 5'-ATGATGTGCGCGGCTGATCCTCGTCA-3' (forward) (42)<br>5'-CATCTCTTGTATCGATGTCGAGTTCC-3' (reverse) (43) |
| GhMADS 9 | 5'-TGCTGATGGATATAGTTTAGTCGTGA-3' (forward) (44)<br>5'-ACAACTTTCTAAGTAGCAGAAAGAAG-3' (reverse) (45) |
| GhMYB 5 | 5'-GTGGTCGAAAATTGCACAACACTTGCCTGG-3' (forward) (46)<br>5'-GCTTATGTTGCTGATACGATCATTGTAGGT-3' (reverse) (47) |
| GhMYB 6 | 5'-AGATGGATAAATTACTTAAGACCAGATATC-3' (forward) (48)<br>5'-ATCTACCAGCTATCAGTGACCACCTAACAC-3' (reverse) (49) |
| GhTubulin | 5'-GATGTMTGCCCAAGGATGTTAATGC-3' (forward) (50)<br>5'-ATGAGATCAAACTTGTGGTCAATGCG-3' (reverse) (51) |
| GhUbiquitin | 5'-CTGAATCTTCGCTTTCACGTTATC-3' (forward) (52)<br>5'-GGGATGCAAATCTTCGTGAAAAC-3' (reverse) (53) |

Example 8

Function of Cotton Genes in Fiber Development

To test the function of cotton genes in fiber development, we chose GhActin 1, GhADF 1, GhCTR 1, GhDELLA 1, GhAlpha-tubulin 1, GhBeta-tubulin 1, GhMADS 9, GhMBY 5 and GhMBY6. VIGS (virus-induced gene silencing) approaches using RNAi technology were employed. The 500-650 bp fragment of a candidate gene was constructed into a vector comprising a chemically synthesized tobacco rattle virus (sTRV) RNA2 sequence to produce a modified sTRV2 vector. To understand whether the reduced mRNAs of all of the candidate genes, we analyzed the expression levels of all the candidate genes in fiber by real-time quantitative SYBR-reduction caused by GhActin 1 silence. These data suggest that GhActin 1 is one of the dominant and functional gene in fiber elongation.

Figure 29:
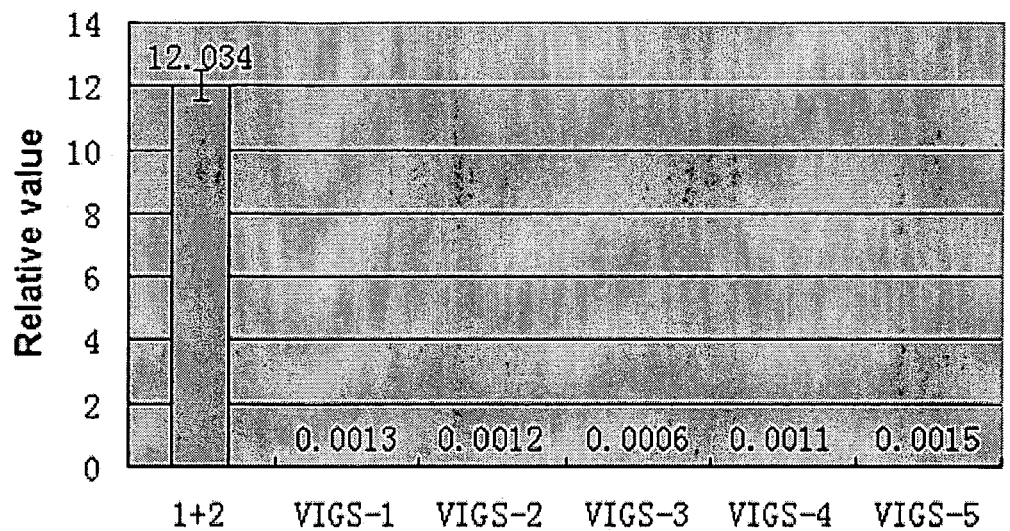
FIG. 29 shows real-time RT-PCR Analysis of VIGS-ADF 1 in cotton fibers. Relative value of GhADF 1 gene expression in 14 days after infected fibers is shown as a percentage of GhTubulin expression activity (see Materials and Methods Example 12). The result of real-time PCR shows that VIGS of ADF 1 caused significant reduction its mRNA.

GhADF 1: The results of real-time PCR revealed that the expression levels of the GhADF 1 RNAi resulted in complete GhADF 1 silence in lines VIGS-1, VIGS-2, VIGS-3, VIGS-4 and VIGS-5 (FIG. 29). The results of SEM showed that the length of fibers was same as psTRV1+psTRV2 at the same stages (FIGS. 23A-23D and FIGS. 23I-23L). Although all VIGS-GhADF 1 showed the reduction of ADF 1 transcript levels, the length of fibers was not any changed. These data suggest that GhADF 1 is not related with the fiber elongation.

Figure 30:
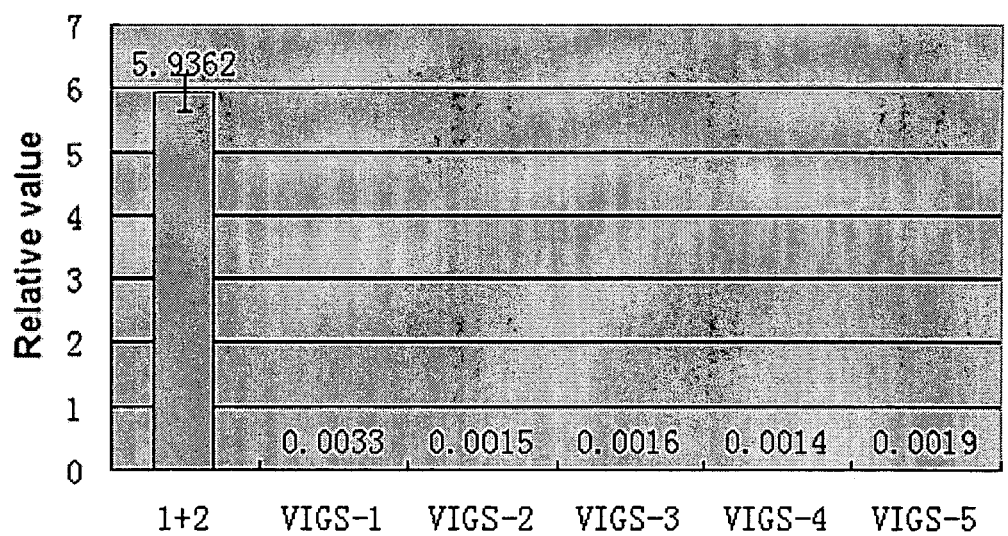
FIG. 30 shows real-time RT-PCR Analysis of VIGS-CTR 1 in cotton fibers. Relative value of GhCTR 1 gene expression in 14 days after infected fibers is shown as a percentage of GhTubulin expression activity (see Materials and Methods Example 12). The result of real-time PCR shows that VIGS of CTR 1 caused significant reduction its mRNA.

GhCTR 1: The results of real-time PCR revealed that the expression levels of the GhCTR 1 RNAi resulted in complete GhCTR 1 silence in lines VIGS-1, VIGS-2, VIGS-3, VIGS-4 and VIGS-5 (FIG. 30). The results of SEM suggested that the length of fibers was much shorter than that in psTRV1+psTRV2 at the same stages (FIGS. 24A and 24B). All VIGS-GhCTR 1, showed a short-fiber phenotype and the reduction of CTR 1 transcript levels, indicating that the phenotype was a result of the CTR 1 reduction caused by GhCTR 1 silence. These data suggest that GhCTR 1 is one of the dominant and functional gene in fiber elongation.

Figure 31:
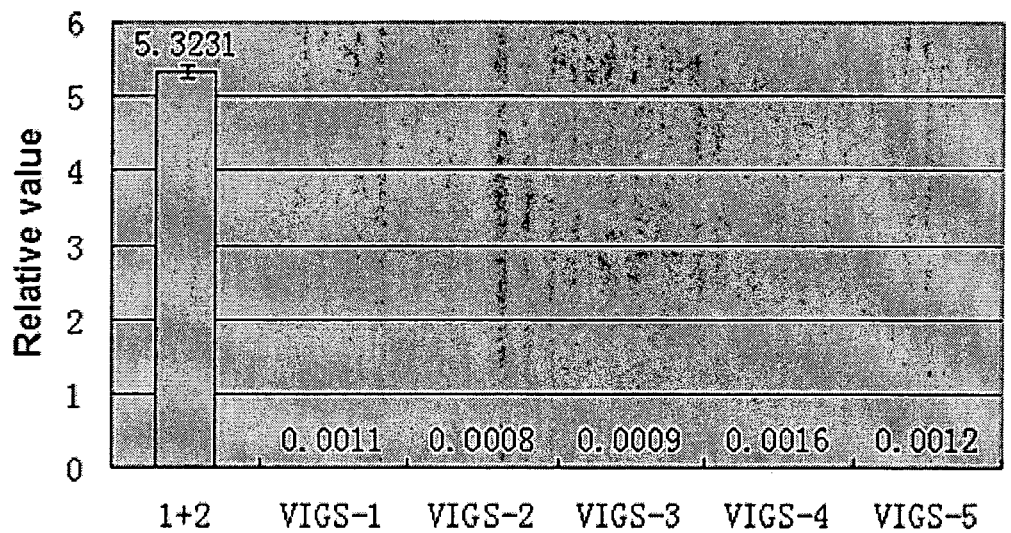
FIG. 31 shows real-time. RT-PCR Analysis of VIGS-DELLA 1 in cotton fibers. Relative value of GhDELLA 1 gene expression in 14 days after infected fibers is shown as a percentage of GhTubulin expression activity (see Materials and Methods Example 12). The result of real-time PCR shows that VIGS of DELLA 1 caused significant reduction its mRNA.

GhDELLA 1: The results of real-time. PCR revealed that the expression levels of the GhDELLA 1 RNAi resulted in complete GhDELLA 1 silence in lines VIGS-1, VIGS-2, VIGS-3, VIGS-4 and VIGS-5 (FIG. 31). The results of SEM showed that the length of fibers was same as psTRV1+psTRV2 at the same stages (FIGS. 24A and 24C). Although all VIGS-GhDELLA 1 showed the reduction of DELLA 1 transcript levels, the length of fibers was not any changed. These data suggest that GhDELLA 1 is not related with the fiber elongation.

Figure 32:
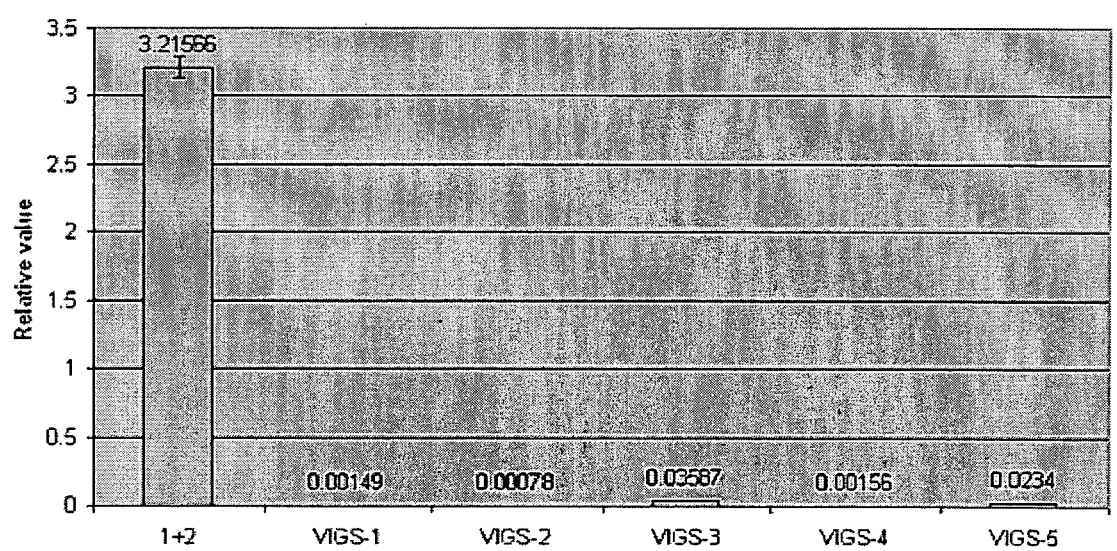
FIG. 32 shows real-time RT-PCR Analysis of VIGS-GhAlpha-tubulin 1 in cotton fibers. Relative value of GhAlpha-tubulin 1 gene expression in 14 days after infected fibers is shown as a percentage of GhUbiquitin expression activity (see Materials and Methods Example 12). The result of real-time PCR shows that VIGS of GhAlphy-tubulin 1 caused significant reduction its mRNA.

GhAlpha-tubulin 1: The results of real-time PCR revealed that the expression levels of the GhAlpha-tubulin 1 RNAi resulted in complete GhAlpha-tubulin 1 silence in lines VIGS-1, VIGS-2, VIGS-3, VIGS-4 and VIGS-5 (FIG. 32). The results of SEM suggested that the length of fibers was shorter than that in psTRV1+psTRV2 at the same stages and the surface of trichome was rough and wrinkled (FIGS. 25A and 25B). All VIGS-GhAlpha-tubulin 1 showed a short-fiber phenotype and the reduction of Alpha-tubulin 1 transcript levels, indicating that the phenotype was a result of the Alpha-tubulin 1 reduction caused by GhAlpha-tubulin 1 silence. These data suggest that GhAlpha-tubulin 1 is one of the dominant and functional gene in fiber elongation.

Figure 33:
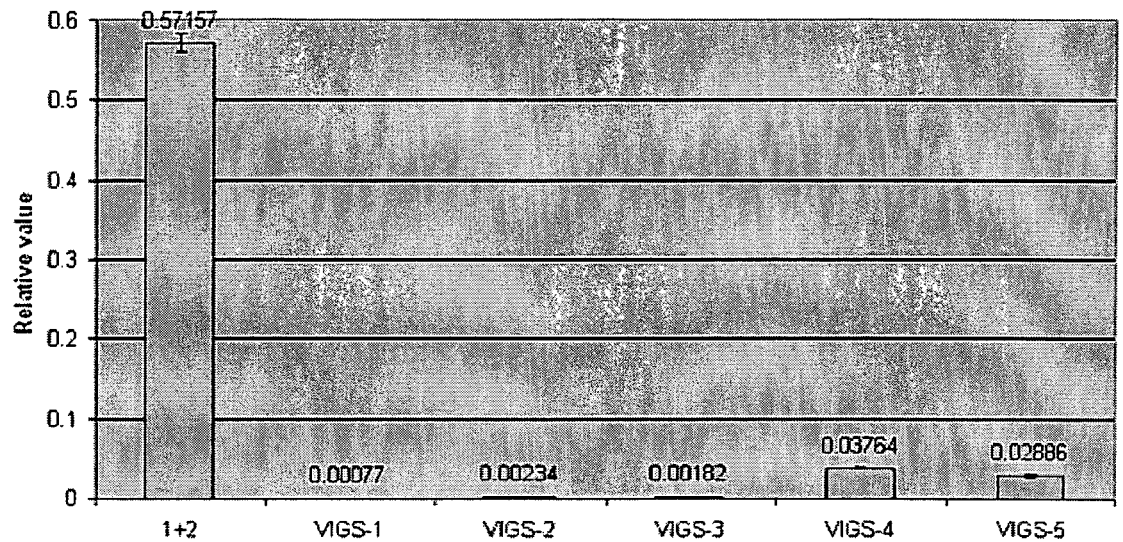
FIG. 33 shows real-time RT-PCR Analysis of VIGS-Gh-Beta-tubulin 1 in cotton fibers. Relative value of GhBeta-tubulin 1 gene expression in 14 days after infected fibers is shown as a percentage of GhUbiquitin expression activity (see Materials and Methods Example 12). The result of real-time PCR shows that VIGS of GhBeta-tubulin 1 caused significant reduction its mRNA.

GhBeta-tubulin 1: The results of real-time PCR revealed that the expression levels of the GhBeta-tubulin 1 RNAi resulted in complete GhBeta-tubulin 1 silence in lines VIGS-1, VIGS-2, VIGS-3, VIGS-4 and VIGS-5 (FIG. 33). The results of SEM suggested that the length of fibers was shorter than that in psTRV 1+psTRV2 at the same stages and the surface of trichome was rough and wrinkled (FIGS. 25A and 25C). All VIGS-GhBeta-tubulin 1 showed a short-fiber phenotype and the reduction of Beta-tubulin 1 transcript levels, indicating that the phenotype was a result of the Beta-tubulin 1 reduction caused by GhBeta-tubulin 1 silence. These data suggest that GhBeta-tubulin 1 is one of the dominant and functional genes in fiber elongation.

Figure 26D:
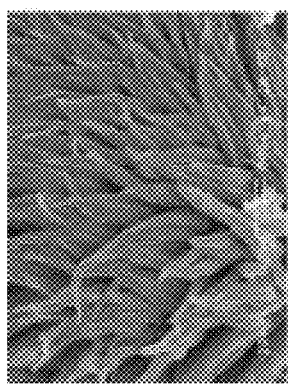
FIGS. 26A-26D show scanning electron micrographs of the ovule surface of VIGS-GhMADS 9, VIGS-GhMBY5, VIGS-GhMBY6 and psTRV1+psTRV2.
Figure 26C:
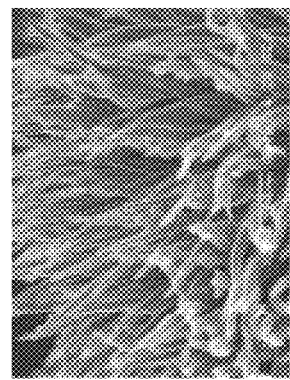
Figure 26B:
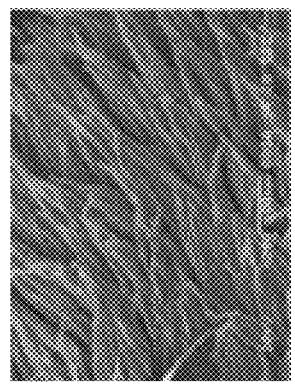
Figure 26A:
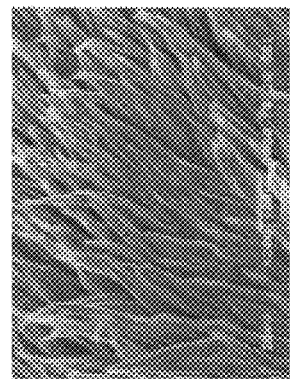
Figure 34:
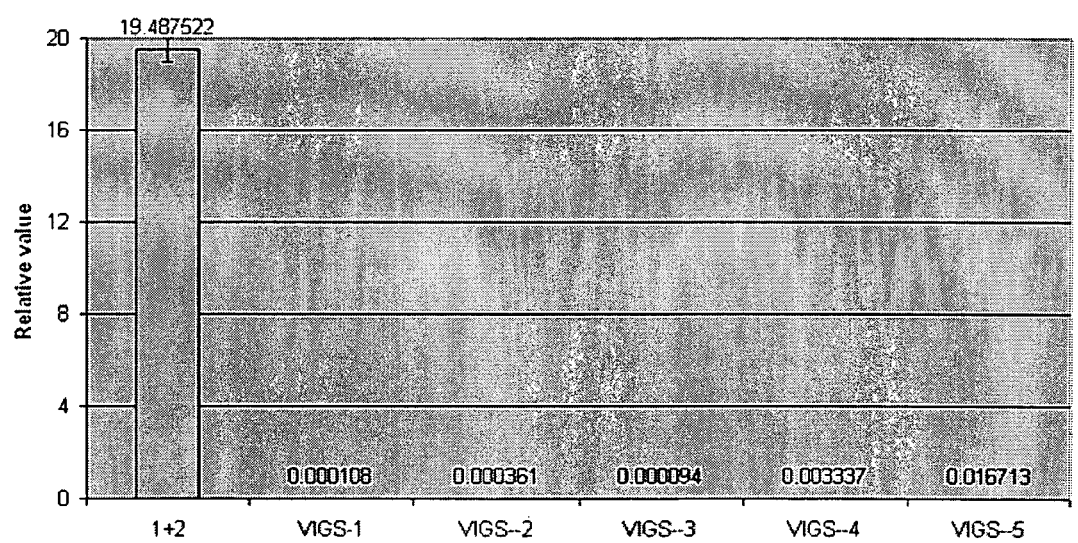
FIG. 34 shows real-time RT-PCR Analysis of VIGS-Gh-MADS 9 in cotton fibers. Relative value of GhMADS 9 gene expression in 14 days after infected fibers is shown as a percentage of GhUbiquitin expression activity (see Materials and Methods Example 12). The result of real-time PCR shows that VIGS of GhMADS 9 caused significant reduction its mRNA.

GhMADS 9: The results of real-time PCR revealed that the expression levels of the GhMADS 9 RNAi resulted in complete GhMADS 9 silence in lines VIGS-1, VIGS-2, VIGS-3, VIGS-4 and VIGS-5 (FIG. 34). The results of SEM suggested that the length of fibers was longer than that in psTRV1+psTRV2 at the same stages (FIGS. 26A and 26B). All VIGS-GhMADS 9 showed a long-fiber phenotype and the reduction of MADS 9 transcript levels, indicating that the phenotype was a result of the MADS 9 reduction caused by GhMADS 9 silence. These data suggest that GhMADS 9 is one of the negative regulator in fiber elongation.

Figure 35:
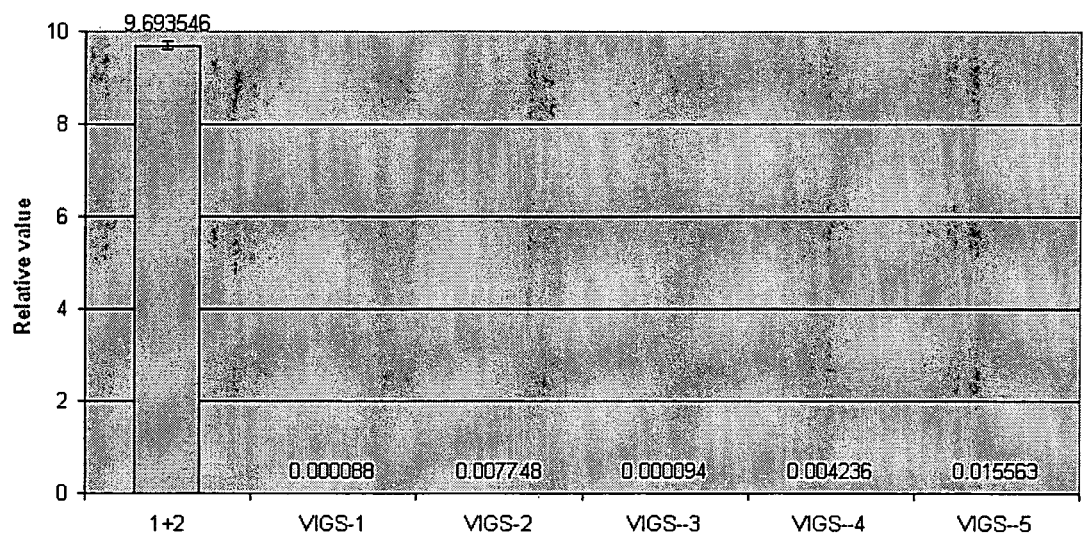
FIG. 35 shows real-time RT-PCR Analysis of VIGS-Gh-MYB 5 in cotton fibers. Relative value of GhMYB 5 gene expression in 14 days after infected fibers is shown as a percentage of GhUbiquitin expression activity (see Materials and Methods Example 12). The result of real-time PCR shows that VIGS of GhMYB 5 caused significant reduction its mRNA.

GhMYB 5: The results of real-time PCR revealed that the expression levels of the GhMYB 5 RNAi resulted in complete GhMYB 5 silence in lines VIGS-1, VIGS-2, VIGS-3, VIGS-4 and VIGS-5 (FIG. 35). The results of SEM showed that the length of fibers was same as psTRV1+psTRV2 at the same stages (FIGS. 26 A and 26C). Although all VIGS-GhMYB 5 showed the reduction of MYB 5 transcript levels, the length of fibers was not any changed. These data suggest that GhMYB 5 is not related with the fiber elongation.

Figure 36:
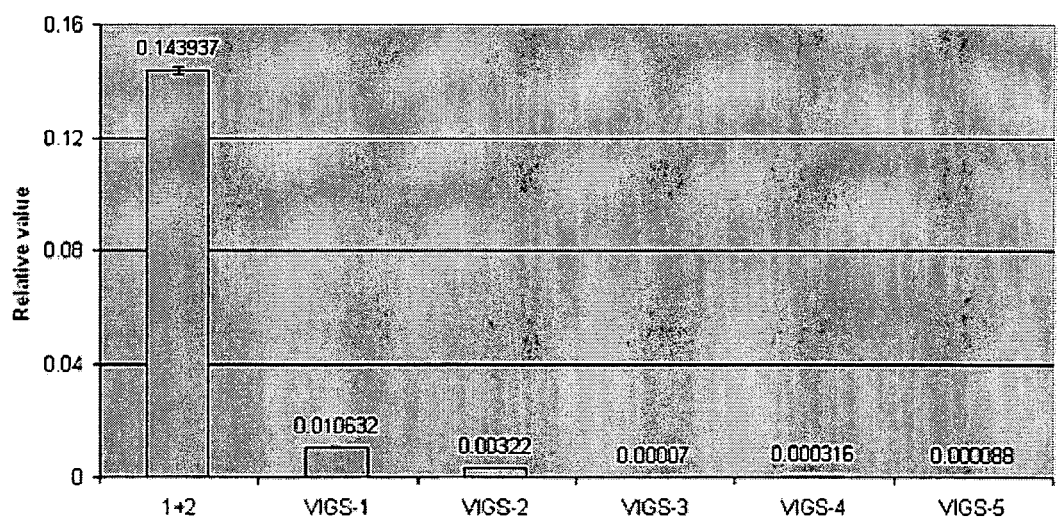
FIG. 36 shows real-time RT-PCR Analysis of VIGS-Gh-MYB 6 in cotton fibers. Relative value of GhMYB 6 gene expression in 14 days after infected fibers is shown as a percentage of GhUbiquitin expression activity (see Materials and Methods Example 12). The result of real-time PCR shows that VIGS of GhMYB 6 caused significant reduction its mRNA.
Figure 37:
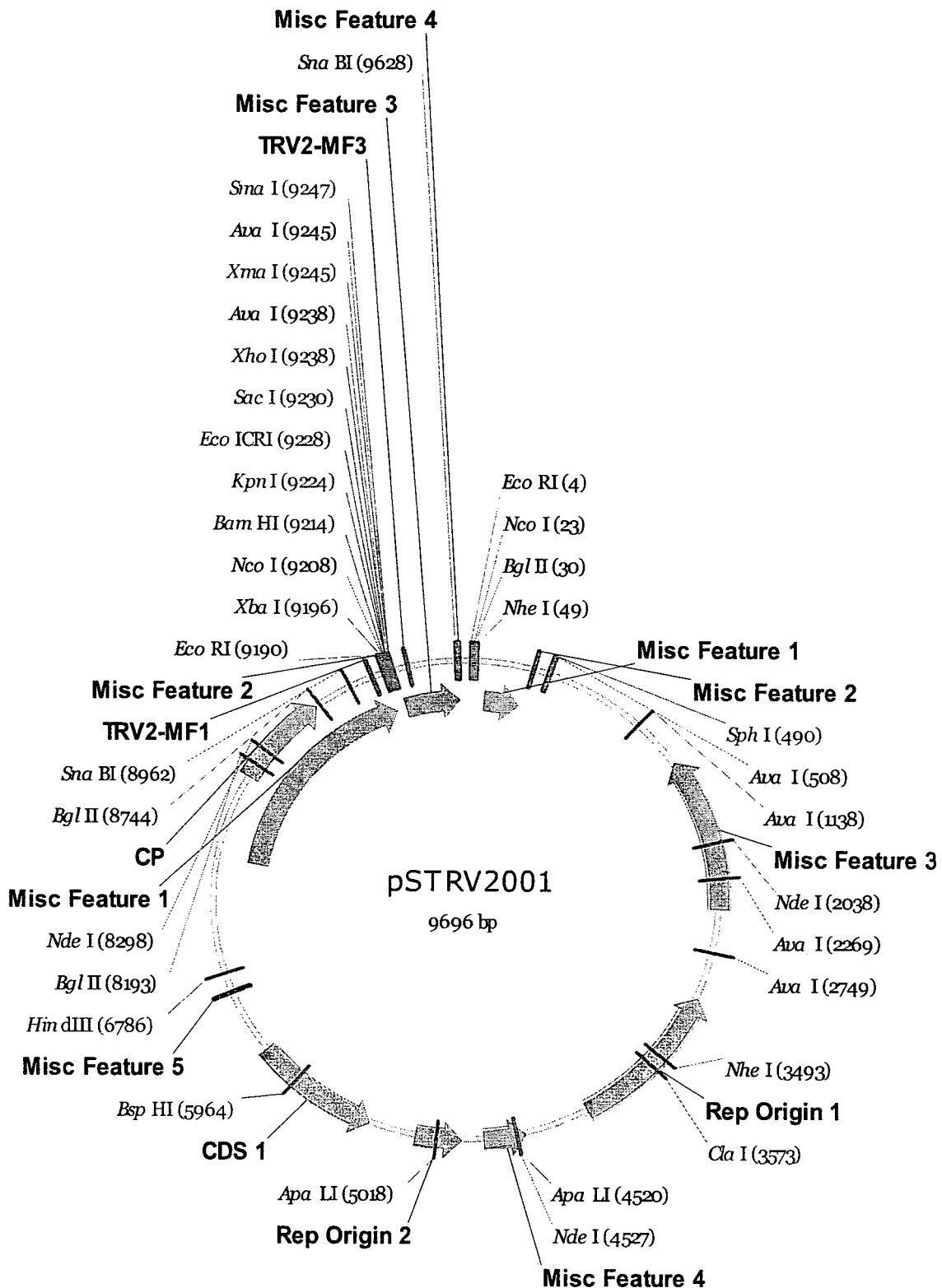
FIG. 37 shows the map for psTRV2001. The sequence for sTRV2 extends from nucleotide 6785 through nucleotide 9696 as set forth in SEQ ID NO:82.

GhMYB 6: The results of real-time PCR revealed that the expression levels of the GhMYB 6 RNAi resulted in complete GhMYB 6 silence in lines VIGS-1, VIGS-2, VIGS-3, VIGS-4 and VIGS-5 (FIG. 36). The results of SEM showed that the length of fibers was same as psTRV1+psTRV2 at the same stages (FIGS. 26A and 26D). Although all VIGS-GhMYB 6 showed the reduction of MYB 6 transcript levels, the length of fibers was not any changed. These data suggest that GhMYB 6 is not related with the fiber elongation.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

It will be appreciated that the methods and compositions of the instant invention can be incorporated in the form of a variety of embodiments, only a few of which are disclosed herein. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

Alonso-Cantabrana, H. et al. (2007). Common regulatory networks in leaf and fruit patterning revealed by mutations in the *Arabidopsis* ASYMMETRIC LEAVES1 gene. *Development* 134:2663-2671.

Baulcombe, D. (2004). RNA silencing in plants. Nature 431:356-363.

Beclin, C. et al. (2002). A branched pathway for transgene-induced RNA silencing in plants. *Curr Biol* 12:684-688.

Beasley, C. A. and Ting, I. P. (1973). The effects of plant growth substances on in vitro fiber development from fertilized cotton ovules. *Amer J Bot* 60:130-139.

Brigneti, G. et al. (2004). Virus-induced gene silencing in Solanum species. *Plant J* 39:264-272.

Burch-Smith, T. M. et al. (2004). Applications and advantages of virus-induced gene silencing for gene function studies in plants. *Plant J* 39:734-746.

Burch-Smith, T. M. (2006). Efficient virus-induced gene silencing in *Arabidopsis. Plant Physiol* 142:21-27.

Chen, J. C. et al. (2005). Silencing a prohibitin alters plant development and senescence. *Plant J* 44:16-24.

Chung, E. et al. (2004). A method of high frequency virus-induced gene silencing in chili pepper (*Capsicum annuum* L. cv. Bukang). *Mol Cells* 17:377-380.

Fu, D. Q. et al. (2005). Virus-induced gene silencing in tomato fruit. *Plant. J* 43:299-308.

Guo, M. et al. (2008). Direct repression of KNOX loci by the ASYMMETRIC LEAVES1 complex of *Arabidopsis*. *Plant Cell* 20:48-58.

Kidner, C. A. and Martienssen, R. A. (2004). Spatially restricted microRNA directs leaf polarity through ARGONAUTE1. *Nature* 428:81-84.

Kim. G. et al. (2002). The ANGUSTIFOLIA gene of *Arabidopsis*, a plant CtBP gene, regulates leaf-cell expansion, the arrangement of cortical microtubules in leaf cells and expression of a gene involved in cell-wall formation. *EMBO J* 21:1267-4279.

Lee, J. J. et al. (2007). A method of high frequency virus-induced gene silencing in chili pepper (*Capsicum annuum* L. cv. Bukang). *Mol Cells* 17:377-380.

Liu, Y. et al. (2002). Virus-induced gene silencing in tomato. *Plant J* 31:777-786.

Liu, Y. et al. (2004). Virus induced gene silencing of a DEFICIENS ortholog in Nicotiana benthamiana. *Plant Mol Biol* 54:701-711.

MacFarlane, S. A. and Popovich, A. H. (2000). Efficient expression of foreign proteins in roots from tobravirus vectors. *Virology* 267:29-35.

McHale, N. A. et al. (2004). PHANTASTICA regulates development of the adaxial mesophyll in Nicotiana leaves. *Plant Cell* 16:1251-1262.

Morel, J. B. et al. (2002). Fertile hypomorphic ARGONAUTE (ago1) mutants impaired in post-transcriptional gene silencing and virus resistance. *Plant Cell* 14:629-639.

Nurmberg, P. L. et al. (2007). The developmental selector AS1 is an evolutionarily conserved regulator of the plant immune response. *Proc Natl Acad Sci USA* 104:18795-18800.

Ori, N. et al. (2000). Mechanisms that control knox gene expression in the *Arabidopsis* shoot. *Development* 127:5523-5532.

Ruiz, M. T. et al. (1998). Initiation and maintenance of virus-induced gene silencing. *Plant Cell* 10:937-946.

Shi, B. J. et al. (1997). Plasmid vector for cloning infectious cDNAs from plant RNA viruses: high infectivity of cDNA clones of tomato aspermy cucumovirus. *J Gen Virol* 78 (Pt 5):1181-1185.

Stipanovic, R. D. et al. (1988). Terpenoid aldehydes in upland cottons: analysis by aniline and HPLC methods. *J Agric Food Chem* 36:509-515.

Sun, Y. et al. (2002). ASYMMETRIC LEAVES1, an *Arabidopsis* gene that is involved in the control of cell differentiation in leaves. *Planta* 214:694-702.

Udall, J. A. et al. (2006). A global assembly of cotton ESTs. *Genome Res* 16:441-450.

Valentine, T. et al. (2004). Efficient virus-induced gene silencing in roots using a modified tobacco rattle virus vector. *Plant Physiol* 136:3999-4009.

Wan, C. Y. and Willdns, T. A. (1994). A modified hot borate method significantly enhances the yield of high quality RNA from cotton (*Gossypium hirsutum* L.). *Anal Biochem* 223:7-12.

---

What is claimed is:

1. A method of virus-induced gene silencing (VIGS) in cotton comprising:
   (a) inserting a nucleic acid comprising a first silencing sequence capable of silencing a first desired gene into a vector comprising a tobacco rattle virus (TRV) RNA2 sequence to produce a vector comprising a modified TRV RNA2 sequence;
   (b) preparing a mixed culture of *Agrobacterium* comprising *Agrobacterium* containing a vector comprising a modified TRV RNA1 sequence and *Agrobacterium* containing the vector comprising the modified TRV RNA2 sequence, wherein the modified TRV RNA1 sequence is a TRV RNA1 sequence into which an intron has been inserted, wherein the insertion is within positions corresponding to 10919-10922 of SEQ ID NO: 1;
   (c) introducing the mixed culture of *Agrobacterium* into plant tissue of cotton to produce infected plant tissue; and
   (d) growing the infected plant tissue for a sufficient to produce systemic TRV infection in the infected plants and to thereby induce gene silencing of the first desired gene.

2. The method of claim 1, wherein the vector comprising TRV RNA2 and the vector comprising TRV RNA1 are synthetic plant vectors.

3. The method of claim 1, wherein the first silencing sequence is a sequence of a sense strand of the first desired gene.

4. The method of claim 1, wherein the first silencing sequence is a sequence of an antisense strand of the first desired gene.

5. The method of claim 1, wherein the first silencing sequence encodes a short hairpin RNA (shRNA) or a precursor microRNA (miRNA).

6. The method of claim 1, wherein the nucleic acid further comprises a second silencing sequence capable of silencing a second desired gene.

7. The method of claim 1, wherein the nucleic acid comprises multiple silencing sequences capable of silencing multiple desired genes.

8. The method of claim 1, wherein the desired gene is a candidate transcription factor gene.

9. The method of claim 1, wherein the desired gene is a candidate gene in smRNA biosynthesis.

10. The method of claim 1, wherein the desired gene is selected from the group consisting of (a) a candidate gene in a proanthocyanidin or anthocyanidin biosynthetic pathway, (b) a candidate gene in cotton fiber development, (c) a candidate gene in a chlorophyll or arotenoid biosynthetic pathway and (d) a candidate gene in a flavonoid biosynthetic pathway.

11. The method of claim 10, wherein the candidate gene in cotton fiber development is a candidate gene in cotton fiber initiation, elongation, secondary wall deposition, maturation or seed development.

12. The method of claim 1, wherein the cotton tissue is a cotton plant, a cotton seedling, a cotton ovule or cotton fiber.

13. The method of claim 1, wherein the cotton is a diploid variety, a tetraploid variety, a variety of an inter-species cross or a variety of an interspecies cross.

* * * * *

SEQUENCE LISTING

```
<160> NUMBER OF SEQ ID NOS: 82

<210> SEQ ID NO 1
<211> LENGTH: 17164
<212> TYPE: DNA
<213> ORGANISM: Artificial
<220> FEATURE:
<223> OTHER INFORMATION: sequence of synthetic pSTRV1001 vector

<400> SEQUENCE: 1
ctcgaatttc cccgatcgtt caaacatttg gcaataaagt ttcttaagat tgaatcctgt      60
tgccggtctt gcgatgatta tcatataatt tctgttgaat tacgttaagc atgtaataat     120
taacatgtaa tgcatgacgt tatttatgag atgggttttt atgattagag tcccgcaatt     180
atacatttaa tacgcgatag aaaacaaaat atagcgcgca aactaggata aattatcgcg     240
cgcggtgtca tctatgttac tagatcggga attcactggc cgtcgtttta caacgtcgtg     300
actgggaaaa ccctggcgtt acccaactta atcgccttgc agcacatccc cctttcgcca     360
gctggcgtaa tagcgaagag gcccgcaccg atcgcccttc ccaacagttg cgcagcctga     420
atggcgcccg ctcctttcgc tttcttccct tcctttctcg ccacgttcgc cggctttccc     480
cgtcaagctc taaatcgggg gctcccttta gggttccgat ttagtgcttt acggcacctc     540
gaccccaaaa aacttgattt gggtgatggt tcacgtagtg ggccatcgcc ctgatagacg     600
gtttttcgcc ctttgacgtt ggagtccacg ttctttaata gtggactctt gttccaaact     660 ggaacaaac tcaaccctat ctcgggctat tctttttgatt tataagggat tttgccgatt     720
tcggaaccac catcaaacag gatttttcgcc tgctggggca aaccagcgtg gaccgcttgc     780
```

```
tgcaactctc tcagggccag gcggtgaagg gcaatcagct gttgcccgtc tcactggtga    840
aaagaaaaac cacccagta cattaaaaac gtccgcaatg tgttattaag ttgtctaagc    900
gtcaatttgt ttacaccaca atatatcctg ccaccagcca gccaacagct ccccgaccgg    960
cagctcggca caaaatcacc actcgataca ggcagcccat cagtccggga cggcgtcagc   1020
gggagagccg ttgtaaggcg gcagactttg ctcatgttac cgatgctatt cggaagaacg   1080
gcaactaagc tgccgggttt gaaacacgga tgatctcgcg gagggtagca tgttgattgt   1140
aacgatgaca gagcgttgct gcctgtgatc aaatatcatc tccctcgcag agatccgaat   1200
tatcagcctt cttattcatt tctcgcttaa ccgtgacagg ctgtcgatct tgagaactat   1260
gccgacataa taggaaatcg ctggataaag ccgctgagga agctgagtgg cgctatttct   1320
ttagaagtga acgttgacga tatcaactcc cctatccatt gctcaccgaa tggtacaggt   1380
cggggacccg aagttccgac tgtcggcctg atgcatcccc ggctgatcga ccccagatct   1440
ggggctgaga agcccagta aggaaacaac tgtaggttcg agtcgcgaga tccccggaa    1500 ccaaaggaag taggttaaac ccgctccgat caggccgagc cacgccaggc cgagaacatt   1560
ggttcctgta ggcatcggga ttggcggatc aaacactaaa gctactggaa cgagcagaag   1620
tcctccggcc gccagttgcc aggcggtaaa ggtgagcaga ggcacgggag ttgccactt    1680 gcgggtcagc acggttccga acgccatgga aaccgccccc gccaggcccg ctgcgacgcc   1740
gacaggatct agcgctgcgt ttggtgtcaa caccaacagc gccacgcccg cagttccgca   1800
aatagccccc aggaccgcca tcaatcgtat cgggctacct agcagagcgg cagagatgaa   1860
cacgaccatc agcggctgca cagcgcctac cgtcgccgcg accccgcccg gcaggcggta   1920
gaccgaaata acaacaagc tccagaatag cgaaatatta agtgcgccga ggatgaagat    1980
gcgcatccac cagattcccg ttggaatctg tcggacgatc atcacgagca ataaacccgc   2040
cggcaacgcc cgcagcagca taccggcgac ccctcggcct cgctgttcgg gctccacgaa   2100
aacgccggac agatgcgcct tgtgagcgtc cttggggccg tcctcctgtt tgaagaccga   2160
cagcccaatg atctcgccgt cgatgtaggc gccgaatgcc acggcatctc gcaaccgttc   2220
agcgaacgcc tccatgggct ttttctcctc gtgctcgtaa acggacccga acatctctgg   2280
agctttcttc agggccgaca atcggatctc gcggaaatcc tgcacgtcgg ccgctccaag   2340
ccgtcgaatc tgagccttaa tcacaattgt caattttaat cctctgttta tcggcagttc   2400
gtagagcgcg ccgtgcgtcc cgagcgatac tgagcgaagc aagtgcgtcg agcagtgccc   2460
gcttgttcct gaaatgccag taaagcgctg gctgctgaac ccccagccgg aactgacccc   2520
acaaggccct agcgtttgca atgcaccagg tcatcattga cccaggcgtg ttccaccagg   2580
ccgctgcctc gcaactcttc gcaggcttcg ccgacctgct cgcgccactt cttcacgcgg   2640
gtggaatccg atccgcacat gaggcggaag gtttccagct tgagcgggta cggctcccgg   2700
tgcgagctga aatagtcgaa catccgtcgg gccgtcggcg acagcttgcg gtacttctcc   2760
catatgaatt tcgtgtagtg gtcgccagca aacagcacga cgatttcctc gtcgatcagg   2820
acctggcaac gggacgtttt cttgccacgg tccaggacgc ggaagcggtg cagcagcgac   2880
accgattcca ggtgcccaac gcggtcggac gtgaagccca tcgccgtcgc ctgtaggcgc   2940
gacaggcatt cctcggcctt cgtgtaatac cggccattga tcgaccagcc caggtcctgg   3000
caaagctcgt agaacgtgaa ggtgatcggc tcgccgatag gggtgcgctt cgcgtactcc   3060
aacacctgct gccacaccag ttcgtcatcg tcggcccgca gctcgacgcc ggtgtaggtg   3120
atcttcacgt ccttgttgac gtggaaaatg accttgtttt gcagcgcctc gcgcgggatt   3180
```

```
ttcttgttgc gcgtggtgaa cagggcagag cgggccgtgt cgtttggcat cgctcgcatc    3240
gtgtccggcc acggcgcaat atcgaacaag gaaagctgca tttccttgat ctgctgcttc    3300
gtgtgtttca gcaacgcggc ctgcttggcc tcgctgacct gttttgccag gtcctcgccg    3360 gcggttttc  gcttcttggt cgtcatagtt cctcgcgtgt cgatggtcat cgacttcgcc    3420
aaacctgccg cctcctgttc gagacgacgc gaacgctcca cggcggccga tggcgcgggc    3480
agggcagggg gagccagttg cacgctgtcg cgctcgatct tggccgtagc ttgctggacc    3540
atcgagccga cggactggaa ggtttcgcgg ggcgcacgca tgacggtgcg gcttgcgatg    3600
gtttcggcat cctcggcgga aaaccccgcg tcgatcagtt cttgcctgta tgccttccgg    3660
tcaaacgtcc gattcattca ccctccttgc gggattgccc cgactcacgc cggggcaatg    3720
tgcccttatt cctgatttga cccgcctggt gccttggtgt ccagataatc caccttatcg    3780
gcaatgaagt cggtcccgta gaccgtctgg ccgtccttct cgtacttggt attccgaatc    3840
ttgccctgca cgaataccag cgaccccttg cccaaatact tgccgtgggc ctcggcctga    3900
gagccaaaac acttgatgcg gaagaagtcg gtgcgctcct gcttgtcgcc ggcatcgttg    3960
cgccacatct aggtactaaa acaattcatc cagtaaaata taatatttta ttttctccca    4020
atcaggcttg atccccagta agtcaaaaaa tagctcgaca tactgttctt ccccgatatc    4080
ctccctgatc gaccggacgc agaaggcaat gtcataccac ttgtccgccc tgccgcttct    4140
cccaagatca ataaagccac ttactttgcc atctttcaca aagatgttgc tgtctcccag    4200
gtcgccgtgg gaaaagacaa gttcctcttc gggcttttcc gtctttaaaa aatcatacag    4260
ctcgcgcgga tctttaaatg gagtgtcttc ttcccagttt tcgcaatcca catcggccag    4320
atcgttattc agtaagtaat ccaattcggc taagcggctg tctaagctat tcgtataggg    4380
acaatccgat atgtcgatgg agtgaaagag cctgatgcac tccgcataca gctcgataat    4440 ctttttcaggg ctttgttcat cttcatactc ttccgagcaa aggacgccat cggcctcact   4500
catgagcaga ttgctccagc catcatgccg ttcaaagtgc aggacctttg aacaggcag     4560 cttttccttcc agccatagca tcatgtcctt ttcccgttcc acatcatagg tggtccctt    4620 ataccggctg tccgtcattt ttaaatatag gttttcattt tctcccacca gcttatatac    4680
cttagcagga gacattcctt ccgtatcttt tacgcagcgg tattttttcga tcagttttt    4740 caattccggt gatattctca ttttagccat ttattatttc cttcctcttt tctacagtat    4800
ttaaagatac cccaagaagc taattataac aagacgaact ccaattcact gttccttgca    4860
ttctaaaacc ttaaatacca gaaaacagct ttttcaaagt tgttttcaaa gttggcgtat    4920
aacatagtat cgacggagcc gattttgaaa ccacaattat gggtgatgct gccaacttac    4980
tgatttagtg tatgatggtg tttttgaggt gctccagtgg cttctgtgtc tatcagctgt    5040
ccctcctgtt cagctactga cggggtggtg cgtaacggca aaagcaccgc cggacatcag    5100
cgctatctct gctctcactg ccgtaaaaca tggcaactgc agttcactta caccgcttct    5160
caacccggta cgcaccagaa aatcattgat atggccatga atggcgttgg atgccgggca    5220
acagcccgca ttatgggcgt tggcctcaac acgattttac gtcacttaaa aaactcaggc    5280
cgcagtcggt aaccctcgcgc atacagccgg gcagtgacgt catcgtctgc gcggaaatgg    5340
acgaacagtg gggctatgtc ggggctaaat cgcgccagcg ctggctgttt tacgcgtatg    5400
acagtctccg gaagacggtt gttgcgcacg tattcggtga acgcactatg gcgacgctgg    5460
ggcgtcttat gagcctgctg tcaccctttg acgtggtgat atggatgacg gatggctggc    5520
```

```
cgctgtatga atcccgcctg aagggaaagc tgcacgtaat cagcaagcga tatacgcagc    5580
gaattgagcg gcataacctg aatctgaggc agcacctggc acggctggga cggaagtcgc    5640
tgtcgttctc aaaatcggtg gagctgcatg acaaagtcat cgggcattat ctgaacataa    5700
aacactatca ataagttgga gtcattaccc aattatgata gaatttacaa gctataaggt    5760
tattgtcctg ggtttcaagc attagtccat gcaagttttt atgctttgcc cattctatag    5820
atatattgat aagcgcgctg cctatgcctt gcccctgaa atccttacat acggcgatat    5880
cttctatata aagatatat tatcttatca gtattgtcaa tatattcaag gcaatctgcc    5940
tcctcatcct cttcatcctc ttcgtcttgg tagcttttta aatatggcgc ttcatagagt    6000
aattctgtaa aggtccaatt ctcgttttca tacctcggta taatcttacc tatcacctca    6060
aatggttcgc tgggtttatc gcaccccga acacgagcac ggcacccgcg accactatgc    6120
caagaatgcc caaggtaaaa attgccggcc ccgccatgaa gtccgtgaat gccccgacgg    6180
ccgaagtgaa gggcaggccg ccacccaggc cgccgccctc actgcccggc acctggtcgc    6240
tgaatgtcga tgccagcacc tgcggcacgt caatgcttcc gggcgtcgcg ctcgggctga    6300
tcgcccatcc cgttactgcc ccgatcccgg caatggcaag gactgccagc gctgccattt    6360
ttggggtgag gccgttcgcg gccgaggggc gcagcccctg gggggatggg aggcccgcgt    6420
tagcgggccg ggagggttcg agaaggggg gcaccccct tcggcgtgcg cggtcacgcg    6480
cacagggcgc agccctggtt aaaaacaagg tttataaata ttggtttaaa agcaggttaa    6540
aagacaggtt agcggtggcc gaaaaacggg cggaaccct tgcaaatgct ggattttctg    6600
cctgtggaca gcccctcaaa tgtcaatagg tgcgcccctc atctgtcagc actctgcccc    6660
tcaagtgtca aggatcgcgc ccctcatctg tcagtagtcg cgcccctcaa gtgtcaatac    6720
cgcagggcac ttatccccag gcttgtccac atcatctgtg ggaaactcgc gtaaaatcag    6780
gcgttttcgc cgatttgcga ggctggccag ctccacgtcg ccggccgaaa tcgagcctgc    6840
ccctcatctg tcaacgccgc gccgggtgag tcggcccctc aagtgtcaac gtccgccct    6900 catctgtcag tgagggccaa gttttccgcg aggtatccac aacgccggcg ccgcggtgt    6960 ctcgcacacg gcttcgacgg cgtttctggc gcgtttgcag ggccatagac ggccgccagc    7020
ccagcggcga gggcaaccag cccggtgagc gtcgcaaagg cgctcggtct tgccttgctc    7080
gtcggtgatg tacttcacca gctccgcgaa gtcgctcttc ttgatggagc gcatgggga    7140 gtgcttggca atcacgcgca cccccggcc gttttagcgg ctaaaaagt catggctctg    7200 ccctcgggcg gaccacgccc atcatgacct tgccaagctc gtcctgcttc tcttcgatct    7260
tcgccagcag ggcgaggatc gtggcatcac cgaaccgcgc cgtgcgcggg tcgtcggtga    7320
gccagagttt cagcaggccg cccaggcggc ccaggtcgcc attgatgcgg gccagctcgc    7380
ggacgtgctc atagtccacg acgcccgtga ttttgtagcc ctggccgacg gccagcaggt    7440
aggccgacag gctcatgccg gccgccgccg ccttttcctc aatcgctctt cgttcgtctg    7500
gaaggcagta caccttgata ggtgggctgc ccttcctggt tggcttggtt tcatcagcca    7560
tccgcttgcc ctcatctgtt acgccggcgg tagccggcca gcctcgcaga gcaggattcc    7620
cgttgagcac cgccaggtgc gaataaggga cagtgaagaa ggaacacccg ctcgcgggtg    7680
ggcctacttc acctatcctg cccggctgac gccgttggat acaccaagga aagtctacac    7740 gaacccttg gcaaaatcct gtatatcgtg cgaaaaagga tggatatacc gaaaaaatcg    7800
ctataatgac cccgaagcag ggttatgcag cggaaaagcg ccacgcttcc gaagggaga    7860 aaggcggaca ggtatccggt aagcggcagg gtcggaacag gagagcgcac gagggagctt    7920
```

```
ccaggggga   acgcctggta   tctttatagt   cctgtcgggt   ttcgccacct   ctgacttgag    7980
cgtcgatttt   tgtgatgctc   gtcagggggg   cggagcctat   ggaaaaacgc   cagcaacgcg    8040
gccttttttac  ggttcctggc   cttttgctgg   cctttgctc    acatgttctt   tcctgcgtta    8100
tccctgatt    ctgtggataa   ccgtattacc   gcctttgagt   gagctgatac   cgctcgccgc    8160
agccgaacga   ccgagcgcag   cgagtcagtg   agcgaggaag   cggaagagcg   ccagaaggcc    8220
gccagagagg   ccgagcgcgg   ccgtgaggct   tggacgctag   gcagggcat    gaaaaagccc    8280
gtagcgggct   gctacgggcg   tctgacgcgg   tggaaagggg   gaggggatgt   tgtctacatg    8340
gctctgctgt   agtgagtggg   ttgcgctccg   gcagcggtcc   tgatcaatcg   tcacccttcc    8400
tcggtccttc   aacgttcctg   acaacgagcc   tccttttcgc   caatccatcg   acaatcaccg    8460
cgagtccctg   ctcgaacgct   gcgtccggac   cggcttcgtc   gaaggcgtct   atcgcggccc    8520
gcaacagcgg   cgagagcgga   gcctgttcaa   cggtgccgcc   gcgctcgccg   gcatcgctgt    8580
cgccggcctg   ctcctcaagc   acggccccaa   cagtgaagta   gctgattgtc   atcagcgcat    8640
tgacggcgtc   cccggccgaa   aaacccgcct   cgcagaggaa   gcgaagctgc   gcgtcggccg    8700
tttccatctg   cggtgcgccc   ggtcgcgtgc   cggcatggat   gcgcgcgcca   tcgcggtagg    8760
cgagcagcgc   ctgcctgaag   ctgcgggcat   tcccgatcag   aaatgagcgc   cagtcgtcgt    8820
cggctctcgg   caccgaatgc   gtatgattct   ccgccagcat   ggcttcggcc   agtgcgtcga    8880
gcagcgcccg   cttgttcctg   aagtgccagt   aaagcgccgg   ctgctgaacc   cccaaccgtt    8940
ccgccagttt   gcgtgtcgtc   agaccgtcta   cgccgacctc   gttcaacagg   tccaggggcgg   9000
cacgatcac    tgtattcggc   tgcaactttg   tcatgcttga   cactttatca   ctgataaaca    9060
taatatgtcc   accaacttat   cagtgataaa   gaatccgcgc   gttcaatcgg   accagcggag    9120
gctggtccgg   aggccagacg   tgaaacccaa   cataccctg    atcgtaattc   tgagcactgt    9180
cgcgctcgac   gctgtcggca   tcggcctgat   tatgccggtg   ctgccgggcc   tcctgcgcga    9240
tctggttcac   tcgaacgacg   tcaccgccca   ctatggcatt   ctgctggcgc   tgtatgcgtt    9300
ggtgcaattt   gcctgcgcac   ctgtgctggg   cgcgctgtcg   gatcgttcg    ggcggcggcc    9360
aatcttgctc   gtctcgctgg   ccggcgccag   atctggggaa   ccctgtggtt   ggcatgcaca    9420
tacaaatgga   cgaacggata   aaccttttca   cgcccttta    aatatccgat   tattctaata    9480
aacgctcttt   tctcttaggt   ttacccgcca   atatatcctg   tcaaacactg   atagtttaaa    9540
ctgaaggcgg   gaaacgacaa   tctgctagcg   gtcaacatgg   tggagcacga   cactctcgtc    9600
tactccaaga   atatcaaaga   tacagtctca   gaagaccaga   gggctattga   gacttttcaa    9660
caaagggtaa   tatcgggaaa   cctcctcgga   ttccattgcc   cagctatctg   tcacttcatc    9720
gaaaggacag   tagaaaagga   agatggcttc   tacaaatgcc   atcattgcga   taaaggaaag    9780
gctatcgttc   aagatgcctc   taccgacagt   ggtcccaaag   atgaccccc    acccacgagg    9840
aacatcgtgg   aaaagaaga    cgttccaacc   acgtcttcaa   agcaagtgga   ttgatgtgat    9900
ggtcaacatg   gtggagcacg   acactctcgt   ctactccaag   aatatcaaag   atacagtctc    9960
agaagaccag   agggctattg   agacttttca   acaaagggta   atatcgggaa   acctcctcgg   10020
attccattgc   ccagctatct   gtcacttcat   cgaaaggaca   gtagaaaagg   aagatggctt   10080
ctacaaatgc   catcattgcg   ataaaggaaa   ggctatcgtt   caagatgcct   ctaccgacag   10140
tggtcccaaa   gatggacccc   cacccacgag   gaacatcgtg   gaaaagaag    acgttccaac   10200
cacgtcttca   aagcaagtgg   attgatgtga   tatctccact   gacgtaaggg   atgacgcaca   10260
```

```
atcccactat ccttcgcaag acccttcctc tatataagga agttcatttc atttggagag    10320
gataaaacat ttcaatcctt tgaacgcggt agaacgtgct aattggattt tggtgagaac    10380
gcggtagaac gtacttatca cctacagttt tattttgttt ttcttttttgg tttaatctat   10440 ccagcttagt accgagtggg ggaaagtgac tggtgtgcct aaaaccttttt ctttgatact   10500 ttgtaaaaat acatacagat acaatggcga acggtaactt caagttgtct caattgctca    10560
atgtggacga gatgtctgct gagcagagga gtcatttctt tgacttgatg ctgactaaac    10620
ctgattgtga gatcgggcaa atgatgcaaa gagttgttgt tgataaagtc gatgacatga    10680
ttagagaaag aaagactaaa gatccagtga ttgttcatga agttcttttct cagaaggaac   10740 agaacaagtt gatggaaatt tatcctgaat tcaatatcgt gtttaaagac gacaaaaaca    10800
tggttcatgg gtttgcggct gctgagcgaa aactacaagc tttattgctt ttagatagag    10860
ttcctgctct gcaagaggtg gatgacatcg gtggtcaatg gtcgtttttgg gtaactagag   10920 gtgagaaaag gattcattcc tgttgtccaa atctagatat tcgggatgat cagagagaaa    10980
tttctcgaca gatatttctt actgctattg gtgatcaagc tagaagtggt aagagacaga    11040
tgtcggagaa tgagctgtgg atgtatgacc aatttcgtga aaatattgct gcgcctaacg    11100
cggttaggtg caataataca tatcagggtt gtacatgtag gggttttttct gatggtaaga   11160 agaaaggcgc gcagtatgcg atagctcttc acagcctgta tgacttcaag ttgaaagact    11220
tgatggctac tatggttgag aagaaaacta aagtggttca tgctgctatg ctttttgctc    11280
ctgaaagtat gttagtggac gaaggtccat taccttctgt tgacggttac tacatgaaga    11340
agaacgggaa gatctatttc ggttttgaga aagatccttc cttttcttac attcatgact    11400
gggaagagta caagaagtat ctactgggga agccagtgag ttaccaaggg aatgtgttct    11460
acttcgaacc gtggcaggtg agaggagaca caatgctttt ttcgatctac aggatagctg    11520
gagttccgag gaggtctcta tcatcgcaag agtactaccg aagaatatat atcagtagat    11580
gggaaaacat ggttgttgtc ccaattttcg atctggtcga atcaacgcga gagttggtca    11640
agaaagacct gtttgtagag aaacaattca tggacaagtg tttggattac atagctaggt    11700
tatctgacca gcagctgacc ataagcaatg ttaaatcata cttgagttca ataattggg    11760 tcttattcat aaacggggcg gccgtgaaga acaagcaaag tgtagattct cgagatttac    11820
agttgttggc tcaaactttg ctagtgaagg aacaagtggc gagacctgtc atgagggagt    11880
tgcgtgaagc aattctgact gagacgaaac ctatcacgtc attgactgat gtgctgggtt    11940
taatatcaag aaaactgtgg aagcagtttg ctaacaagat cgcagtcggc ggattcgttg    12000
gcatggttgg tactctaatt ggattctatc caaagaaggt actaacctgg gcgaaggaca    12060
caccaaatgg tccagaacta tgttacgaga actcgcacaa aaccaaggtg atagtatttc    12120
tgagtgttgt gtatgccatt ggaggaatca cgcttatgcg tcgagacatc cgagatggac    12180
tggtgaaaaa actatgtgat atgtttgata tcaaacgggg ggcccatgtc ttagacgttg    12240
agaatccgtg ccgctattat gaaatcaacg atttctttag cagtctgtat tcggcatctg    12300
agtccggtga gaccgttttta ccagatttat ccgaggtaaa agccaagtct gataagctat    12360
tgcagcagaa gaaagaaatc gctgacgagt ttctaagtgc aaaattctct aactattctg    12420
gcagttcggt gagaacttct ccaccatcgg tggtcggttc atctcgaagc ggactgggtc    12480
tgttgttgga agacagtaac gtgctgaccc aagctagagt tggagtttca agaaaggtag    12540
acgatgagga gatcatggag cagtttctga gtggtcttat tgacactgaa gcagaaattg    12600
acgaggttgt tccagccttt tcagctgaat gtgaaagagg ggaaacaagc ggtacaaagg    12660
```

```
tgttgtgtaa acctttaacg ccaccaggat ttgagaacgt gttgccagct gtcaaacctt   12720
tggtcagcaa aggaaaaacg gtcaaacgtg tcgattactt ccaagtgatg ggaggtgaga   12780
gattaccaaa aaggccggtt gtcagtggag acgattctgt ggacgctaga agagagtttc   12840
tgtactactt agatgcggag agagtcgctc aaaatgatga aattatgtct ctgtatcgtg   12900
actattcgag aggagttatt cgaactggag gtcagaatta cccgcacgga ctgggagtgt   12960
gggatgtgga gatgaagaac tggtgcatac gtccagtggt cactgaacat gcttatgtgt   13020
tccaaccaga caaacgtatg gatgattggt cgggatactt agaagtggct gtttgggaac   13080
gaggtatgtt ggtcaacgac ttcgcggtcg aaaggatgag tgattatgtc atagtttgcg   13140
atcagacgta tctttgcaat aacaggttga tcttggacaa tttaagtgcc ctggatctag   13200
gaccagttaa ctgttctttt gaattagttg acggtgtacc tggttgtggt aagtcgacaa   13260
tgattgtcaa ctcagctaat ccttgtgtcg atgtggttct ctctactggg agagcagcaa   13320
ccgacgactt gatcgagaga ttcgcgagca aaggttttcc atgcaaattg aaaaggagag   13380
tgaagacggt tgattctttt ttgatgcatt gtgttgatgg ttctttaacc ggagacgtgt   13440
tgcatttcga tgaagctctc atggcccatg ctggtatggt gtactttgc gctcagatag   13500 ctggtgctaa acgatgtatc tgtcaaggag atcagaatca aatttctttc aagcctaggg   13560
tatctcaagt tgatttgagg ttttctagtc tggtcggaaa gtttgacatt gttacagaaa   13620
aaagagaaac ttacagaagt ccagcagatg tggctgccgt attgaacaag tactatactg   13680
gagatgtcag aacacataac gcgactgcta attcgatgac ggtgaggaag attgtgtcta   13740
aagaacaggt ttctttgaag cctggtgctc agtacataac tttccttcag tctgagaaga   13800
aggagttggt aaatttgttg gcattgagga aagtggcagc taaagtgagt acagtacacg   13860
agtcgcaagg agagacattc aaagatgtag tcctagtcag gacgaaacct acggatgact   13920
caatcgctag aggtcgggag tacttaatcg tggcgttgtc gcgtcacaca caatcacttg   13980
tgtatgaaac tgtgaaagag gacgatgtaa gcaaagagat cagggaaagt gccgcgctta   14040
cgaaggcggc tttggcaaga ttttttgtta ctgagaccgt cttatgacgg tttcggtcta   14100
ggtttgatgt ctttagacat catgaagggc cttgcgccgt tccagattca ggtacgatta   14160
cggacttgga gatgtggtac gacgcttttgt ttccgggaaa ttcgttaaga gactcaagcc   14220
tagacgggta tttggtggca acgactgatt gcaatttgcg attagacaat gttacgatca   14280
aaagtggaaa ctggaaagac aagtttgctg aaaagaaac gtttctgaaa ccggttattc   14340
gtactgctat gcctgacaaa aggaagacta ctcagttgga gagtttgtta gcattgcaga   14400
aaaggaacca agcggcaccc gatctacaag aaaatgtgca cgcaacagtt ctaatcgaag   14460
agacgatgaa gaagttgaaa tctgttgtct acgatgtggg aaaaattcgg gctgatccta   14520
ttgtcaatag agctcaaatg gagagatggt ggagaaatca aagcacagcg gtacaggcta   14580
aggtagtagc agatgtgaga gagttacatg aaatagacta ttcgtcttac atgtatatga   14640
tcaaatctga cgtgaaacct aagactgatt taacaccgca atttgaatac tcagctctac   14700
agactgttgt gtatcacgag aagttgatca actcgttgtt cggtccaatt ttcaaagaaa   14760
ttaatgaacg caagttggat gctatgcaac cacattttgt gttcaacacg agaatgacat   14820
cgagtgattt aaacgatcga gtgaagttct aaaatacgga agcggcttac gactttgttg   14880
agatagacat gtctaaattc gacaagtcgg caaatcgctt ccatttacaa ctgcagctgg   14940
agatttacag gttatttggg ctagatgagt gggcggcctt cctttgggag gtgtcgcaca   15000
```

```
ctcaaactac tgtgagagat attcaaaatg gtatgatggc gcatatttgg taccaacaaa    15060
agagtggaga tgctgatact tataatgcaa attcagatag aacactgtgt gcactcttgt    15120
ctgaattacc attggagaaa gcagtcatgg ttacatatgg aggagatgac tcactgattg    15180
cgtttcctag aggaacgcag tttgttgatc cgtgtccaaa gttggctact aagtggaatt    15240
tcgagtgcaa gatttttaag tacgatgtcc caatgttttg tgggaagttc ttgcttaaga    15300
cgtcatcgtg ttacgagttc gtgccagatc cggtaaaagt tctgacgaag ttggggaaaa    15360
agagtataaa ggatgtgcaa catttagccg agatctacat ctcgctgaat gattccaata    15420
gagctcttgg gaactacatg gtggtatcca aactgtccga gtctgtttca gaccggtatt    15480
tgtacaaagg tgattctgtt catgcgcttt gtgcgctatg aagcatatt aagagtttta    15540 cagctctgtg tacattattc cgagacgaaa acgataagga attgaacccg gctaaggttg    15600
attggaagaa ggcacagaga gctgtgtcaa acttttacga ctggtaatat ggaagacaag    15660
tcattggtca ccttgaagaa gaagactttc gaagtctcaa aattctcaaa tctagggcc     15720 attgaattgt tgtggacgg taggaggaag agaccgaagt attttcacag aagaagaaa     15780 actgtcctaa atcatgttgg tgggaagaag agtgaacaca gttagacgt ttttgaccaa     15840 agggattaca aaatgattaa atcttacgcg tttctaaaga tagtaggtgt acaactagtt     15900
gtaacatcac atctacctgc agatacgcct gggttcattc aaatcgatct gttggattcg    15960
agacttactg agaaaagaaa gagaggaaag actattcaga gattcaaagc tcgagcttgc    16020
gataactgtt cagttgcgca gtacaaggtt gaatacagta tttccacaca ggagaacgta    16080
cttgatgtct ggaaggtggg ttgtatttct gagggcgttc cggtctgtga cggtacatac    16140
cctttcagta tcgaagtgtc gctaatatgg gttgctactg attcgactag gcgcctcaat    16200
gtggaagaac tgaacagttc ggattacatt gaaggcgatt ttaccgatca agaggttttc    16260
ggtgagttca tgtctttgaa acaagtggag atgaagacga ttgaggcgaa gtacgatggt    16320
ccttacagac cagctactac tagacctaag tcattattgt caagtgaaga tgttaagaga    16380
gcgtctaata agaaaaactc gtcttaatgc ataaagaaat ttattgtcaa tatgacgtgt    16440
gtactcaagg gttgtgtgaa tgaagtcact gttcttggtc acgagacgtg tagtatcggt    16500
catgctaaca aattgcgaaa gcaagttgct gacatggttg gtgtcacacg taggtgtgcg    16560
gaaaataatt gtggatggtt tgtctgtgtt gttatcaatg attttacttt tgatgtgtat    16620
aattgttgtg gccgtagtca ccttgaaaag tgtcgtaaac gtgttgaaac aagaaatcga    16680
gaaatttgga aacaaattcg acgaaatcaa gctgaaaaca tgtctgcgac agctaaaaag    16740
tctcataatt cgaagacctc taagaagaaa ttcaaagagg acagagaatt tgggacacca    16800
aaaagatttt taagagatga tgttcctttc gggattgatc gtttgtttgc ttttgattt     16860 tatttatat tgttatctgt ttctgtgtat agactgtttg agattggcgc ttggccgact     16920
cattgtctta ccatagggga acggactttg tttgtgttgt tattttattt gtattttatt    16980
aaaattctca atgatctgaa aaggcctcga ggctaagaga ttattggggg gtgagtaagt    17040
acttttaaag tgatgatggt tacaaaggca aaagggtaa aaccccctcgc ctacgtaagc    17100 gttattacgc ccgtctgtac ttatatcagt acactgacga gtccctaaag gacgaaacgg    17160
gccc                                                                17164
```

<210> SEQ ID NO 2
<211> LENGTH: 2915
<212> TYPE: DNA
<213> ORGANISM: Artificial

<220> FEATURE:
<223> OTHER INFORMATION: sequence of synthetic sTRV2

<400> SEQUENCE: 2

```
aagcttggtc aacatggtgg agcacgacac tctcgtctac tccaagaata tcaaagatac    60
agtctcagaa gaccagaggg ctattgagac ttttcaacaa agggtaatat cgggaaacct   120
cctcggattc cattgcccag ctatctgtca cttcatcgaa aggacagtag aaaaggaaga   180
tggcttctac aaatgccatc attgcgataa aggaaaggct atcgttcaag atgcctctac   240
cgacagtggt cccaaagatg acccccacc cacgaggaac atcgtggaaa agaagacgt    300
tccaaccacg tcttcaaagc aagtggattg atgtgatggt caacatggtg gagcacgaca   360
ctctcgtcta ctccaagaat atcaaagata cagtctcaga gaccagagg gctattgaga    420
cttttcaaca aagggtaata tcgggaaacc tcctcggatt ccattgccca gctatctgtc   480
acttcatcga aggacagta gaaaaggaag atggcttcta caaatgccat cattgcgata   540
aaggaaaggc tatcgttcaa gatgcctcta ccgacagtgg tcccaaagat ggaccccac    600
ccacgaggaa catcgtggaa aagaagacg ttccaaccac gtcttcaaag caagtggatt    660
gatgtgatat ctccactgac gtaagggatg acgcacaatc ccactatcct tcgcaagacc   720
cttcctctat ataaggaagt tcatttcatt tggagaggat aaaacattgc acctatggtg   780
ttgccctggc tggggtatgt cagtgatcgc agtagaatgt actaattgac aagttggaga   840
atacggtaga acgtccttat ccaacacagc ctttatccct ctccctgacg aggttttgt    900
cagtgtaata tttcttttg aactatccag cttagtaccg tacgggaaag tgactggtgt    960
gcttatcttt gaaatgttac tttgggtttc ggttctttag gttagtaaga aagcacttgt   1020
cttctcatac aaaggaaaac ctgagacgta tcgcttacga aagtagcaat gaaagaaagg   1080
tggtggtttt aatcgctacc gcaaaaacga tggggtcgtt ttaattaact tctcctacgc   1140
aagcgtctaa acgacgttg ggttttgct agtttctta gagaaaacta gctaagtctt    1200
taatgttatc attagagatg gcataaatat aatacttgtg tctgctgata agatcatttt   1260
aatttggacg attagacttg ttgaactaca ggttactgaa tcacttgcgc taatcaacat   1320
gggagatatg tacgatgaat catttgacaa gtcgggcggt cctgctgact tgatggacga   1380
ttcttgggtg gaatcagttt cgtggaaaga tctgttgaag aagttacaca gcataaaatt   1440
tgcactacag tctggtagag atgagatcac tgggttacta gcggcactga atagacagtg   1500
tccttattca ccatatgagc agtttccaga taagaaggtg tatttccttt tagactcacg   1560
ggctaacagt gctcttggtg tgattcagaa cgcttcagcg ttcaagagac gagctgatga   1620
gaagaatgca gtggcgggtg ttacaaatat tcctgcgaat ccaaacacaa cggttacgac   1680
gaaccaaggg agtactacta ctaccaaggc gaacactggc tcgactttgg aagaagactt   1740
gtacacttat tacaaattcg atgatgcctc tacagctttc cacaaatctc taacttcgtt   1800
agagaacatg gagttgaaga gttattaccg aaggaacttt gagaaagtat tcgggattaa   1860
gtttggtgga gcagctgcta gttcatctgc accgcctcca gcgagtggag gtccgatacg   1920
tcctaatccc tagggattta aggacgtgaa ctctgttgag atctctgtga aattcagagg   1980
gtgggtgata ccatattcac tgatgccatt agcgacatct aaatagggct aattgtgact   2040
aatttgaggg aatttccttt accattgacg tcagtgtcgt tggtagcatt tgagtttcgc   2100
aatgcacgaa ttacttagga agtggcttga cgacactaat gtgttattgt tagataatgg   2160
tttggtggtc aaggtacgta gtagagtccc acatattcgc acgtatgaag taattggaaa   2220
```

```
gttgtcagtt tttgataatt cactgggaga tgatacgctg tttgagggaa aagtagagaa      2280
cgtatttgtt tttatgttca ggcggttctt gtgtgtcaac aaagatggac attgttactc      2340
aaggaagcac gatgagcttt attattacgg acgagtggac ttagattctg tgagtaaggt      2400
taccgaattc tctagaaggc ctccatgggg atccggtacc gagctcacgc gtctcgaggc      2460
ccgggcatgt cccgaagaca ttaaactacg gttctttaag tagatccgtg tctgaagttt      2520
taggttcaat ttaaacctac gagattgaca ttctcgactg atcttgattg atcggtaagt      2580
cttttgtaat ttaattttct ttttgatttt attttaaatt gttatctgtt tctgtgtata      2640
gactgtttga gatcggcgtt tggccgactc attgtcttac catagggaaa cggactttgt      2700
ttgtgttgtt attttatttg tattttatta aaattctcaa cgatctgaaa aagcctcgcg      2760
gctaagagat tgttgggggg tgagtaagta ctttttaaagt gatgatggtt acaaaggcaa      2820
aaggggtaaa accccctcgcc tacgtaagcg ttattacgcc cgtctgtact tatatcagta      2880
cactgacgag tccctaaagg acgaaacggg ttaac                                 2915

<210> SEQ ID NO 3
<211> LENGTH: 235
<212> TYPE: DNA
<213> ORGANISM: Pea early browning virus

<400> SEQUENCE: 3
gtgcacacaa ggttaaaaac gctgtagtaa tacatgcgca agaacaggct gagcatcttg        60
ttctggggtt tcacactatc tttagagaaa gtgttaagtt aattaagtta tcttaattaa       120
gagcataatt atactgattt gtctctcgtt gatagagtct atcattctgt tactaaaaat       180
ttgacaactc ggtttgctga cctactggtt actgtatcac ttacccgagt taacg            235

<210> SEQ ID NO 4
<211> LENGTH: 28
<212> TYPE: DNA
<213> ORGANISM: Artificial
<220> FEATURE:
<223> OTHER INFORMATION: PCR Primer

<400> SEQUENCE: 4
cctgaattca atatcgtgtt taaagacg                                            28

<210> SEQ ID NO 5
<211> LENGTH: 34
<212> TYPE: DNA
<213> ORGANISM: Artificial
<220> FEATURE:
<223> OTHER INFORMATION: PCR Primer

<400> SEQUENCE: 5
ataattctag aggggggactg tttctggtgg catg                                    34

<210> SEQ ID NO 6
<211> LENGTH: 42
<212> TYPE: DNA
<213> ORGANISM: Artificial
<220> FEATURE:
<223> OTHER INFORMATION: PCR Primer

<400> SEQUENCE: 6
cgttttgggt aactagaggt aagtacattt ccataacgtt cc                            42

<210> SEQ ID NO 7
<211> LENGTH: 42
```

<212> TYPE: DNA
<213> ORGANISM: Artificial
<220> FEATURE:
<223> OTHER INFORMATION: PCR Primer

<400> SEQUENCE: 7
aatgaatcct tttctcacct gtcaaaattg atataaaaaa ta                              42

<210> SEQ ID NO 8
<211> LENGTH: 43
<212> TYPE: DNA
<213> ORGANISM: Artificial
<220> FEATURE:
<223> OTHER INFORMATION: PCR Primer

<400> SEQUENCE: 8
ttatatcaat tttgacaggt gagaaaagga ttcattcctg ttg                             43

<210> SEQ ID NO 9
<211> LENGTH: 27
<212> TYPE: DNA
<213> ORGANISM: Artificial
<220> FEATURE:
<223> OTHER INFORMATION: PCR Primer

<400> SEQUENCE: 9
cctacatgta caaccctgat atgtatt                                               27

<210> SEQ ID NO 10
<211> LENGTH: 30
<212> TYPE: DNA
<213> ORGANISM: Artificial
<220> FEATURE:
<223> OTHER INFORMATION: PCR Primer

<400> SEQUENCE: 10
attatctaga aattgaaaga agaagtgagg                                            30

<210> SEQ ID NO 11
<211> LENGTH: 30
<212> TYPE: DNA
<213> ORGANISM: Artificial
<220> FEATURE:
<223> OTHER INFORMATION: PCR Primer

<400> SEQUENCE: 11
tattggatcc caggaagttc atctatgcat                                            30

<210> SEQ ID NO 12
<211> LENGTH: 34
<212> TYPE: DNA
<213> ORGANISM: Artificial
<220> FEATURE:
<223> OTHER INFORMATION: PCR Primer

<400> SEQUENCE: 12
ataattctag aggggggactg tttctggtgg catg                                      34

<210> SEQ ID NO 13
<211> LENGTH: 25
<212> TYPE: DNA
<213> ORGANISM: Artificial
<220> FEATURE:
<223> OTHER INFORMATION: PCR Primer

<400> SEQUENCE: 13

```
ccgtaaggga tcccttcttg atacc                                          25
```

<210> SEQ ID NO 14
<211> LENGTH: 34
<212> TYPE: DNA
<213> ORGANISM: Artificial
<220> FEATURE:
<223> OTHER INFORMATION: PCR Primer

<400> SEQUENCE: 14

```
ataattctag aggggactg tttctggtgg catg                                 34
```

<210> SEQ ID NO 15
<211> LENGTH: 25
<212> TYPE: DNA
<213> ORGANISM: Artificial
<220> FEATURE:
<223> OTHER INFORMATION: PCR Primer

<400> SEQUENCE: 15

```
ccgtaaggga tcccttcttg atacc                                          25
```

<210> SEQ ID NO 16
<211> LENGTH: 604
<212> TYPE: DNA
<213> ORGANISM: Gossypium sp.

<400> SEQUENCE: 16

```
atgccgagaa cgacctctac accacatccc ttcgattccg attactccga gagcatggat    60
tcaatgtttc atcgacgta ttcaacaagt ttaaagacga gcaagggaat ttcaagtcat    120
ccgtgacaag cgatgttcga ggattgttgg aactttacca agcttcctat ttgagggttc   180
atggggaaga tatattggat gaagcaattt ctttcaccac caaccattta agccttgcag   240
tagcatcttt ggactatccg ttatccgaag aggtttcaca tgctttgaaa caatcaattc   300
gaagaggctt gccaagggtt gaggcaagac actatctttc agtataccaa gatattgagt   360
cccataataa ggttttgttg gagtttgcta agatcgattt caacatggta caacttttgc   420
ataggaaaga gctaagtgag atttctaggt ggtggaagga tttagacttt caaagaaagt   480
tgccatacgc aagagataga gtggttgaag gctattttg gatctcagga gtgtactttg    540
agccccaata ttctcttggt agaaagatgt tgacaaaagt gatagcaatg gcttctattg   600
taga                                                                604
```

<210> SEQ ID NO 17
<211> LENGTH: 1489
<212> TYPE: DNA
<213> ORGANISM: Gossypium herbaceum

<400> SEQUENCE: 17

```
aatcggcacg aggcttgaga gagtttgtgt gttttggttg tttggactgt cggctttgat   60
tttatggcct ccttaatcct ttgctgttct tgtcggagat tgtaagcttg aagatgcaac   120
caacacaaag tttaaatttg ggcacttgaa ctcaaagaaa atatgttgtt atcagttggc   180
tataagcaaa gcgatggcta aacttactga tcatctatca gatacattat gaggatcaca   240
gagcaatggg aagtggtgtt ttcccctgga aatgaaggag agacagcggt ggagagctga   300
agaagacgct tgttgtgtgt catacgtaaa acaatatggt ccgagggagt ggaaccttgt    360
gtcacaccgc atgaacacac ccctgaacag ggatgcaaaa tcttgcttag aaaggtggaa   420
taactatctc aaacctggta tcaagaaggg atcccttacg gaagaagagc aacgtcttgt   480
```

```
aatccgtctt caagctaaac acggcaacaa atggaagaaa attgcagctg aagtccctgg      540
tagaacagct aaaagactgg gcaagtggtg ggaggtattc aaggagaagc aacaaaggga      600
acataaagag aagcataaga cggttgagcc agtcgaggaa ggaaagtacg ataggatatt      660
agaaactttt gccgaaaaaa tagtaaaaca gggccatagc tcagcctttc ccatggctgc      720
ttctaacggg ggttttcttc atactgaccc accttcacct gcaccaccaa ctttacttcc      780
accttggctt tctaattcca gcaatgcgtc cgttgtcaca ccaccttccc cttctgtgac      840
tttaagctta tctccctcaa cggtggcagc tgctccccca atcccgtggc tgcaacctga      900
gaggatgtcc gaaactagcc ctgttttggg aaacagggtg ccccatggat catttcctcg      960
tagtgagaac ctgctgatat ctgaattgat ggactgctgc agacagctgg aagatgggcg     1020
ccgcgcttgg gttgcacata gaaggaagc ggcctggagg ttaagaaggg tagagttaca      1080
actcgaatca gaaaaggctt cccgtaaaag gaagaagatg aagaaatag agtcaaagat       1140 cgaggctcta aggaagagc agaagagtac acttgataga atcgaagctg aatataggga       1200
acaactggag gggctaagaa gagatgcgga agcgaaggag caaaaattag cggagcaatg     1260
ggctgcaaag catttgcatc tgaccaagtt tcttgaacaa acggggtgca gacccagggt     1320
tgtggagcct aatgggcagt gagcaaagat gatttatcaa gcgtctcctt tcaacagact     1380
ctgcattgtt tttgatgata ttctctacta tagaagtcta tttatagttg gttttctag       1440 gatgggacac tctgaatggg aaaggtagca ttagccctat ctttgtgtt               1489
```

<210> SEQ ID NO 18
<211> LENGTH: 353
<212> TYPE: PRT
<213> ORGANISM: Gossypium herbaceum

<400> SEQUENCE: 18

```
Met Lys Glu Arg Gln Arg Trp Arg Ala Glu Glu Asp Ala Leu Leu Cys
1               5                   10                  15

Ala Tyr Val Lys Gln Tyr Gly Pro Arg Glu Trp Asn Leu Val Ser His
            20                  25                  30

Arg Met Asn Thr Pro Leu Asn Arg Asp Ala Lys Ser Cys Leu Glu Arg
        35                  40                  45

Trp Asn Asn Tyr Leu Lys Pro Gly Ile Lys Lys Gly Ser Leu Thr Glu
    50                  55                  60

Glu Glu Gln Arg Leu Val Ile Arg Leu Gln Ala Lys His Gly Asn Lys
65                  70                  75                  80

Trp Lys Lys Ile Ala Ala Glu Val Pro Gly Arg Thr Ala Lys Arg Leu
                85                  90                  95

Gly Lys Trp Trp Glu Val Phe Lys Glu Lys Gln Gln Arg Glu His Lys
            100                 105                 110

Glu Lys His Lys Thr Val Glu Pro Val Glu Glu Gly Lys Tyr Asp Arg
        115                 120                 125

Ile Leu Glu Thr Phe Ala Glu Lys Ile Val Lys Gln Gly His Ser Ser
    130                 135                 140

Ala Phe Pro Met Ala Ala Ser Asn Gly Gly Phe Leu His Thr Asp Pro
145                 150                 155                 160

Pro Ser Pro Ala Pro Pro Thr Leu Leu Pro Pro Trp Leu Ser Asn Ser
                165                 170                 175

Ser Asn Ala Ser Val Val Thr Pro Pro Ser Pro Ser Val Thr Leu Ser
            180                 185                 190
```

Leu Ser Pro Ser Thr Val Ala Ala Pro Pro Ile Pro Trp Leu Gln
            195                 200                 205

Pro Glu Arg Met Ser Glu Thr Ser Pro Val Leu Gly Asn Arg Val Pro
210                 215                 220

His Gly Ser Phe Pro Arg Ser Glu Asn Leu Leu Ile Ser Glu Leu Met
225                 230                 235                 240

Asp Cys Cys Arg Gln Leu Glu Asp Gly Arg Arg Ala Trp Val Ala His
                245                 250                 255

Arg Lys Glu Ala Ala Trp Arg Leu Arg Val Glu Leu Gln Leu Glu
            260                 265                 270

Ser Glu Lys Ala Ser Arg Lys Lys Met Glu Glu Ile Glu Ser
            275                 280                 285

Lys Ile Glu Ala Leu Arg Glu Glu Gln Lys Ser Thr Leu Asp Arg Ile
290                 295                 300

Glu Ala Glu Tyr Arg Glu Gln Leu Glu Gly Leu Arg Arg Asp Ala Glu
305                 310                 315                 320

Ala Lys Glu Gln Lys Leu Ala Gly Gln Trp Ala Ala Lys His Leu His
                325                 330                 335

Leu Thr Lys Phe Leu Glu Gln Thr Gly Cys Arg Pro Arg Val Val Glu
            340                 345                 350

Pro

<210> SEQ ID NO 19
<211> LENGTH: 367
<212> TYPE: PRT
<213> ORGANISM: Arabidopsis thaliana

<400> SEQUENCE: 19

Met Lys Glu Arg Gln Arg Trp Ser Gly Glu Glu Asp Ala Leu Leu Arg
1               5                   10                  15

Ala Tyr Val Arg Gln Phe Gly Pro Arg Glu Trp His Leu Val Ser Glu
            20                  25                  30

Arg Met Asn Lys Pro Leu Asn Arg Asp Ala Lys Ser Cys Leu Glu Arg
        35                  40                  45

Trp Lys Asn Tyr Leu Lys Pro Gly Ile Lys Lys Gly Ser Leu Thr Glu
    50                  55                  60

Glu Glu Gln Arg Leu Val Ile Arg Leu Gln Glu Lys His Gly Asn Lys
65                  70                  75                  80

Trp Lys Lys Ile Ala Ala Glu Val Pro Gly Arg Thr Ala Lys Arg Leu
                85                  90                  95

Gly Lys Trp Trp Glu Val Phe Lys Glu Lys Gln Arg Glu Glu Lys
            100                 105                 110

Glu Ser Asn Lys Arg Val Glu Pro Ile Asp Glu Ser Lys Tyr Asp Arg
        115                 120                 125

Ile Leu Glu Ser Phe Ala Glu Lys Leu Val Lys Glu Arg Ser Asn Val
130                 135                 140

Val Pro Ala Ala Ala Ala Ala Thr Val Val Met Ala Asn Ser Asn
145                 150                 155                 160

Gly Gly Phe Leu His Ser Glu Gln Gln Val Gln Pro Pro Asn Pro Val
                165                 170                 175

Ile Pro Pro Trp Leu Ala Thr Ser Asn Asn Gly Asn Asn Val Val Ala
            180                 185                 190

Arg Pro Pro Ser Val Thr Leu Thr Leu Ser Pro Ser Val Ala Ala
        195                 200                 205

```
Ala Ala Pro Gln Pro Pro Ile Pro Trp Leu Gln Gln Gln Pro Glu
210                 215                 220

Arg Ala Glu Asn Gly Pro Gly Gly Leu Val Leu Gly Ser Met Met Pro
225                 230                 235                 240

Ser Cys Ser Gly Ser Ser Glu Ser Val Phe Leu Ser Glu Leu Val Glu
            245                 250                 255

Cys Cys Arg Glu Leu Glu Glu Gly His Arg Ala Trp Ala Asp His Lys
            260                 265                 270

Lys Glu Ala Ala Trp Arg Leu Arg Arg Leu Glu Leu Gln Leu Glu Ser
                275                 280                 285

Glu Lys Thr Cys Arg Gln Arg Glu Lys Met Glu Ile Glu Ala Lys
290                 295                 300

Met Lys Ala Leu Arg Glu Glu Gln Lys Asn Ala Met Glu Lys Ile Glu
305                 310                 315                 320

Gly Glu Tyr Arg Glu Gln Leu Val Gly Leu Arg Arg Asp Ala Glu Ala
                325                 330                 335

Lys Asp Gln Lys Leu Ala Asp Gln Trp Thr Ser Arg His Ile Arg Leu
                340                 345                 350

Thr Lys Phe Leu Glu Gln Gln Met Gly Cys Arg Leu Asp Arg Pro
            355                 360                 365

<210> SEQ ID NO 20
<211> LENGTH: 363
<212> TYPE: PRT
<213> ORGANISM: Nicotiana tabacum

<400> SEQUENCE: 20

Met Arg Glu Arg Gln Arg Trp Arg Ser Glu Glu Asp Ala Leu Leu Arg
1               5                   10                  15

Ala Tyr Val Lys Gln Tyr Gly Pro Lys Glu Trp His Leu Val Ser Gln
                20                  25                  30

Arg Met Asn Thr Ala Leu Asn Arg Asp Ala Lys Ser Cys Leu Glu Arg
            35                  40                  45

Trp Lys Asn Tyr Leu Lys Pro Gly Ile Lys Lys Gly Ser Leu Thr Gln
50                  55                  60

Glu Glu Gln Arg Leu Val Ile His Leu Gln Ala Lys His Gly Asn Lys
65                  70                  75                  80

Trp Lys Lys Ile Ala Ala Glu Val Pro Gly Arg Thr Ala Lys Arg Leu
                85                  90                  95

Gly Lys Trp Trp Glu Val Phe Lys Glu Lys Gln His Arg Glu Gln Lys
            100                 105                 110

Glu Asn Asn Lys Val Val Asp Pro Val Asp Glu Gly Lys Tyr Asp His
        115                 120                 125

Ile Leu Glu Thr Phe Ala Glu Lys Ile Val Lys Glu Arg Ser Val Pro
    130                 135                 140

Gly Leu Leu Met Ala Thr Ser Asn Gly Gly Phe Leu His Ala Asp Ala
145                 150                 155                 160

Pro Ala Pro Ser Pro Gln Thr Leu Leu Pro Pro Trp Leu Ser Asn Ser
                165                 170                 175

Thr Ala Thr Ser Thr Val Arg Ser Pro Ser Pro Ser Val Thr Leu Ser
            180                 185                 190

Leu Ser Pro Ser Thr Val Pro Pro Thr Pro Thr Pro Thr Pro Gly Ile
        195                 200                 205

Pro Trp Leu Gln Thr Asp Arg Gly Pro Glu Asn Ala Pro Leu Ile Leu
    210                 215                 220
```

```
Ser Ser Phe Pro His His Gly Val Ala Pro Pro Cys Gly Glu Asn Pro
225                 230                 235                 240

Phe Val Thr Glu Leu Val Glu Cys Cys Lys Glu Leu Asp Glu Gly His
            245                 250                 255

Arg Ala Trp Ala Ala His Lys Lys Glu Ala Ala Trp Arg Leu Arg Arg
        260                 265                 270

Val Glu Leu Gln Leu Glu Ser Glu Lys Ile Cys Lys Val Arg Glu Lys
    275                 280                 285

Met Glu Glu Ile Glu Ala Lys Met Lys Ala Leu Arg Glu Glu Gln Lys
290                 295                 300

Ala Thr Leu Asp Arg Ile Glu Ala Glu Tyr Lys Glu Gln Leu Ala Gly
305                 310                 315                 320

Leu Arg Arg Asp Ala Glu Ala Lys Glu Gln Lys Leu Ala Glu Gln Trp
            325                 330                 335

Ala Ser Lys His Leu Arg Leu Ser Lys Phe Leu Glu Gln Met Gly Cys
        340                 345                 350

Gln Ser Arg Leu Ala Glu Pro Asn Gly Gly Arg
    355                 360

<210> SEQ ID NO 21
<211> LENGTH: 404
<212> TYPE: PRT
<213> ORGANISM: Selaginella kraussiana

<400> SEQUENCE: 21

Met Lys Asp Lys Gln Arg Trp Gln Pro Glu Glu Asp Ala Leu Leu Cys
1               5                   10                  15

Ala Tyr Val Lys Gln Tyr Gly Pro Asn Asp Trp Asn Leu Val Ser Glu
            20                  25                  30

Arg Met Ala Thr Pro Leu Asp Arg Asp Pro Lys Ser Cys His Glu Arg
        35                  40                  45

Trp Lys Asn Tyr Leu Lys Pro Gly Leu Lys Arg Gly Pro Leu Ser Glu
    50                  55                  60

Glu Gln Asn Leu Val Ile Arg Leu Gln Glu Lys Tyr Gly Asn Lys
65                  70                  75                  80

Trp Lys Arg Ile Ala Ala Glu Val Pro Gly Arg Thr Ala Lys Arg Leu
                85                  90                  95

Gly Lys Trp Trp Glu Val His Lys Glu Arg Arg Gln Lys Glu Ala Ile
            100                 105                 110

Gln Arg His Gln Arg Ile Gln Thr Gly Val His Thr Ser His Leu Ser
        115                 120                 125

Met Phe Tyr Gly Gln Thr Val Ala Pro Phe Ile Pro Pro Ala Gln Ser
    130                 135                 140

Phe Ser Thr Cys Ala Glu Val Val Ser Ser Ser Ala Ser Glu Gly
145                 150                 155                 160

Glu Ser Gln Cys Arg Asn Glu Pro Arg Met Asn Leu Pro Ala Ala Phe
                165                 170                 175

Pro Pro Thr Ser Ser Glu Pro Val Leu Thr Leu Gly Pro Thr Val Leu
            180                 185                 190

Asp Leu Leu Pro Ala Trp Lys Pro Ala Pro Arg Ala Ala Ser Thr Ser
        195                 200                 205

Glu Leu Pro Ser Leu Met Ala Pro Glu Ala Ile Met Lys Pro Asn Leu
    210                 215                 220

Ser Leu Ser Leu Asp Ser Gly Ala Glu Ser Gly Asp Thr Asp Thr Gly
```

```
                225                 230                 235                 240

Thr His Phe Asn Asn Lys Lys Val Ser Thr Ile Ile Pro Lys Asp
                        245                 250                 255

Asp Glu Phe Cys Asn Glu Ile Asn Ser Asp Ile Ser Pro Gly Glu Leu
                            260                 265                 270

Ile Pro Leu Leu Gly Leu Val Lys Glu Leu Glu Asn Lys Glu Ser
                        275                 280                 285

Trp Asn Val Gln Lys Lys Asn Ala Ala Ser Thr Leu Arg Glu Leu Lys
                            290                 295                 300

Gln Gln Leu Glu Cys Glu Arg Ile Glu Lys Lys Gln Lys Met Leu
        305                 310                 315                 320

Glu Val Glu Ser Lys Ile Gln Ala Leu Arg Lys Glu Lys Leu Tyr
                            325                 330                 335

Leu Asp Lys Leu Glu Leu Asp Tyr Ala Glu Leu Val Ala Lys Leu Asp
                        340                 345                 350

Arg Asp Ala Glu Leu Lys Glu Glu Lys Leu Val Glu Ser Trp Ser Leu
                            355                 360                 365

Lys Tyr Asn Lys Leu Val Leu Met Phe Glu Gln Thr Met Gln Arg Tyr
                        370                 375                 380

Ser Ser Phe His Gly Pro Ile Phe Gln Ala Ile Gln Met Arg Gly Met
        385                 390                 395                 400

Asn Ser Pro Ala

<210> SEQ ID NO 22
<211> LENGTH: 349
<212> TYPE: PRT
<213> ORGANISM: Artificial
<220> FEATURE:
<223> OTHER INFORMATION: Consensus sequence of SINs 18-21

<400> SEQUENCE: 22

Met Lys Glu Arg Gln Arg Trp Arg Ala Glu Glu Asp Ala Leu Leu Arg
        1               5                   10                  15

Ala Tyr Val Lys Gln Tyr Gly Pro Arg Glu Trp Asn Leu Val Ser Glu
                        20                  25                  30

Arg Met Asn Thr Pro Leu Asn Arg Asp Ala Lys Ser Cys Leu Glu Arg
                            35                  40                  45

Trp Lys Asn Tyr Leu Lys Pro Gly Ile Lys Lys Gly Ser Leu Thr Glu
                        50                  55                  60

Glu Glu Gln Arg Leu Val Ile Arg Leu Gln Glu Lys His Gly Asn Lys
        65                  70                  75                  80

Trp Lys Lys Ile Ala Ala Glu Val Pro Gly Arg Thr Ala Lys Arg Leu
                            85                  90                  95

Gly Lys Trp Trp Glu Val Phe Lys Glu Lys Gln Arg Glu Gln Lys
                        100                 105                 110

Glu Ala Asn Lys Arg Val Glu Pro Ile Asp Glu Gly Lys Tyr Asp Arg
                            115                 120                 125

Ile Leu Glu Thr Phe Ala Glu Lys Ile Val Lys Glu Arg Ser Ala Ala
                        130                 135                 140

Ala Ala Ala Val Val Met Ala Ser Ser Asn Gly Gly Phe Leu His Ser
        145                 150                 155                 160

Asp Pro Ala Pro Ala Pro Pro Thr Leu Leu Pro Trp Leu Ser Asn
                            165                 170                 175

Ser Thr Asn Ala Ser Leu Val Ala Pro Ser Pro Ser Val Thr Leu Ser
                        180                 185                 190
```

```
Leu Ser Pro Ser Thr Val Ala Ala Pro Pro Ile Pro Trp Leu
        195                 200                 205

Gln Asp Arg Ala Glu Asn Gly Pro Val Ile Gly Ser Met Pro His Cys
210                 215                 220

Ala Pro Ser Glu Asn Leu Phe Leu Ser Glu Leu Val Glu Cys Cys Lys
225                 230                 235                 240

Glu Leu Glu Glu Gly His Arg Ala Trp Ala His Lys Lys Glu Ala
                245                 250                 255

Ala Trp Arg Leu Arg Arg Leu Glu Leu Gln Leu Glu Ser Glu Lys Ile
                260                 265                 270

Cys Lys Lys Arg Glu Lys Met Glu Glu Ile Glu Ala Lys Ile Lys Ala
                275                 280                 285

Leu Arg Glu Glu Gln Lys Ala Thr Leu Asp Lys Ile Glu Ala Glu Tyr
            290                 295                 300

Arg Glu Gln Leu Ala Gly Leu Arg Arg Asp Ala Glu Ala Lys Glu Gln
305                 310                 315                 320

Lys Leu Ala Glu Gln Trp Ala Ser Lys His Leu Arg Leu Thr Lys Phe
                    325                 330                 335

Leu Glu Gln Thr Gly Cys Arg Arg Leu Glu Pro Asn Gly
                340                 345

<210> SEQ ID NO 23
<211> LENGTH: 2329
<212> TYPE: DNA
<213> ORGANISM: Gossypium herbaceum
<220> FEATURE:
<221> NAME/KEY: CDS
<222> LOCATION: (1)..(2328)

<400> SEQUENCE: 23 aga gaa tca tat ctt gga aag cac ctt cct gct tat gat ggt cga aag     48
Arg Glu Ser Tyr Leu Gly Lys His Leu Pro Ala Tyr Asp Gly Arg Lys
1               5                  10                  15 agc ctt tac acc gct ggg cct ctc cct ttt gtg tca aag gag ttt agg     96
Ser Leu Tyr Thr Ala Gly Pro Leu Pro Phe Val Ser Lys Glu Phe Arg
            20                  25                  30 atc acc ctt att gat gat gat gat ggg tcg gga atg caa aga aga gag    144
Ile Thr Leu Ile Asp Asp Asp Asp Gly Ser Gly Met Gln Arg Arg Glu
        35                  40                  45 tgc gaa ttt aga gtt gtg atc aaa ctg gct gca cgt gct gat ctg cat    192
Cys Glu Phe Arg Val Val Ile Lys Leu Ala Ala Arg Ala Asp Leu His
    50                  55                  60 cat ctt gga ctc ttt ctg caa ggg aag caa gct gat gca cct cag gaa    240
His Leu Gly Leu Phe Leu Gln Gly Lys Gln Ala Asp Ala Pro Gln Glu
65                  70                  75                  80 gct ctc cag gtt ctt gac att gtt ctt cgt gaa tta cct act acc agg    288
Ala Leu Gln Val Leu Asp Ile Val Leu Arg Glu Leu Pro Thr Thr Arg
                85                  90                  95 tac tgt cct gtt ggc cgt tca ttc tac tca cct gac cta ggg aga aag    336
Tyr Cys Pro Val Gly Arg Ser Phe Tyr Ser Pro Asp Leu Gly Arg Lys
            100                 105                 110 caa ccg ttg ggt gag gga ata gaa agc tgg cgt ggc ttc tac caa agc    384
Gln Pro Leu Gly Glu Gly Ile Glu Ser Trp Arg Gly Phe Tyr Gln Ser
        115                 120                 125 att cgt ccc aca cag atg gga cta tca ctg aat att gat atg tct tct    432
Ile Arg Pro Thr Gln Met Gly Leu Ser Leu Asn Ile Asp Met Ser Ser
    130                 135                 140 act gct ttc att gag cca ttg cca gtt att gat ttt gta aca caa ttg    480
```

```
Thr Ala Phe Ile Glu Pro Leu Pro Val Ile Asp Phe Val Thr Gln Leu
145                 150                 155                 160 cta aac cgg gat gtt tct tct aga cca cta tct gat gct gat cgt gtg    528
Leu Asn Arg Asp Val Ser Ser Arg Pro Leu Ser Asp Ala Asp Arg Val
                    165                 170                 175 aag att aaa aag gct ctt aga gga gtc aaa gta gaa gtt aca cac cgt    576
Lys Ile Lys Lys Ala Leu Arg Gly Val Lys Val Glu Val Thr His Arg
            180                 185                 190 ggc aac atg cga aga aaa tat cga ata tca ggt tta aca tca caa gca    624
Gly Asn Met Arg Arg Lys Tyr Arg Ile Ser Gly Leu Thr Ser Gln Ala
                195                 200                 205 act aga gag ttg act ttt cct gta gat gat aga ggt aca atg aaa tct    672
Thr Arg Glu Leu Thr Phe Pro Val Asp Asp Arg Gly Thr Met Lys Ser
210                 215                 220 gtt gtg gag tat ttt cat gaa act tat ggt ttc atc att caa cat acc    720
Val Val Glu Tyr Phe His Glu Thr Tyr Gly Phe Ile Ile Gln His Thr
225                 230                 235                 240 caa tgg cct tgt cta caa gtt gga aac cag cag aga cca aat tat ttg    768
Gln Trp Pro Cys Leu Gln Val Gly Asn Gln Gln Arg Pro Asn Tyr Leu
                    245                 250                 255 cca atg gag gta tgc aag att gtt gag ggt cag agg tac tca aag aga    816
Pro Met Glu Val Cys Lys Ile Val Glu Gly Gln Arg Tyr Ser Lys Arg
                260                 265                 270 ttg aat gag aaa caa att act gct tta ctg aag gtc acc tgc cag cgt    864
Leu Asn Glu Lys Gln Ile Thr Ala Leu Leu Lys Val Thr Cys Gln Arg
            275                 280                 285 cct cag gaa aga gag tat gat att atg aag acg gta caa cat aat gct    912
Pro Gln Glu Arg Glu Tyr Asp Ile Met Lys Thr Val Gln His Asn Ala
        290                 295                 300 tat cat gaa gac ccg tat gct aag gaa ttt gga att aaa att agt gag    960
Tyr His Glu Asp Pro Tyr Ala Lys Glu Phe Gly Ile Lys Ile Ser Glu
305                 310                 315                 320 aag ctt gct tca gtt gaa gcg cgt att ctg cct cca ccg tgg ctt aaa   1008
Lys Leu Ala Ser Val Glu Ala Arg Ile Leu Pro Pro Pro Trp Leu Lys
                    325                 330                 335 tat cat gat act ggt aaa gag aag gat tgc ctg cct cag gtt ggg caa   1056
Tyr His Asp Thr Gly Lys Glu Lys Asp Cys Leu Pro Gln Val Gly Gln
                340                 345                 350 tgg aat atg atg aac aag aaa atg gtt aat ggt ggg act gta aac aac   1104
Trp Asn Met Met Asn Lys Lys Met Val Asn Gly Gly Thr Val Asn Asn
            355                 360                 365 tgg atc tgc ata aac ttt tct cgg caa gtc caa gat agt gtg gca cgg   1152
Trp Ile Cys Ile Asn Phe Ser Arg Gln Val Gln Asp Ser Val Ala Arg
370                 375                 380 agg ttt tgt tat gag ctt gca caa atg tgt tac atc tct ggc atg gcc   1200
Arg Phe Cys Tyr Glu Leu Ala Gln Met Cys Tyr Ile Ser Gly Met Ala
385                 390                 395                 400 ttt aat cct gaa cca gtg ctt cct cca att agt gct cgt cct gag tat   1248
Phe Asn Pro Glu Pro Val Leu Pro Pro Ile Ser Ala Arg Pro Glu Tyr
                    405                 410                 415 gtt gag aag gtt ttg aaa aca cga tat cat gat gcc atg att aaa ctg   1296
Val Glu Lys Val Leu Lys Thr Arg Tyr His Asp Ala Met Ile Lys Leu
                420                 425                 430 cag ccc cag aac aaa gaa att gac ctg ctt att gtt att ctt cca gat   1344
Gln Pro Gln Asn Lys Glu Ile Asp Leu Leu Ile Val Ile Leu Pro Asp
            435                 440                 445 aat aat ggc tct ctt tat ggt gat ttg aaa agg att tgt gag act gat   1392
Asn Asn Gly Ser Leu Tyr Gly Asp Leu Lys Arg Ile Cys Glu Thr Asp
        450                 455                 460
```

| | |
|---|---|
| ctt ggt att gtt tcc cag tgc tgc ttg act aaa cat gta ttt aga atg<br>Leu Gly Ile Val Ser Gln Cys Cys Leu Thr Lys His Val Phe Arg Met<br>465                    470                    475                  480 | 1440 |
| agc aaa caa tat ttg gcc aat gtg gca ttg aaa att aat gtc aag gtt<br>Ser Lys Gln Tyr Leu Ala Asn Val Ala Leu Lys Ile Asn Val Lys Val<br>                    485                    490                    495 | 1488 |
| ggg gga aga aat act gtt ctt gtt gat gca ata tca cga agg ata cct<br>Gly Gly Arg Asn Thr Val Leu Val Asp Ala Ile Ser Arg Arg Ile Pro<br>500                    505                    510 | 1536 |
| ctt gtc agt gac cgt ccg act ata att ttt ggt gct gat gtt acc cat<br>Leu Val Ser Asp Arg Pro Thr Ile Ile Phe Gly Ala Asp Val Thr His<br>              515                    520                    525 | 1584 |
| cct cac cct ggg gag gat tca agc cct tct att gca gct gtt gtt gcc<br>Pro His Pro Gly Glu Asp Ser Ser Pro Ser Ile Ala Ala Val Val Ala<br>530                    535                    540 | 1632 |
| tct caa gat tgg cca gag gtt aca aag tat gct ggc ctg gtt tgt gct<br>Ser Gln Asp Trp Pro Glu Val Thr Lys Tyr Ala Gly Leu Val Cys Ala<br>545                    550                    555                  560 | 1680 |
| caa gct cat cga cag gag ctc atc caa gat tta ttc aag aca tgg cag<br>Gln Ala His Arg Gln Glu Leu Ile Gln Asp Leu Phe Lys Thr Trp Gln<br>                    565                    570                    575 | 1728 |
| gat cct gca agg ggg act gtt tct ggt ggc atg att aag gag ctc cta<br>Asp Pro Ala Arg Gly Thr Val Ser Gly Gly Met Ile Lys Glu Leu Leu<br>580                    585                    590 | 1776 |
| ata tct ttc cga cga gcc act gga cag aag cca cag cgc att ata ttc<br>Ile Ser Phe Arg Arg Ala Thr Gly Gln Lys Pro Gln Arg Ile Ile Phe<br>              595                    600                    605 | 1824 |
| tac aga gat ggt gtc agc gaa ggc cag ttc tat caa gtt ctg tta tat<br>Tyr Arg Asp Gly Val Ser Glu Gly Gln Phe Tyr Gln Val Leu Leu Tyr<br>610                    615                    620 | 1872 |
| gaa ctt gat gct att cgt aag gca tgt gcc tca ttg gag cca aat tat<br>Glu Leu Asp Ala Ile Arg Lys Ala Cys Ala Ser Leu Glu Pro Asn Tyr<br>625                    630                    635                  640 | 1920 |
| cag cct cct gtt aca ttt gtt gtg gtg caa aaa agg cat cat aca agg<br>Gln Pro Pro Val Thr Phe Val Val Val Gln Lys Arg His His Thr Arg<br>                    645                    650                    655 | 1968 |
| ttg ttt gct aac aat cat aat gat cgc cgt gct gta gac agg agt ggg<br>Leu Phe Ala Asn Asn His Asn Asp Arg Arg Ala Val Asp Arg Ser Gly<br>660                    665                    670 | 2016 |
| aat att ttg cct ggc act gtg gtg gac tcc aaa att tgt cac cca acg<br>Asn Ile Leu Pro Gly Thr Val Val Asp Ser Lys Ile Cys His Pro Thr<br>              675                    680                    685 | 2064 |
| gag ttt gac ttc tac tta tgc agc cat gct ggg att cag ggt aca agc<br>Glu Phe Asp Phe Tyr Leu Cys Ser His Ala Gly Ile Gln Gly Thr Ser<br>690                    695                    700 | 2112 |
| cgt cca gct cat tac cat gtg cta tgg gat gag aac aag ttt aca gct<br>Arg Pro Ala His Tyr His Val Leu Trp Asp Glu Asn Lys Phe Thr Ala<br>705                    710                    715                  720 | 2160 |
| gat gca tta cag tct ctt aca aat aac ctt tgc tat aca tat gca agg<br>Asp Ala Leu Gln Ser Leu Thr Asn Asn Leu Cys Tyr Thr Tyr Ala Arg<br>                    725                    730                    735 | 2208 |
| tgc aca cga tca gtg tct att gtt ccc cct gcg tac tac gca cat ctt<br>Cys Thr Arg Ser Val Ser Ile Val Pro Pro Ala Tyr Tyr Ala His Leu<br>740                    745                    750 | 2256 |
| gct gca ttc cga gct cgc ttt tat atg gaa cca gaa aca tca gac agt<br>Ala Ala Phe Arg Ala Arg Phe Tyr Met Glu Pro Glu Thr Ser Asp Ser<br>              755                    760                    765 | 2304 |
| gga tca atg aca agt ggc cct gca g<br>Gly Ser Met Thr Ser Gly Pro Ala<br>770                    775 | 2329 |

<210> SEQ ID NO 24
<211> LENGTH: 776
<212> TYPE: PRT
<213> ORGANISM: Gossypium herbaceum

<400> SEQUENCE: 24

```
Arg Glu Ser Tyr Leu Gly Lys His Leu Pro Ala Tyr Asp Gly Arg Lys
1               5                   10                  15

Ser Leu Tyr Thr Ala Gly Pro Leu Pro Phe Val Ser Lys Glu Phe Arg
            20                  25                  30

Ile Thr Leu Ile Asp Asp Asp Gly Ser Gly Met Gln Arg Arg Glu
        35                  40                  45

Cys Glu Phe Arg Val Val Ile Lys Leu Ala Ala Arg Ala Asp Leu His
    50                  55                  60

His Leu Gly Leu Phe Leu Gln Gly Lys Gln Ala Asp Ala Pro Gln Glu
65                  70                  75                  80

Ala Leu Gln Val Leu Asp Ile Val Leu Arg Glu Leu Pro Thr Thr Arg
                85                  90                  95

Tyr Cys Pro Val Gly Arg Ser Phe Tyr Ser Pro Asp Leu Gly Arg Lys
            100                 105                 110

Gln Pro Leu Gly Glu Gly Ile Glu Ser Trp Arg Gly Phe Tyr Gln Ser
        115                 120                 125

Ile Arg Pro Thr Gln Met Gly Leu Ser Leu Asn Ile Asp Met Ser Ser
130                 135                 140

Thr Ala Phe Ile Glu Pro Leu Pro Val Ile Asp Phe Val Thr Gln Leu
145                 150                 155                 160

Leu Asn Arg Asp Val Ser Ser Arg Pro Leu Ser Asp Ala Asp Arg Val
                165                 170                 175

Lys Ile Lys Lys Ala Leu Arg Gly Val Lys Val Glu Val Thr His Arg
            180                 185                 190

Gly Asn Met Arg Arg Lys Tyr Arg Ile Ser Gly Leu Thr Ser Gln Ala
        195                 200                 205

Thr Arg Glu Leu Thr Phe Pro Val Asp Asp Arg Gly Thr Met Lys Ser
210                 215                 220

Val Val Glu Tyr Phe His Glu Thr Tyr Gly Phe Ile Gln His Thr
225                 230                 235                 240

Gln Trp Pro Cys Leu Gln Val Gly Asn Gln Gln Arg Pro Asn Tyr Leu
                245                 250                 255

Pro Met Glu Val Cys Lys Ile Val Glu Gly Gln Arg Tyr Ser Lys Arg
            260                 265                 270

Leu Asn Glu Lys Gln Ile Thr Ala Leu Leu Lys Val Thr Cys Gln Arg
        275                 280                 285

Pro Gln Glu Arg Glu Tyr Asp Ile Met Lys Thr Val Gln His Asn Ala
290                 295                 300

Tyr His Glu Asp Pro Tyr Ala Lys Glu Phe Gly Ile Lys Ile Ser Glu
305                 310                 315                 320

Lys Leu Ala Ser Val Glu Ala Arg Ile Leu Pro Pro Trp Leu Lys
                325                 330                 335

Tyr His Asp Thr Gly Lys Glu Lys Asp Cys Leu Pro Gln Val Gly Gln
            340                 345                 350

Trp Asn Met Met Asn Lys Lys Met Val Asn Gly Gly Thr Val Asn Asn
        355                 360                 365

Trp Ile Cys Ile Asn Phe Ser Arg Gln Val Gln Asp Ser Val Ala Arg
```

```
            370                 375                 380
Arg Phe Cys Tyr Glu Leu Ala Gln Met Cys Tyr Ile Ser Gly Met Ala
385                 390                 395                 400

Phe Asn Pro Glu Pro Val Leu Pro Pro Ile Ser Ala Arg Pro Glu Tyr
                405                 410                 415

Val Glu Lys Val Leu Lys Thr Arg Tyr His Asp Ala Met Ile Lys Leu
            420                 425                 430

Gln Pro Gln Asn Lys Glu Ile Asp Leu Leu Ile Val Ile Leu Pro Asp
            435                 440                 445

Asn Asn Gly Ser Leu Tyr Gly Asp Leu Lys Arg Ile Cys Glu Thr Asp
450                 455                 460

Leu Gly Ile Val Ser Gln Cys Cys Leu Thr Lys His Val Phe Arg Met
465                 470                 475                 480

Ser Lys Gln Tyr Leu Ala Asn Val Ala Leu Lys Ile Asn Val Lys Val
                485                 490                 495

Gly Gly Arg Asn Thr Val Leu Val Asp Ala Ile Ser Arg Arg Ile Pro
                500                 505                 510

Leu Val Ser Asp Arg Pro Thr Ile Ile Phe Gly Ala Asp Val Thr His
            515                 520                 525

Pro His Pro Gly Glu Asp Ser Ser Pro Ser Ile Ala Ala Val Val Ala
            530                 535                 540

Ser Gln Asp Trp Pro Glu Val Thr Lys Tyr Ala Gly Leu Val Cys Ala
545                 550                 555                 560

Gln Ala His Arg Gln Glu Leu Ile Gln Asp Leu Phe Lys Thr Trp Gln
                565                 570                 575

Asp Pro Ala Arg Gly Thr Val Ser Gly Met Ile Lys Glu Leu Leu
                580                 585                 590

Ile Ser Phe Arg Arg Ala Thr Gly Gln Lys Pro Gln Arg Ile Ile Phe
                595                 600                 605

Tyr Arg Asp Gly Val Ser Glu Gly Gln Phe Tyr Gln Val Leu Leu Tyr
            610                 615                 620

Glu Leu Asp Ala Ile Arg Lys Ala Cys Ala Ser Leu Glu Pro Asn Tyr
625                 630                 635                 640

Gln Pro Pro Val Thr Phe Val Val Gln Lys Arg His His Thr Arg
                645                 650                 655

Leu Phe Ala Asn Asn His Asn Asp Arg Arg Ala Val Asp Arg Ser Gly
                660                 665                 670

Asn Ile Leu Pro Gly Thr Val Val Asp Ser Lys Ile Cys His Pro Thr
                675                 680                 685

Glu Phe Asp Phe Tyr Leu Cys Ser His Ala Gly Ile Gln Gly Thr Ser
                690                 695                 700

Arg Pro Ala His Tyr His Val Leu Trp Asp Glu Asn Lys Phe Thr Ala
705                 710                 715                 720

Asp Ala Leu Gln Ser Leu Thr Asn Asn Leu Cys Tyr Thr Tyr Ala Arg
                725                 730                 735

Cys Thr Arg Ser Val Ser Ile Val Pro Pro Ala Tyr Tyr Ala His Leu
                740                 745                 750

Ala Ala Phe Arg Ala Arg Phe Tyr Met Glu Pro Glu Thr Ser Asp Ser
                755                 760                 765

Gly Ser Met Thr Ser Gly Pro Ala
770                 775

<210> SEQ ID NO 25
```

```
<211> LENGTH: 33
<212> TYPE: DNA
<213> ORGANISM: Gossypium hirsutum

<400> SEQUENCE: 25
ttataggtac catggctagc aaaggagaag aac                          33

<210> SEQ ID NO 26
<211> LENGTH: 35
<212> TYPE: DNA
<213> ORGANISM: Gossypium hirsutum

<400> SEQUENCE: 26
cctaagagct cttaatccat gccatgtgta atccc                        35

<210> SEQ ID NO 27
<211> LENGTH: 162
<212> TYPE: DNA
<213> ORGANISM: Arabidopsis thaliana

<400> SEQUENCE: 27
gtaagtacat ttccataacg ttccatcgtc attgattctt cattagtatg cgtttatgaa    60 gcttttcaa tttaattctc tttggtagat cttaagattc ctctgtttct tgcaaaataa   120
agggttcaat tatgctaata tttttatat caattttgac ag                      162

<210> SEQ ID NO 28
<211> LENGTH: 30
<212> TYPE: DNA
<213> ORGANISM: Gossypium hirsutum

<400> SEQUENCE: 28
atattctaga agaagaacta tgagttgcct                              30

<210> SEQ ID NO 29
<211> LENGTH: 30
<212> TYPE: DNA
<213> ORGANISM: Gossypium hirsutum

<400> SEQUENCE: 29
atgggatccc gtagagatcc ttcctgatat                              30

<210> SEQ ID NO 30
<211> LENGTH: 26
<212> TYPE: DNA
<213> ORGANISM: Gossypium hirsutum

<400> SEQUENCE: 30
gatgttgtgc ccaaggatgt taatgc                                  26

<210> SEQ ID NO 31
<211> LENGTH: 26
<212> TYPE: DNA
<213> ORGANISM: Gossypium hirsutum

<400> SEQUENCE: 31
atgagatcaa acttgtggtc aatgcg                                  26

<210> SEQ ID NO 32
<211> LENGTH: 30
<212> TYPE: DNA
<213> ORGANISM: Gossypium hirsutum

<400> SEQUENCE: 32
```

```
atattctaga agaagaacta tgagttgcct                                              30

<210> SEQ ID NO 33
<211> LENGTH: 30
<212> TYPE: DNA
<213> ORGANISM: Gossypium hirsutum

<400> SEQUENCE: 33
atgggatccc gtagagatcc ttcctgatat                                              30

<210> SEQ ID NO 34
<211> LENGTH: 30
<212> TYPE: DNA
<213> ORGANISM: Gossypium hirsutum

<400> SEQUENCE: 34
tatctgtgga ttcttatggg gtatgtgtgt                                              30

<210> SEQ ID NO 35
<211> LENGTH: 30
<212> TYPE: DNA
<213> ORGANISM: Gossypium hirsutum

<400> SEQUENCE: 35
agaccttcta acttgataac caaatctttg                                              30

<210> SEQ ID NO 36
<211> LENGTH: 30
<212> TYPE: DNA
<213> ORGANISM: Gossypium hirsutum

<400> SEQUENCE: 36
tgaatcctca agtggctgcc attattgagg                                              30

<210> SEQ ID NO 37
<211> LENGTH: 30
<212> TYPE: DNA
<213> ORGANISM: Gossypium hirsutum

<400> SEQUENCE: 37
gcatgtaccc ttgggaagca tataatgtta                                              30

<210> SEQ ID NO 38
<211> LENGTH: 30
<212> TYPE: DNA
<213> ORGANISM: Gossypium hirsutum

<400> SEQUENCE: 38
gcagttggag gaggttatgt gtaatgttca                                              30

<210> SEQ ID NO 39
<211> LENGTH: 30
<212> TYPE: DNA
<213> ORGANISM: Gossypium hirsutum

<400> SEQUENCE: 39
tccgattgat gttgtcgaaa tccaacgtcg                                              30

<210> SEQ ID NO 40
<211> LENGTH: 30
<212> TYPE: DNA
<213> ORGANISM: Gossypium hirsutum
```

```
<400> SEQUENCE: 40
tcatttcagc tgagaaggct taccatgagc                                    30

<210> SEQ ID NO 41
<211> LENGTH: 30
<212> TYPE: DNA
<213> ORGANISM: Gossypium hirsutum

<400> SEQUENCE: 41
tggtagttga taccgcactt gaatccagta                                    30

<210> SEQ ID NO 42
<211> LENGTH: 26
<212> TYPE: DNA
<213> ORGANISM: Gossypium hirsutum

<400> SEQUENCE: 42
atgatgtgcg cggctgatcc tcgtca                                        26

<210> SEQ ID NO 43
<211> LENGTH: 26
<212> TYPE: DNA
<213> ORGANISM: Gossypium hirsutum

<400> SEQUENCE: 43
catctcttgt atcgatgtcg agttcc                                        26

<210> SEQ ID NO 44
<211> LENGTH: 26
<212> TYPE: DNA
<213> ORGANISM: Gossypium hirsutum

<400> SEQUENCE: 44
tgctgatgga tatagtttag tcgtga                                        26

<210> SEQ ID NO 45
<211> LENGTH: 26
<212> TYPE: DNA
<213> ORGANISM: Gossypium hirsutum

<400> SEQUENCE: 45
acaactttct aagtagcaga aagaag                                        26

<210> SEQ ID NO 46
<211> LENGTH: 30
<212> TYPE: DNA
<213> ORGANISM: Gossypium hirsutum

<400> SEQUENCE: 46
gtggtcgaaa attgcacaac acttgcctgg                                    30

<210> SEQ ID NO 47
<211> LENGTH: 30
<212> TYPE: DNA
<213> ORGANISM: Gossypium hirsutum

<400> SEQUENCE: 47
gcttatgttg ctgatacgat cattgtaggt                                    30

<210> SEQ ID NO 48
<211> LENGTH: 30
<212> TYPE: DNA
<213> ORGANISM: Gossypium hirsutum
```

```
<400> SEQUENCE: 48
agatggataa attacttaag accagatatc                              30

<210> SEQ ID NO 49
<211> LENGTH: 30
<212> TYPE: DNA
<213> ORGANISM: Gossypium hirsutum

<400> SEQUENCE: 49
atctaccagc tatcagtgac cacctaacac                              30

<210> SEQ ID NO 50
<211> LENGTH: 26
<212> TYPE: DNA
<213> ORGANISM: Gossypium hirsutum

<400> SEQUENCE: 50
gatgttgtgc ccaaggatgt taatgc                                  26

<210> SEQ ID NO 51
<211> LENGTH: 26
<212> TYPE: DNA
<213> ORGANISM: Gossypium hirsutum

<400> SEQUENCE: 51
atgagatcaa acttgtggtc aatgcg                                  26

<210> SEQ ID NO 52
<211> LENGTH: 24
<212> TYPE: DNA
<213> ORGANISM: Gossypium hirsutum

<400> SEQUENCE: 52
ctgaatcttc gctttcacgt tatc                                    24

<210> SEQ ID NO 53
<211> LENGTH: 23
<212> TYPE: DNA
<213> ORGANISM: Gossypium hirsutum

<400> SEQUENCE: 53
gggatgcaaa tcttcgtgaa aac                                     23

<210> SEQ ID NO 54
<211> LENGTH: 37
<212> TYPE: DNA
<213> ORGANISM: Gossypium hirsutum

<400> SEQUENCE: 54
aaatatctag aggtgctact gaagataggg tctgtgg                      37

<210> SEQ ID NO 55
<211> LENGTH: 26
<212> TYPE: DNA
<213> ORGANISM: Gossypium hirsutum

<400> SEQUENCE: 55
gactccaaag gatccttgcg aagacg                                  26

<210> SEQ ID NO 56
<211> LENGTH: 35
<212> TYPE: DNA
```

<213> ORGANISM: Gossypium hirsutum

<400> SEQUENCE: 56
ttatttctag agcacgagct tcctttgtat ctgcc                    35

<210> SEQ ID NO 57
<211> LENGTH: 37
<212> TYPE: DNA
<213> ORGANISM: Gossypium hirsutum

<400> SEQUENCE: 57
tcctaggatc caatattggt gtatgacctg catccgc                  37

<210> SEQ ID NO 58
<211> LENGTH: 32
<212> TYPE: DNA
<213> ORGANISM: Gossypium hirsutum

<400> SEQUENCE: 58
aataatctag aagagaagta tgccaacgac ca                       32

<210> SEQ ID NO 59
<211> LENGTH: 33
<212> TYPE: DNA
<213> ORGANISM: Gossypium hirsutum

<400> SEQUENCE: 59
gctatggatc cggagggaac agtggaggtt cgg                      33

<210> SEQ ID NO 60
<211> LENGTH: 34
<212> TYPE: DNA
<213> ORGANISM: Gossypium hirsutum

<400> SEQUENCE: 60
aataatctag acttgtaaca ctacaagagt tggg                     34

<210> SEQ ID NO 61
<211> LENGTH: 33
<212> TYPE: DNA
<213> ORGANISM: Gossypium hirsutum

<400> SEQUENCE: 61
gagctggatc cgggctcggc atacgtcttc cac                      33

<210> SEQ ID NO 62
<211> LENGTH: 35
<212> TYPE: DNA
<213> ORGANISM: Gossypium hirsutum

<400> SEQUENCE: 62
aataatctag acactcatca accatatcca gtacc                    35

<210> SEQ ID NO 63
<211> LENGTH: 35
<212> TYPE: DNA
<213> ORGANISM: Gossypium hirsutum

<400> SEQUENCE: 63
gtcctggatc cacaattccc aacactagtc ctcgg                    35

<210> SEQ ID NO 64
<211> LENGTH: 32

<210> SEQ ID NO 64
<211> LENGTH: 32
<212> TYPE: DNA
<213> ORGANISM: Gossypium hirsutum

<400> SEQUENCE: 64
atggcggatc ctgttggaaa ttcgctagct gg        32

<210> SEQ ID NO 65
<211> LENGTH: 35
<212> TYPE: DNA
<213> ORGANISM: Gossypium hirsutum

<400> SEQUENCE: 65
gtcctggatc catactcagg catccataga ggaag     35

<210> SEQ ID NO 66
<211> LENGTH: 18
<212> TYPE: DNA
<213> ORGANISM: Gossypium hirsutum

<400> SEQUENCE: 66
aaggcagagc aagagaag                        18

<210> SEQ ID NO 67
<211> LENGTH: 18
<212> TYPE: DNA
<213> ORGANISM: Gossypium hirsutum

<400> SEQUENCE: 67
tctattagtg acaatatc                        18

<210> SEQ ID NO 68
<211> LENGTH: 18
<212> TYPE: DNA
<213> ORGANISM: Gossypium hirsutum

<400> SEQUENCE: 68
tttgtatctg cccaaccc                        18

<210> SEQ ID NO 69
<211> LENGTH: 18
<212> TYPE: DNA
<213> ORGANISM: Gossypium hirsutum

<400> SEQUENCE: 69
tattggtgta tgacctgc                        18

<210> SEQ ID NO 70
<211> LENGTH: 18
<212> TYPE: DNA
<213> ORGANISM: Gossypium hirsutum

<400> SEQUENCE: 70
gtgggtgacc gctaaatg                        18

<210> SEQ ID NO 71
<211> LENGTH: 18
<212> TYPE: DNA
<213> ORGANISM: Gossypium hirsutum

<400> SEQUENCE: 71
ggctcacaga aaactgcc                        18

<210> SEQ ID NO 72

-continued

<210> SEQ ID NO 72
<211> LENGTH: 18
<212> TYPE: DNA
<213> ORGANISM: Gossypium hirsutum

<400> SEQUENCE: 72
tgcagtgctg tcaatacc                                                      18

<210> SEQ ID NO 73
<211> LENGTH: 19
<212> TYPE: DNA
<213> ORGANISM: Gossypium hirsutum

<400> SEQUENCE: 73
ctctgaggaa atgatcaac                                                     19

<210> SEQ ID NO 74
<211> LENGTH: 22
<212> TYPE: DNA
<213> ORGANISM: Gossypium hirsutum

<400> SEQUENCE: 74
cgactccgcc ttagctgctg ac                                                 22

<210> SEQ ID NO 75
<211> LENGTH: 21
<212> TYPE: DNA
<213> ORGANISM: Gossypium hirsutum

<400> SEQUENCE: 75
gaactgatcc aagccaaccg g                                                  21

<210> SEQ ID NO 76
<211> LENGTH: 653
<212> TYPE: DNA
<213> ORGANISM: Gossypium hirsutum

<400> SEQUENCE: 76
ggtgctactg aagatagggt ctgtggaacc attgacattg agaaagccct cactgagggt        60
gtcaaggcat ttgagcctgg acttctagct aaagctaatc gagggattct ttacgtcgat       120
gaagttaacc ttttagatga ccatttggtg gatgttcttt tggattccgc tgcatcagga       180
tggaacactg ttgagaggga aggtatttcg atctcacatc ctgctcggtt tattctcatc       240
ggctcaggta atccagaaga aggagagctt agaccacagc ttcttgatcg attcggaatg       300
catgctcaag tcgggacagt gagggacgct gagcttagag tgaagattgt ggaggaaaga       360
gcacggtttg ataaaaaccc aaaagaattc cgtgattctt acaaggcaga gcaagagaag       420
ctccaacagc agattgcttc agctaggagt tctctttctt ctgttcagat tgatcaagac       480
ctaaaggtta aatatcaaa ggtttgtgct gagttgaatg ttgatggatt gagaggagat       540
attgtcacta atagagctgc aaaagctctt gcagctctta aggaagaga taaagtcatt       600
gcagaagata ttgccactgt catccccaac tgcttgagac accgtcttcg caa              653

<210> SEQ ID NO 77
<211> LENGTH: 479
<212> TYPE: DNA
<213> ORGANISM: Gossypium hirsutum

<400> SEQUENCE: 77
gcacgagctt cctttgtatc tgcccaaccc actttccata tcccactttc tattcaactc        60
aagttcttta ctcacctttg ctttgaattc ggtcatctga gctttgggat ttttgtcttg       120

```
aagaaaatga gtctctgtgg gagtgtttct gccctgtact taaacttaca aagcagcaag    180
ataagcatgg gaaatgtctt agcttttaga agtggtgaat ccatgggaaa taccttgaga    240 attccctta  aaaagaggtc acgtaagggt gctggttgtc ctttgcaggt agtttgcata    300
gattatccaa ggccagagct agagaatact gttaattttt tggaggctgc ttctctatct    360
gcttcttttc gttcagcttc ccgtccaact aaaccattga aagtcataat tgctggtgca    420
ggtttggctg gtttgtcaac tgcaaagtat cttgcggatg caggtcatac accaatatt     479
```

<210> SEQ ID NO 78
<211> LENGTH: 663
<212> TYPE: DNA
<213> ORGANISM: Gossypium hirsutum

<400> SEQUENCE: 78

```
agagaagtat gccaacgacc agagctctgg gaatgttcag ggctatggta gcaagcttgc    60
taacaatgct agtgggcagc ttgagtggga ggactacttc ttccatctta ttttcctga    120 ggataagaga gacttgtcaa tttggcctaa atccccagc gaatacactg aagttacaag    180
tgagtatgca aggcaactgc gaggcctagc gagcaaaata ctttcagcac tatcaatttg    240
cttgggatta gaagaaggaa ggctagagaa ggaagttggt ggcgtggaag agcttcttct    300
tcaattgaaa atcaattact accccaagtg tccacaacca gaactcgctc tcggtgtcga    360
agctcacacc gatataagtg cactcacttt cattctccac aacatggttc ctggcctcca    420
actcttttac caaggcaagt gggtgaccgc taaatgtgtt cccaactcca tcatcatgca    480
cattggagac accatcgaga tcctcagcaa tggaaagttc aagagcattc tccacagggg    540
tctggttaat aaggagaagg ttaggatctc atgggcagtt ttctgtgagc caccgaagga    600
taagatcatc cttaagccac tcccggagac tgtctctgag accgaacctc cactgttccc    660
tcc                                                                  663
```

<210> SEQ ID NO 79
<211> LENGTH: 595
<212> TYPE: DNA
<213> ORGANISM: Gossypium hirsutum

<400> SEQUENCE: 79

```
cttgtaacac tacaagagtt gggagacttg aaaatctttc aggcggattt aactgatgaa    60
gggagctttg atgcccctat tgctggttgt gaccttgtct tccatgttgc gacacccgtt    120
aactttgctt ctgaagatcc agagaatgac atgatcaaac cagcgaccca aggagtggtg    180
aacgttttga aagcttgtgc caaagcaaaa acagttaaac gtgtcgtctt gacatcatct    240
gccgcagctg tgtctatcaa cacactgaat gggacagatc tggtcatgac agagaaagac    300
tggaccgata tcgagttctt atcatcagca aagccaccaa cttgggggta ccctgcatcc    360
aagacgttgg ctgaaaaggc agcttggaaa tttgctgaag aaaacaacat tgatctcatt    420
acagttatcc cttctctcat gactggtcct tccctcaccc caattgtccc cagcagcata    480
ggccttgcta catctttgat ttcaggcaat gaattcctca taaatgcttt gaaaggaatg    540
cagatgctgt caggttcgat ctctatcaca catgtggaag acgtatgccg agccc         595
```

<210> SEQ ID NO 80
<211> LENGTH: 621
<212> TYPE: DNA
<213> ORGANISM: Gossypium hirsutum

<400> SEQUENCE: 80

```
cactcatcaa ccatatccag taccagtaac ctctaattcc cacccgaagt ctcttttaac    60
ctcgtcacaa tagtgagtgc acgatccgag gatgaacgtc gcctccaact ccacgacgtc   120
gcctatgctc agatcctctt ccggaatgcg tcaccgtgac aacccctacgc ctctcccttt   180
ggttatttcc ctcaactgca tcgaagattg cgccctcgag caagaatcct tagccagcgt   240
cgcagtggtc caccacgtcc ctctcagcag cttaggcgac gggaagatcg aggggggccgc   300
cgccgttctt ctccactccc tttcctacct ccctcgagct gcccagcgtc gcctccgtcc   360
ttaccagctc atcctctgcc tcggctcctc tgaccgcgcc gtcgactccg ccttagccgc   420
tgacctcgga ctacgtcttg tccatgtcga cgcctcgcga gctgaggaga tcgcagacac   480
tgtcatggcg ctgtttctgg gcttgctccg tcgcacgcac ttgctctctc gccacgcgct   540
ttcggcttcc ggttggcttg gatcagttca gccgctttgt cggggaatga ggcggtgccg   600
aggactagtg ttgggaattg t                                             621
```

<210> SEQ ID NO 81
<211> LENGTH: 675
<212> TYPE: DNA
<213> ORGANISM: Gossypium hirsutum

<400> SEQUENCE: 81

```
gctcagatca acaagcatct aaacacactt gatgacccgt taattcgatc caaatggatg    60
aatgtgaaga aagcactgtc tgaggagaca gaagttgtga agcaattgga tgctgagaga   120
aggtcattta aggaagctcc aaatgggcgg cgtccttctt caccaccgat tcatgcaaaa   180
tcatcttttg tgtttcaacc tcttgatgag tacccaactt catcgggtgc tccaatggat   240
gatcctgatg tgtggaggcc tccaagtcgg gacacatcaa ctagaagacc tgctaggggt   300
ggtcaagcgg gaatgagaaa gtctccccaa gatgggattt cgggtcgtgg taatactaga   360
acagctgcaa ctggacgtgg tgctaaggct ggtgcttcaa gtagaactaa cacgggggtc   420
agaggatcta ccactggaaa aaagggtact ggttctggga atctagcaa aggcgattcg   480
gcaaatggtg atgctgaaga tggaaagttg aagaggtcac agtatgaggg gcctgatcca   540
gatttagctg aaatgctgga aagggatgtc ttagaaacca ctcctggagt gcggtgggat   600
gatgttgctg gtttgactga agcaaaaagg cttttagagg aagctgttgt tcttcctcta   660
tggatgcctg agtat                                                    675
```

<210> SEQ ID NO 82
<211> LENGTH: 9696
<212> TYPE: DNA
<213> ORGANISM: Artificial Sequence
<220> FEATURE:
<223> OTHER INFORMATION: sequence of synthetic psTRV2001 vector
<220> FEATURE:
<221> NAME/KEY: misc_feature
<222> LOCATION: (6785)..(9696)
<223> OTHER INFORMATION: sequence of synthetic sTRV2

<400> SEQUENCE: 82

```
gggaattcta agaggagtcc accatggtag atctgactag tgttaacgct agccaccacc    60
accaccacca cgtgtgaatt acaggtgacc agctcgaatt tccccgatcg ttcaaacatt   120
tggcaataaa gtttcttaag attgaatcct gttgccggtc ttgcgatgat tatcatataa   180
tttctgttga attacgttaa gcatgtaata attaacatgt aatgcatgac gttatttatg   240
agatgggttt ttatgattag agtcccgcaa ttatacattt aatacgcgat agaaaacaaa   300
```

-continued

```
atatagcgcg caaactagga taaattatcg cgcgcggtgt catctatgtt actagatcgg    360
gaattaaact atcagtgttt gacaggatat attggcgggt aaacctaaga gaaaagagcg    420
tttattagaa taacggatat ttaaaagggc gtgaaaaggt ttatccgttc gtccatttgt    480
atgtgcatgc caaccacagg gttcccctcg ggatcaaagt actttgatcc aacccctccg    540
ctgctatagt gcagtcggct tctgacgttc agtgcagccg tcttctgaaa cgacatgtc     600
gcacaagtcc taagttacgc gacaggctgc cgccctgccc ttttcctggc gttttcttgt    660
cgcgtgtttt agtcgcataa agtagaatac ttgcgactag aaccggagac attacgccat    720
gaacaagagc cgccgcctg gcctgctggg ctatgcccgc gtcagcaccg acgaccagga     780
cttgaccaac caacgggccg aactgcacgc ggccggctgc accaagctgt tttccgagaa    840
gatcaccggc accaggcgcg accgcccgga gctggccagg atgcttgacc acctacgccc    900
tggcgacgtt gtgacagtga ccaggctaga ccgcctggcc cgcagcaccc gcgacctact    960
ggacattgcc gagcgcatcc aggaggccgg cgcgggcctg cgtagcctgg cagagccgtg   1020
ggccgacacc accacgccgg ccggccgcat ggtgttgacc gtgttcgccg gcattgccga   1080
gttcgagcgt tccctaatca tcgaccgcac ccggagcggg cgcgaggccg ccaaggcccg   1140
aggcgtgaag tttggccccc gccctaccct caccccggca cagatcgcgc acgcccgcga   1200
gctgatcgac caggaaggcc gcaccgtgaa agaggcggct gcactgcttg gcgtgcatcg   1260
ctcgaccctg taccgcgcac ttgagcgcag cgaggaagtg acgcccaccg aggccaggcg   1320
gcgcggtgcc ttccgtgagg acgcattgac cgaggccgac gccctggcgg ccgccgagaa   1380
tgaacgccaa gaggaacaag catgaaaccg caccaggacg gccaggacga accgtttttc   1440
attaccgaag agatcgaggc ggagatgatc gcggccgggt acgtgttcga ccgccgcgcg   1500
cacgtctcaa ccgtgcggct gcatgaaatc ctggccggtt tgtctgatgc caagctggcg   1560
gcctggccgg ccagcttggc cgctgaagaa accgagcgcc gccgtctaaa aggtgatgt    1620
gtatttgagt aaaacagctt gcgtcatgcg gtcgctgcgt atatgatgcg atgagtaaat   1680
aaacaaatac gcaaggggaa cgcatgaagg ttatcgctgt acttaaccag aaaggcgggt   1740
caggcaagac gaccatcgca acccatctag cccgcgccct gcaactcgcc ggggccgatg   1800
ttctgttagt cgattccgat ccccagggca gtgcccgcga ttgggcggcc gtgcgggaag   1860
atcaaccgct aaccgttgtc ggcatcgacc gcccgacgat tgaccgcgac gtgaaggcca   1920
tcggccggcg cgacttcgta gtgatcgacg agcgccccca ggcggcggac ttggctgtgt   1980
ccgcgatcaa ggcagccgac ttcgtgctga ttccggtgca gccaagccct tacgacatat   2040
gggccaccgc cgacctggtg gagctggtta agcagcgcat tgaggtcacg gatggaaggc   2100
tacaagcggc ctttgtcgtg tcgcgggcga tcaaaggcac gcgcatcggc ggtgaggttg   2160
ccgaggcgct ggccgggtac gagctgccca ttcttgagtc ccgtatcacg cagcgcgtga   2220
gctacccagg cactgccgcc gccggcacaa ccgttcttga atcagaaccc gagggcgacg   2280
ctgcccgcga ggtccaggcg ctggccgctg aaattaaatc aaaactcatt tgagttaatg   2340
aggtaaagag aaaatgagca aaagcacaaa cacgctaagt gccggccgtc cgagcgcacg   2400
cagcagcaag gctgcaacgt tggccagcct ggcagacacg ccagccatga gcgggtcaa    2460
ctttcagttg ccggcggagg atcacaccaa gctgaagatg tacgcggtac gccaaggcaa   2520
gaccattacc gagctgctat ctgaatacat cgcgcagcta ccagagtaaa tgagcaaatg   2580
aataaaatgag tagatgaatt ttagcggcta aaggaggcgg catggaaaat caagaacaac   2640
```

```
caggcaccga cgccgtggaa tgccccatgt gtggaggaac gggcggttgg ccaggcgtaa    2700
gcggctgggt tgtctgccgg ccctgcaatg gcactggaac ccccaagccc gaggaatcgg    2760
cgtgacggtc gcaaaccatc cggcccggta caaatcggcg cggcgctggg tgatgacctg    2820
gtggagaagt tgaaggccgc gcaggccgcc cagcggcaac gcatcgaggc agaagcacgc    2880
cccggtgaat cgtggcaagc ggccgctgat cgaatccgca agaatcccg gcaaccgccg     2940
gcagccggtg cgccgtcgat taggaagccg cccaagggcg acgagcaacc agattttttc    3000
gttccgatgc tctatgacgt gggcacccgc gatagtcgca gcatcatgga cgtggccgtt    3060
ttccgtctgt cgaagcgtga ccgacgagct ggcgaggtga tccgctacga gcttccagac    3120
gggcacgtag aggttttccgc agggccggcc ggcatggcca gtgtgtggga ttacgacctg    3180
gtactgatgg cggttttccca tctaaccgaa tccatgaacc gataccggga agggaaggga    3240
gacaagcccg gccgcgtgtt ccgtccacac gttgcggacg tactcaagtt ctgccggcga    3300
gccgatggcg gaaagcagaa agacgacctg gtagaaacct gcattcggtt aaacaccacg    3360
cacgttgcca tgcagcgtac gaagaaggcc aagaacggcc gcctggtgac ggtatccgag    3420
ggtgaagcct tgattagccg ctacaagatc gtaaagagcg aaaccgggcg gccggagtac    3480
atcgagatcg agctagctga ttggatgtac cgcgagatca cagaaggcaa gaacccggac    3540
gtgctgacgg ttcaccccga ttacttttg atcgatcccg gcatcggccg ttttctctac     3600
cgcctggcac gccgcgccgc aggcaaggca gaagccagat ggttgttcaa gacgatctac    3660
gaacgcagtg gcagcgccgg agagttcaag aagttctgtt tcaccgtgcg caagctgatc    3720
gggtcaaatg acctgccgga gtacgatttg aaggaggagg cggggcaggc tggcccgatc    3780
ctagtcatgc gctaccgcaa cctgatcgag ggcgaagcat ccgccggttc ctaatgtacg    3840
gagcagatgc tagggcaaat tgccctagca ggggaaaaag gtcgaaaagg tctcttttcct   3900
gtggatagca cgtacattgg aacccaaag ccgtacattg ggaaccggaa cccgtacatt     3960
gggaaccccaa agccgtacat tgggaaccgg tcacacatgt aagtgactga tataaaagag   4020
aaaaaaggcg attttccgc ctaaaactct ttaaaactta ttaaaactct taaaacccgc     4080
ctggcctgtg cataactgtc tggccagcgc acagccgaag agctgcaaaa agcgcctacc    4140
cttcggtcgc tgcgctccct acgccccgcc gcttcgcgtc ggcctatcgc ggccgctggc    4200
cgctcaaaaa tggctggcct acggccaggc aatctaccag ggcgcggaca agccgcgccg    4260
tcgccactcg accgccggcg cccacatcaa ggcaccctgc ctcgcgcgtt tcggtgatga    4320
cggtgaaaac ctctgacaca tgcagctccc ggagacggtc acagcttgtc tgtaagcgga    4380
tgccgggagc agacaagccc gtcagggcgc gtcagcgggt gttggcgggt gtcggggcgc    4440
agccatgacc cagtcacgta gcgatagcgg agtgtatact ggcttaacta tgcggcatca    4500
gagcagattg tactgagagt gcaccatatg cggtgtgaaa taccgcacag atgcgtaagg    4560
agaaaatacc gcatcaggcg ctcttccgct tcctcgctca ctgactcgct gcgctcggtc    4620
gttcggctgc ggcgagcggt atcagctcac tcaaaggcgg taatacggtt atccacagaa    4680
tcagggata acgcaggaaa gaacatgtga gcaaaaggcc agcaaaaggc caggaaccgt     4740
aaaaaggccg cgttgctggc gttttttccat aggctccgcc cccctgacga gcatcacaaa   4800
aatcgacgct caagtcagag gtggcgaaac ccgacaggac tataaagata ccaggcgttt    4860
ccccctggaa gctccctcgt gcgctctcct gttccgaccc tgccgcttac cggatacctg    4920
tccgcctttc tcccttcggg aagcgtggcg ctttctcata gctcacgctg taggtatctc    4980
agttcggtgt aggtcgttcg ctccaagctg ggctgtgtgc acgaaccccc cgttcagccc    5040
```

```
gaccgctgcg ccttatccgg taactatcgt cttgagtcca acccggtaag acacgactta   5100
tcgccactgg cagcagccac tggtaacagg attagcagag cgaggtatgt aggcggtgct   5160
acagagttct tgaagtggtg gcctaactac ggctacacta aaggacagt  atttggtatc   5220
tgcgctctgc tgaagccagt taccttcgga aaaagagttg gtagctcttg atccggcaaa   5280
caaaccaccg ctggtagcgg tggttttttt gtttgcaagc agcagattac gcgcagaaaa   5340
aaaggatctc aagaagatcc tttgatcttt tctacggggt ctgacgctca gtggaacgaa   5400
aactcacgtt aagggatttt ggtcatgcat tctaggtact aaaacaattc atccagtaaa   5460
atataatatt ttattttctc ccaatcaggc ttgatcccca gtaagtcaaa aaatagctcg   5520
acatactgtt cttccccgat atcctccctg atcgaccgga cgcagaaggc aatgtcatac   5580
cacttgtccg ccctgccgct tctcccaaga tcaataaagc cacttacttt gccatctttc   5640
acaaagatgt tgctgtctcc caggtcgccg tgggaaaaga caagttcctc ttcgggcttt   5700
tccgtcttta aaaaatcata cagctcgcgc ggatctttaa atggagtgtc ttcttcccag   5760
ttttcgcaat ccacatcggc cagatcgtta ttcagtaagt aatccaattc ggctaagcgg   5820
ctgtctaagc tattcgtata gggacaatcc gatatgtcga tggagtgaaa gagcctgatg   5880
cactccgcat acagctcgat aatcttttca gggctttgtt catcttcata ctcttccgag   5940
caaaggacgc catcggcctc actcatgagc agattgctcc agccatcatg ccgttcaaag   6000
tgcaggacct ttggaacagg cagctttcct tccagccata gcatcatgtc cttttcccgt   6060
tccacatcat aggtggtccc tttataccgg ctgtccgtca ttttttaaata taggttttca   6120
ttttctccca ccagcttata taccttagca ggagacattc cttccgtatc ttttacgcag   6180
cggtatttt  cgatcagttt tttcaattcc ggtgatattc tcattttagc catttattat   6240
ttccttcctc ttttctacag tatttaaaga taccccaaga agctaattat aacaagacga   6300
actccaattc actgttcctt gcattctaaa accttaaata ccagaaaaca gcttttttcaa   6360
agttgtttc  aaagttggcg tataacatag tatcgacgga gccgattttg aaaccgcggt   6420
gatcacaggc agcaacgctc tgtcatcgtt acaatcaaca tgctaccctc cgcgagatca   6480
tccgtgtttc aaacccggca gcttagttgc cgttcttccg aatagcatcg gtaacatgag   6540
caaagtctgc cgccttacaa cggctctccc gctgacgccg tcccggactg atgggctgcc   6600
tgtatcgagt ggtgattttg tgccgagctg ccggtcgggg agctgttggc tggctggtgg   6660
caggatatat tgtggtgtaa acaaattgac gcttagacaa cttaataaca cattgcggac   6720
gtttttaatg tactgaatta acgccgaatt aattcctagg ccaccatgtt gggcccggcg   6780
cgccaagctt ggtcaacatg gtggagcacg acactctcgt ctactccaag aatatcaaag   6840
atacagtctc agaagaccag agggctattg agacttttca acaagggta  atatcgggaa   6900
acctcctcgg attccattgc ccagctatct gtcacttcat cgaaaggaca gtagaaaagg   6960
aagatggctt ctacaaatgc catcattgcg ataaaggaaa ggctatcgtt caagatgcct   7020
ctaccgacag tggtcccaaa gatggacccc cacccacgag gaacatcgtg gaaaaagaag   7080
acgttccaac cacgtcttca aagcaagtgg attgatgtga tggtcaacat ggtggagcac   7140
gacactctcg tctactccaa gaatatcaaa gatacagtct cagaagacca gagggctatt   7200
gagactttc  aacaaagggt aatatcggga aacctcctcg gattccattg cccagctatc   7260
tgtcacttca tcgaaaggac agtagaaaag gaagatggct tctacaaatg ccatcattgc   7320
gataaaggaa aggctatcgt tcaagatgcc tctaccgaca gtggtcccaa agatggaccc   7380
```

-continued

```
ccacccacga ggaacatcgt ggaaaaagaa gacgttccaa ccacgtcttc aaagcaagtg    7440
gattgatgtg atatctccac tgacgtaagg gatgacgcac aatcccacta tccttcgcaa    7500
gacccttcct ctatataagg aagttcattt catttggaga ggataaaaca ttgcacctat    7560
ggtgttgccc tggctggggt atgtcagtga tcgcagtaga atgtactaat tgacaagttg    7620
gagaatacgg tagaacgtcc ttatccaaca cagcctttat ccctctccct gacgaggttt    7680
ttgtcagtgt aatatttctt tttgaactat ccagcttagt accgtacggg aaagtgactg    7740
gtgtgcttat ctttgaaatg ttactttggg tttcggttct ttaggttagt aagaaagcac    7800
ttgtcttctc atacaaagga aaacctgaga cgtatcgctt acgaaagtag caatgaaaga    7860
aaggtggtgg ttttaatcgc taccgcaaaa acgatggggt cgttttaatt aacttctcct    7920
acgcaagcgt ctaaacggac gttggggttt tgctagtttc tttagagaaa actagctaag    7980
tctttaatgt tatcattaga gatggcataa atataatact tgtgtctgct gataagatca    8040
ttttaatttg gacgattaga cttgttgaac tacaggttac tgaatcactt gcgctaatca    8100
acatgggaga tatgtacgat gaatcatttg acaagtcggg cggtcctgct gacttgatgg    8160
acgattcttg ggtggaatca gtttcgtgga aagatctgtt gaagaagtta cacagcataa    8220
aatttgcact acagtctggt agagatgaga tcactgggtt actagcggca ctgaatagac    8280
agtgtcctta ttcaccatat gagcagtttc cagataagaa ggtgtatttc cttttagact    8340
cacgggctaa cagtgctctt ggtgtgattc agaacgcttc agcgttcaag agacgagctg    8400
atgagaagaa tgcagtggcg ggtgttacaa atattcctgc gaatccaaac acaacggtta    8460
cgacgaacca agggagtact actactacca aggcgaacac tggctcgact ttggaagaag    8520
acttgtacac ttattacaaa ttcgatgatg cctctacagc tttccacaaa tctctaactt    8580
cgttagagaa catggagttg aagagttatt accgaaggaa ctttgagaaa gtattcggga    8640
ttaagtttgg tggagcagct gctagttcat ctgcaccgcc tccagcgagt ggaggtccga    8700
tacgtcctaa tccctaggga tttaaggacg tgaactctgt tgagatctct gtgaaattca    8760
gagggtgggt gataccatat tcactgatgc cattagcgac atctaaatag ggctaattgt    8820
gactaatttg agggaatttc ctttaccatt gacgtcagtg tcgttggtag catttgagtt    8880
tcgcaatgca cgaattactt aggaagtggc ttgacgacac taatgtgtta ttgttagata    8940
atggtttggt ggtcaaggta cgtagtagag tcccacatat tcgcacgtat gaagtaattg    9000
gaaagttgtc agttttttgat aattcactgg gagatgatac gctgtttgag ggaaaagtag    9060
agaacgtatt tgttttatg ttcaggcggt tcttgtgtgt caacaaagat ggacattgtt    9120
actcaaggaa gcacgatgag ctttattatt acggacgagt ggacttagat tctgtgagta    9180
aggttaccga attctctaga aggcctccat ggggatccgg taccgagctc acgcgtctcg    9240
aggcccgggc atgtcccgaa gacattaaac tacggttctt taagtagatc cgtgtctgaa    9300
gttttaggtt caatttaaac ctacgagatt gacattctcg actgatcttg attgatcggt    9360
aagtcttttg taatttaatt ttcttttga ttttatttta aattgttatc tgtttctgtg    9420
tatagactgt ttgagatcgg cgtttggccg actcattgtc ttaccatagg gaacggact    9480 ttgtttgtgt tgttattta tttgtatttt attaaaattc tcaacgatct gaaaaagcct    9540
cgcggctaag agattgttgg ggggtgagta agtacttta aagtgatgat ggttacaaag    9600
gcaaaagggg taaaacccct cgcctacgta agcgttatta cgcccgtctg tacttatatc    9660
agtacactga cgagtcccta aaggacgaaa cgggtt                              9696
```